(12) United States Patent
Childs et al.

(10) Patent No.: US 11,293,010 B2
(45) Date of Patent: Apr. 5, 2022

(54) METHODS OF PRODUCING MODIFIED NATURAL KILLER CELLS AND METHODS OF USE

(71) Applicant: The United States of America, as represented by the Secretary, Dept. of Health and Human Services, Bethesda, MD (US)

(72) Inventors: Richard W. Childs, Rockville, MD (US); David S. J. Allan, Rockville, MD (US)

(73) Assignee: The United States of America, as represented by the Secretary, Department and of Health and Human Services, Bethesda, MD (US)

( * ) Notice: Subject to any disclaimer, the term of this patent is extended or adjusted under 35 U.S.C. 154(b) by 1010 days.

(21) Appl. No.: 15/801,085

(22) Filed: Nov. 1, 2017

(65) Prior Publication Data

US 2018/0057795 A1 Mar. 1, 2018

Related U.S. Application Data

(63) Continuation-in-part of application No. PCT/US2017/043774, filed on Jul. 25, 2017.

(60) Provisional application No. 62/366,493, filed on Jul. 25, 2016.

(51) Int. Cl.
| | | |
|---|---|---|
| *C12N 5/0783* | (2010.01) | |
| *C12N 5/00* | (2006.01) | |
| *C12N 15/867* | (2006.01) | |
| *A61K 35/17* | (2015.01) | |

(52) U.S. Cl.
CPC ......... *C12N 5/0646* (2013.01); *C12N 5/0068* (2013.01); *C12N 15/867* (2013.01); *A61K 35/17* (2013.01); *C12N 2501/2302* (2013.01); *C12N 2501/505* (2013.01); *C12N 2501/515* (2013.01); *C12N 2501/599* (2013.01); *C12N 2501/65* (2013.01); *C12N 2501/999* (2013.01); *C12N 2502/1135* (2013.01); *C12N 2502/30* (2013.01); *C12N 2502/99* (2013.01); *C12N 2510/00* (2013.01); *C12N 2510/04* (2013.01); *C12N 2740/15041* (2013.01); *C12N 2740/15043* (2013.01); *C12N 2799/027* (2013.01)

(58) Field of Classification Search
CPC .............................. C12N 5/0646; C12N 15/867
See application file for complete search history.

(56) References Cited

U.S. PATENT DOCUMENTS

| | | | |
|---|---|---|---|
| 2013/0266551 A1 | 10/2013 | Campana et al. | |
| 2018/0185463 A1* | 7/2018 | Borriello | A61P 35/00 |
| 2020/0392457 A1* | 12/2020 | Childs | C07K 14/7051 |

FOREIGN PATENT DOCUMENTS

| | | |
|---|---|---|
| WO | WO 2014/179759 | 11/2014 |
| WO | WO 2015/112793 | 7/2015 |
| WO | WO 2016/073595 | 5/2016 |
| WO | WO 2016/077734 | 5/2016 |
| WO | WO 2016/085946 | 6/2016 |
| WO | WO 2017/059177 | 4/2017 |
| WO | WO 2018/022646 | 2/2018 |

OTHER PUBLICATIONS

Imai et al.; Genetic modification of primary natural killer cells overcomes inhibitory signals and induces specific killing of leukemic cells; Blood, vol. 106, No. 1, pp. 376-383, Jul. 1, 2005 (Year: 2005).*
Cho et al., "Expansion and Activation of Natural Killer Cells for Cancer Immunotherapy," *Korean J Lab Med*, vol. 29, No. 2, pp. 89-96, 2009 (Author Manuscript version, 10 pages).
Imai et al., "Genetic modification of primary natural killer cells overcomes inhibitory signals and induces specific killing of leukemic cells," *Blood*, vol. 106, No. 1, pp. 376-383, 2005.
Lapteva et al., "Large-scale ex vivo expansion and characterization of natural killer cells for clinical applications," *Cytotherapy*, vol. 14, No. 9, pp. 1131-1143, 2012.
Ramanathan et al., "Lentiviral Transduction of Ex Vivo Expanded Natural Killer Cells with a CD19 Chimeric Antigen Receptor Induces Cytotoxicity against Resistant B Cell Malignancies," *Blood*, vol. 112, No. 11, 3540, 2008 (4 pages, Abstract).
Streltsova et al., "Retroviral gene transfer into primary human NK cells activated by IL-2 and K562 feeder cells expressing membrane-bound IL-21," *Journal of Immunological Methods*, vol. 450, pp. 90-94, 2017.
Sutlu et al., "Inhibition of Intracellular Antiviral Defense Mechanisms Augments Lentiviral Transduction of Human Natural Killer Cells: Implications for Gene Therapy," *Human Gene Therapy*, vol. 23, No. 10, pp. 1090-1100, 2012.
Tran et al., "Lentiviral Vectors Mediate Stable and Efficient Gene Delivery into Primary Murine Natural Killer Cells," *Molecular Therapy*, vol. 15, No. 7, pp. 1331-1339, 2007.
Waller et al., "High-Efficiency Lentiviral Genetic Modification of Primary Human Natural Killer Cells," *Blood* vol. 130, Suppl. 1, No. 5566, published online Dec. 7, 2017 (3 pages, Abstract).

(Continued)

Primary Examiner — Antonio Galisteo Gonzalez
(74) Attorney, Agent, or Firm — Klarquist Sparkman, LLP

(57) ABSTRACT

Disclosed herein are method of producing NK cells that include one or more heterologous nucleic acids. The methods include culturing a population of isolated NK cells in the presence of one or more cytokines to produce a population of activated NK cells. The population of activated NK cells are transduced with a viral vector comprising the one or more heterologous nucleic acids, for example by contacting the activated NK cells with viral particles including the viral vector. The resulting transduced NK cells are then cultured in the presence of one or more cytokines, and optionally in the presence of irradiated feeder cells, to produce a population of expanded transduced NK cells. Also disclosed are methods of treating a subject with a disorder (such as a tumor or hyperproliferative disorder) by administering to the subject NK cells produced by the methods described herein.

21 Claims, 23 Drawing Sheets

Specification includes a Sequence Listing.

(56) References Cited

OTHER PUBLICATIONS

Müller et al., "Engineering NK cells modified with an EGFRvIII-specific chimeric antigen receptor to overexpress CXCR4 improves immunotherapy of CXCL12/SDF-1α-secreting glioblastoma," *J. Immunother.*, vol. 38, No. 5, pp. 197-210, 2015 (Author manuscript version, 28 pages).
Zhou et al., "Lentivirus-Mediated Gene Transfer and Expression in Established Human Tumor Antigen-Specific Cytotoxic T Cells and Primary Unstimulated T Cells," *Human Gene Therapy*, vol. 14, pp. 1089-1105, 2003.
Carlsten and Childs, "Genetic manipulation of NK cells for cancer immunotherapy: techniques and clinical implications," *Frontiers in Immunology*, 6:266, 2015 (9 pages).
Childs and Berg, "Bringing natural killer cells to the clinic: ex vivo manipulation," *Hematology 2013: Clinical Production and Applications of Natural Killer Cell Immunotherapy*, pp. 234-246, 2013.
Su et al., "Optimizing Lentiviral Transduction of Human Natural Killer Cells," *Blood*, 118(21): 4714, 2011 (Abstract, 6 pages).
Carotta, "Targeting NK Cells for Anticancer Immunotherapy: Clinical and Preclinical Approaches," *Frontiers in Immunology*, vol. 7, Article 152, 2016 (10 pages).
Norell et al, "CD34-based enrichment of genetically engineered human T cells for clinical use results in dramatically enhanced tumor targeting," *Cancer Immunol Immunother*, vol. 59, pp. 851-862, 2010.
Su et al., "Effective and Stable Gene Transfer into Human NK Cells Using an HIV-1-Based Lentiviral Vector System," *Molecular Therapy*, vol. 16, Supplement 1, pp. S286-S287, 2008.

\* cited by examiner

FIG. 1B
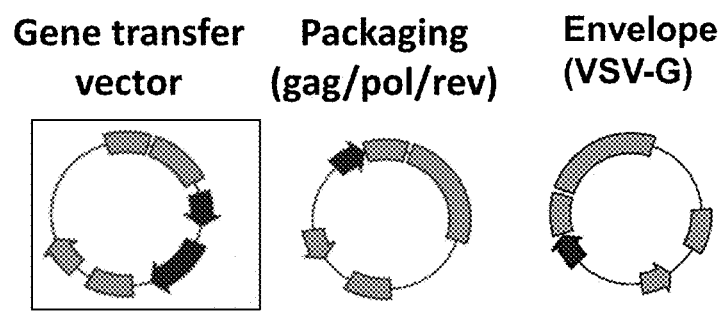
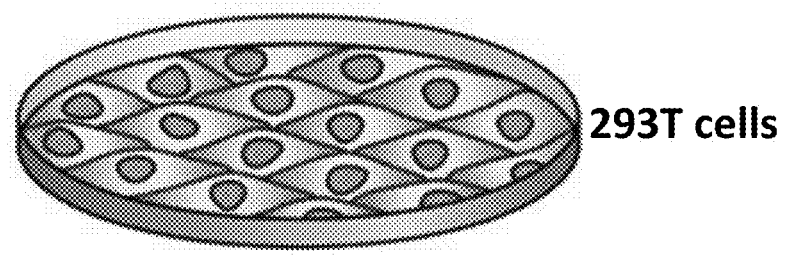
Transfection
293T cells
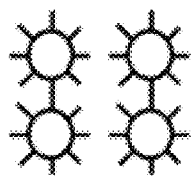
Non-replicating lentivirus
Transduction
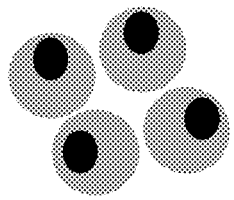

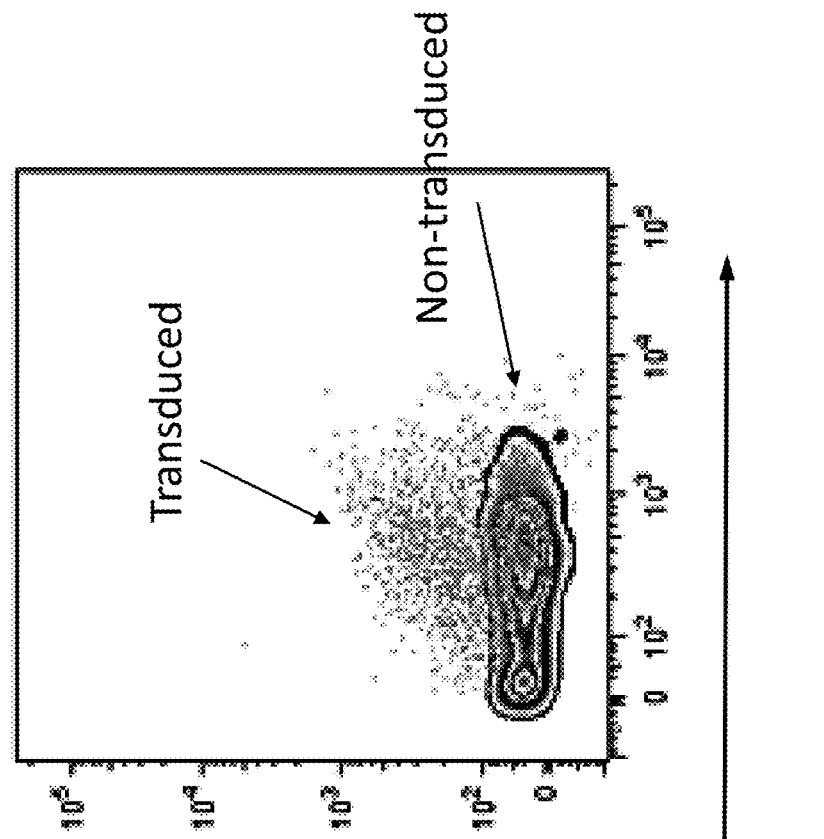
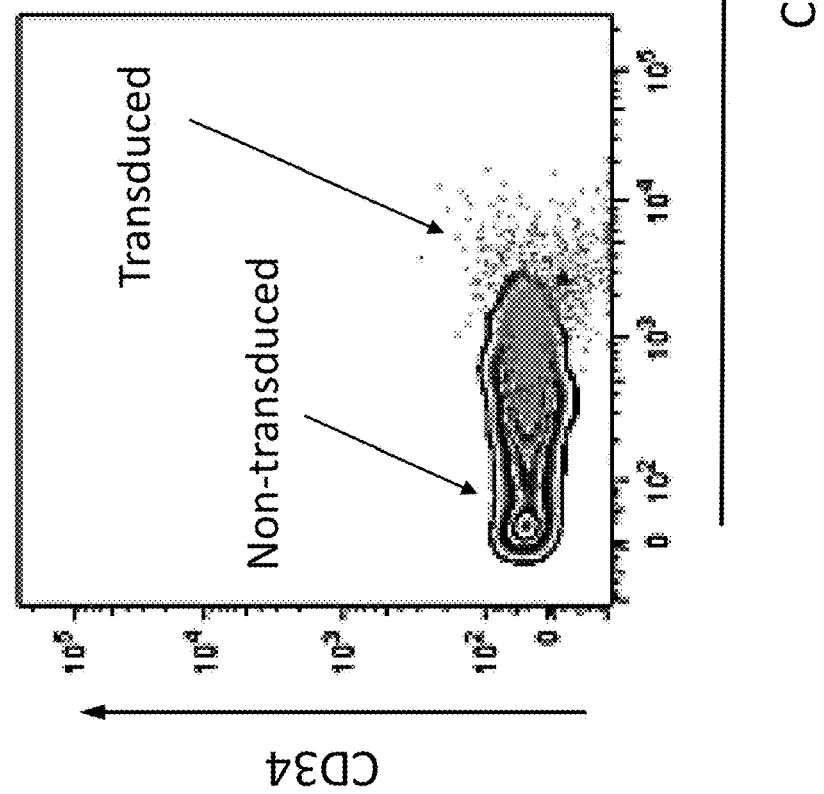

SEQUENCE LISTING

```
<160> NUMBER OF SEQ ID NOS: 17

<210> SEQ ID NO 1
<211> LENGTH: 1059
<212> TYPE: DNA
<213> ORGANISM: Homo sapiens
<220> FEATURE:
<221> NAME/KEY: CDS
<222> LOCATION: (1)..(1059)

<400> SEQUENCE: 1 atg gag ggg atc agt ata tac act tca gat aac tac acc gag gaa atg      48
Met Glu Gly Ile Ser Ile Tyr Thr Ser Asp Asn Tyr Thr Glu Glu Met
1               5                   10                  15 ggc tca ggg gac tat gac tcc atg aag gaa ccc tgt ttc cgt gaa gaa      96
Gly Ser Gly Asp Tyr Asp Ser Met Lys Glu Pro Cys Phe Arg Glu Glu
                20                  25                  30 aat gct aat ttc aat aaa atc ttc ctg ccc acc atc tac tcc atc atc     144
Asn Ala Asn Phe Asn Lys Ile Phe Leu Pro Thr Ile Tyr Ser Ile Ile
            35                  40                  45 ttc tta act ggc att gtg ggc aat gga ttg gtc atc ctg gtc atg ggt     192
Phe Leu Thr Gly Ile Val Gly Asn Gly Leu Val Ile Leu Val Met Gly
        50                  55                  60 tac cag aag aaa ctg aga agc atg acg gac aag tac agg ctg cac ctg     240
Tyr Gln Lys Lys Leu Arg Ser Met Thr Asp Lys Tyr Arg Leu His Leu
65                  70                  75                  80 tca gtg gcc gac ctc ctc ttt gtc atc acg ctt ccc ttc tgg gca gtt     288
Ser Val Ala Asp Leu Leu Phe Val Ile Thr Leu Pro Phe Trp Ala Val
                85                  90                  95 gat gcc gtg gca aac tgg tac ttt ggg aac ttc cta tgc aag gca gtc     336
Asp Ala Val Ala Asn Trp Tyr Phe Gly Asn Phe Leu Cys Lys Ala Val
                100                 105                 110 cat gtc atc tac aca gtc aac ctc tac agc agt gtc ctc atc ctg gcc     384
His Val Ile Tyr Thr Val Asn Leu Tyr Ser Ser Val Leu Ile Leu Ala
            115                 120                 125 ttc atc agt ctg gac cgc tac ctg gcc atc gtc cac gcc acc aac agt     432
Phe Ile Ser Leu Asp Arg Tyr Leu Ala Ile Val His Ala Thr Asn Ser
        130                 135                 140 cag agg cca agg aag ctg ttg gct gaa aag gtg gtc tat gtt ggc gtc     480
Gln Arg Pro Arg Lys Leu Leu Ala Glu Lys Val Val Tyr Val Gly Val
145                 150                 155                 160 tgg atc cct gcc ctc ctg ctg act att ccc gac ttc atc ttt gcc aac     528
Trp Ile Pro Ala Leu Leu Leu Thr Ile Pro Asp Phe Ile Phe Ala Asn
                165                 170                 175
```

```
gtc agt gag gca gat gac aga tat atc tgt gac cgc ttc tac ccc aat    576
Val Ser Glu Ala Asp Asp Arg Tyr Ile Cys Asp Arg Phe Tyr Pro Asn
            180                 185                 190 gac ttg tgg gtg gtt gtg ttc cag ttt cag cac atc atg gtt ggc ctt    624
Asp Leu Trp Val Val Val Phe Gln Phe Gln His Ile Met Val Gly Leu
        195                 200                 205 atc ctg cct ggt att gtc atc ctg tcc tgc tat tgc att atc atc tcc    672
Ile Leu Pro Gly Ile Val Ile Leu Ser Cys Tyr Cys Ile Ile Ile Ser
    210                 215                 220 aag ctg tca cac tcc aag ggc cac cag aag cgc aag gcc ctc aag acc    720
Lys Leu Ser His Ser Lys Gly His Gln Lys Arg Lys Ala Leu Lys Thr
225                 230                 235                 240 aca gtc atc ctc atc ctg gct ttc ttc gcc tgt tgg ctg cct tac tac    768
Thr Val Ile Leu Ile Leu Ala Phe Phe Ala Cys Trp Leu Pro Tyr Tyr
                245                 250                 255 att ggg atc agc atc gac tcc ttc atc ctc ctg gaa atc atc aag caa    816
Ile Gly Ile Ser Ile Asp Ser Phe Ile Leu Leu Glu Ile Ile Lys Gln
            260                 265                 270 ggg tgt gag ttt gag aac act gtg cac aag tgg att tcc atc acc gag    864
Gly Cys Glu Phe Glu Asn Thr Val His Lys Trp Ile Ser Ile Thr Glu
        275                 280                 285 gcc cta gct ttc ttc cac tgt tgt ctg aac ccc atc ctc tat gct ttc    912
Ala Leu Ala Phe Phe His Cys Cys Leu Asn Pro Ile Leu Tyr Ala Phe
    290                 295                 300 ctt gga gcc aaa ttt aaa acc tct gcc cag cac gca ctc acc tct gtg    960
Leu Gly Ala Lys Phe Lys Thr Ser Ala Gln His Ala Leu Thr Ser Val
305                 310                 315                 320 agc aga ggg tcc agc ctc aag atc ctc tcc aaa gga aag cga ggt gga   1008
Ser Arg Gly Ser Ser Leu Lys Ile Leu Ser Lys Gly Lys Arg Gly Gly
                325                 330                 335 cat tca tct gtt tcc act gag tct gag tct tca agt ttt cac tcc agc   1056
His Ser Ser Val Ser Thr Glu Ser Glu Ser Ser Ser Phe His Ser Ser
            340                 345                 350 taa                                                               1059

<210> SEQ ID NO 2
<211> LENGTH: 352
<212> TYPE: PRT
<213> ORGANISM: Homo sapiens

<400> SEQUENCE: 2

Met Glu Gly Ile Ser Ile Tyr Thr Ser Asp Asn Tyr Thr Glu Glu Met
1               5                   10                  15

Gly Ser Gly Asp Tyr Asp Ser Met Lys Glu Pro Cys Phe Arg Glu Glu
            20                  25                  30

Asn Ala Asn Phe Asn Lys Ile Phe Leu Pro Thr Ile Tyr Ser Ile Ile
        35                  40                  45

Phe Leu Thr Gly Ile Val Gly Asn Gly Leu Val Ile Leu Val Met Gly
    50                  55                  60

Tyr Gln Lys Lys Leu Arg Ser Met Thr Asp Lys Tyr Arg Leu His Leu
65                  70                  75                  80

Ser Val Ala Asp Leu Leu Phe Val Ile Thr Leu Pro Phe Trp Ala Val
                85                  90                  95

Asp Ala Val Ala Asn Trp Tyr Phe Gly Asn Phe Leu Cys Lys Ala Val
            100                 105                 110

His Val Ile Tyr Thr Val Asn Leu Tyr Ser Ser Val Leu Ile Leu Ala
        115                 120                 125

Phe Ile Ser Leu Asp Arg Tyr Leu Ala Ile Val His Ala Thr Asn Ser
```

```
            130                 135                 140
Gln Arg Pro Arg Lys Leu Leu Ala Glu Lys Val Val Tyr Val Gly Val
145                 150                 155                 160

Trp Ile Pro Ala Leu Leu Leu Thr Ile Pro Asp Phe Ile Phe Ala Asn
                165                 170                 175

Val Ser Glu Ala Asp Asp Arg Tyr Ile Cys Asp Arg Phe Tyr Pro Asn
            180                 185                 190

Asp Leu Trp Val Val Phe Gln Phe Gln His Ile Met Val Gly Leu
        195                 200                 205

Ile Leu Pro Gly Ile Val Ile Leu Ser Cys Tyr Cys Ile Ile Ile Ser
    210                 215                 220

Lys Leu Ser His Ser Lys Gly His Gln Lys Arg Lys Ala Leu Lys Thr
225                 230                 235                 240

Thr Val Ile Leu Ile Leu Ala Phe Phe Ala Cys Trp Leu Pro Tyr Tyr
                245                 250                 255

Ile Gly Ile Ser Ile Asp Ser Phe Ile Leu Leu Glu Ile Ile Lys Gln
            260                 265                 270

Gly Cys Glu Phe Glu Asn Thr Val His Lys Trp Ile Ser Ile Thr Glu
        275                 280                 285

Ala Leu Ala Phe Phe His Cys Cys Leu Asn Pro Ile Leu Tyr Ala Phe
    290                 295                 300

Leu Gly Ala Lys Phe Lys Thr Ser Ala Gln His Ala Leu Thr Ser Val
305                 310                 315                 320

Ser Arg Gly Ser Ser Leu Lys Ile Leu Ser Lys Gly Lys Arg Gly Gly
                325                 330                 335

His Ser Ser Val Ser Thr Glu Ser Glu Ser Ser Ser Phe His Ser Ser
            340                 345                 350

<210> SEQ ID NO 3
<211> LENGTH: 951
<212> TYPE: DNA
<213> ORGANISM: Homo sapiens
<220> FEATURE:
<221> NAME/KEY: CDS
<222> LOCATION: (1)..(951)

<400> SEQUENCE: 3 atg ccg cgg ggc tgg acc gcg ctt tgc ttg ctg agt ttg ctg cct tct      48
Met Pro Arg Gly Trp Thr Ala Leu Cys Leu Leu Ser Leu Leu Pro Ser
1               5                   10                  15 ggg ttc atg agt ctt gac aac aac ggt act gct acc cca gag tta cct      96
Gly Phe Met Ser Leu Asp Asn Asn Gly Thr Ala Thr Pro Glu Leu Pro
            20                  25                  30 acc cag gga aca ttt tca aat gtt tct aca aat gta tcc tac caa gaa     144
Thr Gln Gly Thr Phe Ser Asn Val Ser Thr Asn Val Ser Tyr Gln Glu
        35                  40                  45 act aca aca cct agt acc ctt gga agt acc agc ctg cac cct gtg tct     192
Thr Thr Thr Pro Ser Thr Leu Gly Ser Thr Ser Leu His Pro Val Ser
    50                  55                  60 caa cat ggc aat gag gcc aca aca aac atc aca gaa acg aca gtc aaa     240
Gln His Gly Asn Glu Ala Thr Thr Asn Ile Thr Glu Thr Thr Val Lys
65                  70                  75                  80 ttc aca tct acc tct gtg ata acc tca gtt tat gga aac aca aac tct     288
Phe Thr Ser Thr Ser Val Ile Thr Ser Val Tyr Gly Asn Thr Asn Ser
                85                  90                  95 tct gtc cag tca cag acc tct gta atc agc aca gtg ttc acc acc cca     336
Ser Val Gln Ser Gln Thr Ser Val Ile Ser Thr Val Phe Thr Thr Pro
            100                 105                 110
```

```
gcc aac gtt tca act cca gag aca acc ttg aag cct agc ctg tca cct    384
Ala Asn Val Ser Thr Pro Glu Thr Thr Leu Lys Pro Ser Leu Ser Pro
            115                 120                 125 gga aat gtt tca gac ctt tca acc act agc act agc ctt gca aca tct    432
Gly Asn Val Ser Asp Leu Ser Thr Thr Ser Thr Ser Leu Ala Thr Ser
130                 135                 140 ccc act aaa ccc tat aca tca tct tct cct atc cta agt gac atc aag    480
Pro Thr Lys Pro Tyr Thr Ser Ser Ser Pro Ile Leu Ser Asp Ile Lys
145                 150                 155                 160 gca gaa atc aaa tgt tca ggc atc aga gaa gtg aaa ttg act cag ggc    528
Ala Glu Ile Lys Cys Ser Gly Ile Arg Glu Val Lys Leu Thr Gln Gly
                165                 170                 175 atc tgc ctg gag caa aat aag acc tcc agc tgt gcg gag ttt aag aag    576
Ile Cys Leu Glu Gln Asn Lys Thr Ser Ser Cys Ala Glu Phe Lys Lys
            180                 185                 190 gac agg gga gag ggc ctg gcc cga gtg ctg tgt ggg gag gag cag gct    624
Asp Arg Gly Glu Gly Leu Ala Arg Val Leu Cys Gly Glu Glu Gln Ala
        195                 200                 205 gat gct gat gct ggg gcc cag gta tgc tcc ctg ctc ctt gcc cag tct    672
Asp Ala Asp Ala Gly Ala Gln Val Cys Ser Leu Leu Leu Ala Gln Ser
210                 215                 220 gag gtg agg cct cag tgt cta ctg ctg gtc ttg gcc aac aga aca gaa    720
Glu Val Arg Pro Gln Cys Leu Leu Leu Val Leu Ala Asn Arg Thr Glu
225                 230                 235                 240 att tcc agc aaa ctc caa ctt atg aaa aag cac caa tct gac ctg aaa    768
Ile Ser Ser Lys Leu Gln Leu Met Lys Lys His Gln Ser Asp Leu Lys
                245                 250                 255 aag ctg ggg atc cta gat ttc act gag caa gat gtt gca agc cac cag    816
Lys Leu Gly Ile Leu Asp Phe Thr Glu Gln Asp Val Ala Ser His Gln
            260                 265                 270 agc tat tcc caa aag acc ctg att gca ctg gtc acc tcg gga gcc ctg    864
Ser Tyr Ser Gln Lys Thr Leu Ile Ala Leu Val Thr Ser Gly Ala Leu
        275                 280                 285 ctg gct gtc ttg ggc atc act ggc tat ttc ctg atg aat cgc cgc agc    912
Leu Ala Val Leu Gly Ile Thr Gly Tyr Phe Leu Met Asn Arg Arg Ser
290                 295                 300 tgg agc ccc aca gga gaa agg ctg gaa cta gaa cca tga                951
Trp Ser Pro Thr Gly Glu Arg Leu Glu Leu Glu Pro
305                 310                 315

<210> SEQ ID NO 4
<211> LENGTH: 316
<212> TYPE: PRT
<213> ORGANISM: Homo sapiens

<400> SEQUENCE: 4

Met Pro Arg Gly Trp Thr Ala Leu Cys Leu Leu Ser Leu Leu Pro Ser
1               5                   10                  15

Gly Phe Met Ser Leu Asp Asn Asn Gly Thr Ala Thr Pro Glu Leu Pro
            20                  25                  30

Thr Gln Gly Thr Phe Ser Asn Val Ser Thr Asn Val Ser Tyr Gln Glu
        35                  40                  45

Thr Thr Thr Pro Ser Thr Leu Gly Ser Thr Ser Leu His Pro Val Ser
    50                  55                  60

Gln His Gly Asn Glu Ala Thr Thr Asn Ile Thr Glu Thr Thr Val Lys
65                  70                  75                  80

Phe Thr Ser Thr Ser Val Ile Thr Ser Val Tyr Gly Asn Thr Asn Ser
                85                  90                  95
```

```
Ser Val Gln Ser Gln Thr Ser Val Ile Ser Thr Val Phe Thr Thr Pro
            100                 105                 110

Ala Asn Val Ser Thr Pro Glu Thr Thr Leu Lys Pro Ser Leu Ser Pro
        115                 120                 125

Gly Asn Val Ser Asp Leu Ser Thr Thr Ser Thr Ser Leu Ala Thr Ser
    130                 135                 140

Pro Thr Lys Pro Tyr Thr Ser Ser Pro Ile Leu Ser Asp Ile Lys
145                 150                 155                 160

Ala Glu Ile Lys Cys Ser Gly Ile Arg Glu Val Lys Leu Thr Gln Gly
                165                 170                 175

Ile Cys Leu Glu Gln Asn Lys Thr Ser Ser Cys Ala Glu Phe Lys Lys
            180                 185                 190

Asp Arg Gly Glu Gly Leu Ala Arg Val Leu Cys Gly Glu Glu Gln Ala
        195                 200                 205

Asp Ala Asp Ala Gly Ala Gln Val Cys Ser Leu Leu Leu Ala Gln Ser
    210                 215                 220

Glu Val Arg Pro Gln Cys Leu Leu Val Leu Ala Asn Arg Thr Glu
225                 230                 235                 240

Ile Ser Ser Lys Leu Gln Leu Met Lys Lys His Gln Ser Asp Leu Lys
                245                 250                 255

Lys Leu Gly Ile Leu Asp Phe Thr Glu Gln Asp Val Ala Ser His Gln
            260                 265                 270

Ser Tyr Ser Gln Lys Thr Leu Ile Ala Leu Val Thr Ser Gly Ala Leu
        275                 280                 285

Leu Ala Val Leu Gly Ile Thr Gly Tyr Phe Leu Met Asn Arg Arg Ser
    290                 295                 300

Trp Ser Pro Thr Gly Glu Arg Leu Glu Leu Glu Pro
305                 310                 315

<210> SEQ ID NO 5
<211> LENGTH: 765
<212> TYPE: DNA
<213> ORGANISM: Homo sapiens
<220> FEATURE:
<221> NAME/KEY: CDS
<222> LOCATION: (1)..(765)

<400> SEQUENCE: 5 atg tgg cag ctg ctc ctc cca act gct ctg cta ctt cta gtt tca gct      48
Met Trp Gln Leu Leu Leu Pro Thr Ala Leu Leu Leu Leu Val Ser Ala
1               5                   10                  15 ggc atg cgg act gaa gat ctc cca aag gct gtg gtg ttc ctg gag cct      96
Gly Met Arg Thr Glu Asp Leu Pro Lys Ala Val Val Phe Leu Glu Pro
            20                  25                  30 caa tgg tac agg gtg ctc gag aag gac agt gtg act ctg aag tgc cag     144
Gln Trp Tyr Arg Val Leu Glu Lys Asp Ser Val Thr Leu Lys Cys Gln
        35                  40                  45 gga gcc tac tcc cct gag gac aat tcc aca cag tgg ttt cac aat gag     192
Gly Ala Tyr Ser Pro Glu Asp Asn Ser Thr Gln Trp Phe His Asn Glu
    50                  55                  60 agc ctc atc tca agc cag gcc tcg agc tac ttc att gac gct gcc aca     240
Ser Leu Ile Ser Ser Gln Ala Ser Ser Tyr Phe Ile Asp Ala Ala Thr
65                  70                  75                  80 gtt gac gac agt gga gag tac agg tgc cag aca aac ctc tcc acc ctc     288
Val Asp Asp Ser Gly Glu Tyr Arg Cys Gln Thr Asn Leu Ser Thr Leu
                85                  90                  95 agt gac ccg gtg cag cta gaa gtc cat atc ggc tgg ctg ttg ctc cag     336
Ser Asp Pro Val Gln Leu Glu Val His Ile Gly Trp Leu Leu Leu Gln
```

|     |     |
| --- | --- |
| gcc cct cgg tgg gtg ttc aag gag gaa gac cct att cac ctg agg tgt<br>Ala Pro Arg Trp Val Phe Lys Glu Glu Asp Pro Ile His Leu Arg Cys<br>     115                         120                        125 | 384 |
| cac agc tgg aag aac act gct ctg cat aag gtc aca tat tta cag aat<br>His Ser Trp Lys Asn Thr Ala Leu His Lys Val Thr Tyr Leu Gln Asn<br>     130                         135                        140 | 432 |
| ggc aaa ggc agg aag tat ttt cat cat aat tct gac ttc tac att cca<br>Gly Lys Gly Arg Lys Tyr Phe His His Asn Ser Asp Phe Tyr Ile Pro<br>145                       150                        155                        160 | 480 |
| aaa gcc aca ctc aaa gac agc ggc tcc tac ttc tgc agg ggg ctt gtt<br>Lys Ala Thr Leu Lys Asp Ser Gly Ser Tyr Phe Cys Arg Gly Leu Val<br>               165                        170                        175 | 528 |
| ggg agt aaa aat gtg tct tca gag act gtg aac atc acc atc act caa<br>Gly Ser Lys Asn Val Ser Ser Glu Thr Val Asn Ile Thr Ile Thr Gln<br>     180                         185                        190 | 576 |
| ggt ttg gca gtg tca acc atc tca tca ttc ttt cca cct ggg tac caa<br>Gly Leu Ala Val Ser Thr Ile Ser Ser Phe Phe Pro Pro Gly Tyr Gln<br>               195                        200 | 624 |
| gtc tct ttc tgc ttg gtg atg gta ctc ctt ttt gca gtg gac aca gga<br>Val Ser Phe Cys Leu Val Met Val Leu Leu Phe Ala Val Asp Thr Gly<br>     210                         215                        220 | 672 |
| cta tat ttc tct gtg aag aca aac att cga agc tca aca aga gac tgg<br>Leu Tyr Phe Ser Val Lys Thr Asn Ile Arg Ser Ser Thr Arg Asp Trp<br>225                       230                        235                        240 | 720 |
| aag gac cat aaa ttt aaa tgg aga aag gac cct caa gac aaa tga<br>Lys Asp His Lys Phe Lys Trp Arg Lys Asp Pro Gln Asp Lys<br>               245                        250 | 765 |

<210> SEQ ID NO 6
<211> LENGTH: 254
<212> TYPE: PRT
<213> ORGANISM: Homo sapiens

<400> SEQUENCE: 6

Met Trp Gln Leu Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Phe Pro Pro Gly Tyr Gln
            195                 200                 205

Val Ser Phe Cys Leu Val Met Val Leu Leu Phe Ala Val Asp Thr Gly
            210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
            245                 250

<210> SEQ ID NO 7
<211> LENGTH: 765
<212> TYPE: DNA
<213> ORGANISM: Artificial Sequence
<220> FEATURE:
<223> OTHER INFORMATION: Codon-optimized high affinity CD16

<400> SEQUENCE: 7
atgtggcagc tgctgctgcc aaccgccctg ctgctgctgg tgtccgccgg aatgaggaca      60
gaggacctgc caaaggccgt ggtgtttctg gagccccagt ggtacagagt gctggagaag     120
gactctgtga ccctgaagtg ccagggcgcc tattctcctg aggataacag cacacagtgg     180
tttcacaatg agagcctgat cagctcccag gcctctagct acttcatcga cgcagcaacc     240
gtggacgatt ccggagagta tcggtgccag accaacctga gcacactgtc cgatccagtg     300
cagctggagg tgcacatcgg atggctgctg ctgcaggcac ctagatgggt gtttaaggag     360
gaggacccca tccacctgcg ctgtcacagc tggaagaata ccgccctgca aggtgaca       420 tacctgcaga cggcaaggg caggaagtac ttccaccaca attctgactt ttatatcccc      480
aaggccaccc tgaaggattc cggctcttat ttctgccgcg gcctggtggg cagcaagaac     540
gtgtcctctg agaccgtgaa atcaccatc acacagggcc tggccgtgtc cacaatcagc      600
tccttctttc cccctggcta ccaggtgtct ttctgtctgg tcatggtgct gctgtttgcc     660
gtggacacag cctgtatttt ctccgtgaag accaacatcc ggtctagcac aagagactgg     720
aaggatcaca gttcaagtg gcggaaggac cctcaggata gtga                       765

<210> SEQ ID NO 8
<211> LENGTH: 7495
<212> TYPE: DNA
<213> ORGANISM: Artificial Sequence
<220> FEATURE:
<223> OTHER INFORMATION: Synthetic lentiviral vector

<400> SEQUENCE: 8
aatgtagtct tatgcaatac tcttgtagtc ttgcaacatg gtaacgatga gttagcaaca      60
tgccttacaa ggagagaaaa agcaccgtgc atgccgattg gtggaagtaa ggtggtacga     120
tcgtgcctta ttaggaaggc aacagacggg tctgacatgg attggacgaa ccactgaatt     180
gccgcattgc agagatattg tatttaagtg cctagctcga tacataaacg gtctctctg      240 gttagaccag atctgagcct gggagctctc tggctaacta gggaacccac tgcttaagcc     300
tcaataaagc ttgccttgag tgcttcaagt agtgtgtgcc cgtctgttgt gtgactctgg     360
taactagaga tccctcagac ccttttagtc agtgtggaaa atctctagca gtggcgcccg     420
aacagggact tgaaagcgaa agggaaacca gaggagctct ctcgacgcag gactcggctt     480
gctgaagcgc gcacggcaag aggcgagggg cggcgactgg tgagtacgcc aaaaattttg     540

```
actagcggag gctagaagga gagagatggg tgcgagagcg tcagtattaa gcggggggaga    600 attagatcgc gatgggaaaa aattcggtta aggccagggg gaaagaaaaa atataaatta    660
aaacatatag tatgggcaag cagggagcta gaacgattcg cagttaatcc tggcctgtta    720
gaaacatcag aaggctgtag acaaatactg ggacagctac aaccatccct tcagacagga    780
tcagaagaac ttagatcatt ataataaca gtagcaaccc tctattgtgt gcatcaaagg    840
atagagataa aagacaccaa ggaagcttta gacaagatag aggaagagca aaacaaaagt    900
aagaccaccg cacagcaagc ggccgctgat cttcagacct ggaggaggag atatgaggga    960
caattggaga agtgaattat ataaatataa agtagtaaaa attgaaccat taggagtagc   1020
acccaccaag gcaaagagaa gagtggtgca gagagaaaaa agagcagtgg gaataggagc   1080
tttgttcctt gggttcttgg gagcagcagg aagcactatg ggcgcagcgt caatgacgct   1140
gacggtacag gccagacaat tattgtctgg tatagtgcag cagcagaaca atttgctgag   1200
ggctattgag gcgcaacagc atctgttgca actcacagtc tggggcatca agcagctcca   1260
ggcaagaatc ctggctgtgg aaagatacct aaaggatcaa cagctcctgg ggatttgggg   1320
ttgctctgga aaactcattt gcaccactgc tgtgccttgg aatgctagtt ggagtaataa   1380
atctctggaa cagatttgga atcacacgac ctggatggag tgggacagag aaattaacaa   1440
ttacacaagc ttaatacact ccttaattga agaatcgcaa aaccagcaag aaagaatga    1500 acaagaatta ttggaattag ataaatgggc aagtttgtgg aattggttta acataacaaa   1560
ttggctgtgg tatataaaat tattcataat gatagtagga ggcttggtag gtttaagaat   1620
agtttttgct gtactttcta tagtgaatag agttaggcag ggatattcac cattatcgtt   1680
tcagacccac ctcccaaccc cgaggggacc cgacaggccc gaaggaatag aagaagaagg   1740
tggagagaga gacagagaca gatccattcg attagtgaac ggatctcgac ggtatcgcta   1800
gcttttaaaa gaaaagggggg gattgggggg tacagtgcag gggaagaat agtagacata   1860 atagcaacag acatacaaac taagaatta caaaaacaaa ttacaaaaat tcaaaatttt   1920
actagtgatt atcggatcaa ctttgtatag aaaagttgta gttattaata gtaatcaatt   1980
acggggtcat tagttcatag cccatatatg gagttccgcg ttacataact tacggtaaat   2040
ggcccgcctg gctgaccgcc caacgacccc cgcccattga cgtcaataat gacgtatgtt   2100
cccatagtaa cgccaatagg gactttccat tgacgtcaat gggtggagta tttacggtaa   2160
actgcccact tggcagtaca tcaagtgtat catatgccaa gtacgccccc tattgacgtc   2220
aatgacggta aatggcccgc ctggcattat gcccagtaca tgaccttatg gactttcct   2280 acttggcagt acatctacgt attagtcatc gctattacca tggtgatgcg gttttggcag   2340
tacatcaatg ggcgtggata gcggtttgac tcacggggat ttccaagtct ccaccccatt   2400
gacgtcaatg ggagtttgtt ttggcaccaa aatcaacggg actttccaaa atgtcgtaac   2460
aactccgccc cattgacgca aatgggcggt aggcgtgtac ggtgggaggt ctatataagc   2520
agagctggtt tagtgaaccg tcagatccaa gtttgtacaa aaaagcaggc tgccaccatg   2580
gtgagcaagg gcgaggagct gttcaccggg gtggtgccca tcctggtcga gctggacggc   2640
gacgtaaacg gccacaagtt cagcgtgtcc ggcgagggcg agggcgatgc cacctacggc   2700
aagctgaccc tgaagttcat ctgcaccacc ggcaagctgc ccgtgccctg cccacccctc   2760
gtgaccaccc tgacctacgg cgtgcagtgc ttcagccgct accccgacca catgaagcag   2820
cacgacttct tcaagtccgc catgcccgaa ggctacgtcc aggagcgcac catcttcttc   2880
aaggacgacg gcaactacaa gacccgcgcc gaggtgaagt tcgagggcga caccctggtg   2940
```

```
aaccgcatcg agctgaaggg catcgacttc aaggaggacg gcaacatcct ggggcacaag    3000
ctggagtaca actacaacag ccacaacgtc tatatcatgg ccgacaagca gaagaacggc    3060
atcaaggtga acttcaagat ccgccacaac atcgaggacg gcagcgtgca gctcgccgac    3120
cactaccagc agaacacccc catcggcgac ggccccgtgc tgctgcccga caaccactac    3180
ctgagcaccc agtccgccct gagcaaagac cccaacgaga gcgcgatca catggtcctg     3240 ctggagttcg tgaccgccgc cgggatcact ctcggcatgg acgagctgta caagtaaacc    3300
cagctttctt gtacaaagtg gtgataatcg aattccgata atcaacctct ggattacaaa    3360
atttgtgaaa gattgactgg tattcttaac tatgttgctc cttttacgct atgtggatac    3420
gctgctttaa tgcctttgta tcatgctatt gcttcccgta tggctttcat tttctcctcc    3480
ttgtataaat cctggttgct gtctctttat gaggagttgt ggcccgttgt caggcaacgt    3540
ggcgtggtgt gcactgtgtt tgctgacgca accccactg gttggggcat tgccaccacc    3600
tgtcagctcc tttccgggac tttgcttttc ccctcccta ttgccacggc ggaactcatc     3660
gccgcctgcc ttgcccgctg ctggacaggg gctcggctgt tgggcactga caattccgtg    3720
gtgttgtcgg ggaagctgac gtccttcca tggctgctcg cctgtgttgc cacctggatt     3780
ctgcgcggga cgtccttctg ctacgtccct tcggccctca atccagcgga ccttccttcc    3840
cgcggcctgc tgccggctct gcggcctctt ccgcgtcttc gccttcgccc tcagacgagt    3900
cggatctccc tttgggccgc ctccccgcat cgggaattcc cgcggttcgc tttaagacca    3960
atgacttaca aggcagctgt agatcttagc cactttttaa aagaaaaggg gggactggaa    4020
gggctaattc actcccaacg aagacaagat ctgctttttg cttgtactgg gtctctctgg    4080
ttagaccaga tctgagcctg ggagctctct ggctaactag gaacccact gcttaagcct     4140 caataaagct tgccttgagt gcttcaagta gtgtgtgccc gtctgttgtg tgactctggt    4200
aactagagat ccctcagacc cttttagtca gtgtggaaaa tctctagcag tagtagttca    4260
tgtcatctta ttattcagta tttataactt gcaaagaaat gaatatcaga gagtgagagg    4320
aacttgttta ttgcagctta taatggttac aaataaagca atagcatcac aaatttcaca    4380
aataaagcat ttttttcact gcattctagt tgtggtttgt ccaaactcat caatgtatct    4440
tatcatgtct ggctctagct atcccgcccc taactccgcc catcccgccc ctaactccgc    4500
ccagttccgc ccattctccg ccccatggct gactaatttt ttttatttat gcagaggccg    4560
aggccgcctc ggcctctgag ctattccaga agtagtgagg aggctttttt ggaggcctag    4620
ggacgtaccc aattcgccct atagtgagtc gtattacgcg cgctcactgg ccgtcgtttt    4680
acaacgtcgt gactgggaaa accctggcgt tacccaactt aatcgccttg cagcacatcc    4740
ccctttcgcc agctggcgta atagcgaaga ggcccgcacc gatcgccctt cccaacagtt    4800
gcgcagcctg aatggcgaat gggacgcgcc ctgtagcggc gcattaagcg cggcgggtgt    4860
ggtggttacg cgcagcgtga ccgctacact tgccagcgcc ctagcgcccg ctcctttcgc    4920
tttcttccct tcctttctcg ccacgttcgc cggctttccc cgtcaagctc taaatcgggg    4980
gctcccttta gggttccgat ttagtgcttt acggcacctc gaccccaaaa aacttgatta    5040
gggtgatggt tcacgtagtg gccatcgccc tgatagacg gtttttcgcc ctttgacgtt    5100
ggagtccacg ttctttaata gtggactctt gttccaaact ggaacaacac tcaaccctat    5160
ctcggtctat tcttttgatt tataagggat tttgccgatt tcggcctatt ggttaaaaaa    5220
tgagctgatt taacaaaaat ttaacgcgaa ttttaacaaa atattaacgc ttacaattta    5280
```

```
ggtggcactt ttcggggaaa tgtgcgcgga accccctattt gtttattttt ctaaatacat    5340
tcaaatatgt atccgctcat gagacaataa ccctgataaa tgcttcaata atattgaaaa    5400
aggaagagta tgagtattca acatttccgt gtcgccctta ttccctttttt tgcggcattt    5460 tgccttcctg ttttttgctca cccagaaacg ctggtgaaag taaaagatgc tgaagatcag    5520
ttgggtgcac gagtgggtta catcgaactg gatctcaaca gcggtaagat ccttgagagt    5580
tttcgccccg aagaacgttt tccaatgatg agcacttttta aagttctgct atgtggcgcg    5640
gtattatccc gtattgacgc cgggcaagag caactcggtc gccgcataca ctattctcag    5700
aatgacttgg ttgagtactc accagtcaca gaaaagcatc ttacgatgg catgacagta    5760 agagaattat gcagtgctgc cataaccatg agtgataaca ctgcggccaa cttacttctg    5820
acaacgatcg gaggaccgaa ggagctaacc gcttttttgc acaacatggg ggatcatgta    5880
actcgccttg atcgttggga accggagctg aatgaagcca taccaaacga cgagcgtgac    5940
accacgatgc ctgtagcaat ggcaacaacg ttgcgcaaac tattaactgg cgaactactt    6000
actctagctt cccggcaaca attaatagac tggatggagg cggataaagt tgcaggacca    6060
cttctgcgct cggcccttcc ggctggctgg tttattgctg ataaatctgg agccggtgag    6120
cgtgggtctc gcggtatcat tgcagcactg gggccagatg gtaagccctc ccgtatcgta    6180
gttatctaca cgacggggag tcaggcaact atggatgaac gaaatagaca gatcgctgag    6240
ataggtgcct cactgattaa gcattggtaa ctgtcagacc aagtttactc atatatactt    6300
tagattgatt taaaacttca tttttaattt aaaaggatct aggtgaagat cctttttgat    6360
aatctcatga ccaaaatccc ttaacgtgag ttttcgttcc actgagcgtc agaccccgta    6420
gaaaagatca aaggatcttc ttgagatcct ttttttctgc gcgtaatctg ctgcttgcaa    6480
acaaaaaaac caccgctacc agcggtggtt tgtttgccgg atcaagagct accaactctt    6540
tttccgaagg taactggctt cagcagagcg cagataccaa atactgttct tctagtgtag    6600
ccgtagttag gccaccactt caagaactct gtagcaccgc ctacatacct cgctctgcta    6660
atcctgttac cagtggctgc tgccagtggc gataagtcgt gtcttaccgg gttggactca    6720
agacgatagt taccggataa ggcgcagcgg tcgggctgaa cggggggttc gtgcacacag    6780
cccagcttgg agcgaacgac ctacaccgaa ctgagatacc tacagcgtga gctatgagaa    6840
agcgccacgc ttcccgaaga gagaaaggcg gacaggtatc cggtaagcgg cagggtcgga    6900
acaggagagc gcacgaggga gcttccaggg ggaaacgcct ggtatcttta tagtcctgtc    6960
gggtttcgcc acctctgact tgagcgtcga ttttttgtgat gctcgtcagg ggggcggagc    7020
ctatggaaaa acgccagcaa cgcggccttt ttacggttcc tggccttttg ctggccttt    7080 gctcacatgt tctttcctgc gttatcccct gattctgtgg ataaccgtat taccgccttt    7140
gagtgagctg ataccgctcg ccgcagccga acgaccgagc gcagcgagtc agtgagcgag    7200
gaagcggaag agcgcccaat acgcaaaccg cctctccccg cgcgttggcc gattcattaa    7260
tgcagctggc acgacaggtt tcccgactgg aaagcgggca gtgagcgcaa cgcaattaat    7320
gtgagttagc tcactcatta ggcaccccag gctttacact ttatgcttcc ggctcgtatg    7380
ttgtgtggaa ttgtgagcgg ataacaattt cacacaggaa acagctatga ccatgattac    7440
gccaagcgcg caattaaccc tcactaaagg gaacaaaagc tggagctgca agctt          7495
```

<210> SEQ ID NO 9
<211> LENGTH: 8085
<212> TYPE: DNA
<213> ORGANISM: Artificial Sequence
<220> FEATURE:
<223> OTHER INFORMATION: Synthetic lentiviral vector

<400> SEQUENCE: 9

```
aatgtagtct tatgcaatac tcttgtagtc ttgcaacatg gtaacgatga gttagcaaca      60
tgccttacaa ggagagaaaa agcaccgtgc atgccgattg gtggaagtaa ggtggtacga     120
tcgtgcctta ttaggaaggc aacagacggg tctgacatgg attggacgaa ccactgaatt     180
gccgcattgc agagatattg tatttaagtg cctagctcga tacataaacg ggtctctctg     240
gttagaccag atctgagcct gggagctctc tggctaacta gggaacccac tgcttaagcc     300
tcaataaagc ttgccttgag tgcttcaagt agtgtgtgcc cgtctgttgt gtgactctgg     360
taactagaga tccctcagac ccttttagtc agtgtggaaa atctctagca gtggcgcccg     420
aacagggact tgaaagcgaa agggaaacca gaggagctct ctcgacgcag gactcggctt     480
gctgaagcgc gcacggcaag aggcgagggg cggcgactgg tgagtacgcc aaaaattttg     540
actagcggag gctagaagga gagagatggg tgcgagagcg tcagtattaa gcggggagaa     600
attagatcgc gatgggaaaa aattcggtta aggccagggg gaaagaaaaa atataaatta     660
aaacatatag tatgggcaag cagggagcta gaacgattcg cagttaatcc tggcctgtta     720
gaaacatcag aaggctgtag acaaatactg ggacagctac aaccatccct tcagacagga     780
tcagaagaac ttagatcatt atataataca gtagcaaccc tctattgtgt gcatcaaagg     840
atagagataa aagacaccaa ggaagcttta gacaagatag aggaagagca aaacaaaagt     900
aagaccaccg cacagcaagc ggccgctgat cttcagacct ggaggaggag atatgaggga     960
caattggaga agtgaattat ataaatataa agtagtaaaa attgaaccat taggagtagc    1020
acccaccaag gcaaagagaa gagtggtgca gagagaaaaa agagcagtgg gaataggagc    1080
tttgttcctt gggttcttgg gagcagcagg aagcactatg ggcgcagcgt caatgacgct    1140
gacggtacag gccagacaat tattgtctgg tatagtgcag cagcagaaca atttgctgag    1200
ggctattgag gcgcaacagc atctgttgca actcacagtc tggggcatca agcagctcca    1260
ggcaagaatc ctggctgtgg aaagatacct aaaggatcaa cagctcctgg ggatttgggg    1320
ttgctctgga aaactcattt gcaccactgc tgtgccttgg aatgctagtt ggagtaataa    1380
atctctggaa cagatttgga atcacacgac ctggatggag tgggacagag aaattaacaa    1440
ttacacaagc ttaatacact ccttaattga agaatcgcaa aaccagcaag aaaagaatga    1500
acaagaatta ttggaattag ataaatgggc aagtttgtgg aattggttta acataacaaa    1560
ttggctgtgg tatataaaat tattcataat gatagtagga ggcttggtag gtttaagaat    1620
agtttttgct gtactttcta tagtgaatag agttaggcag ggatattcac cattatcgtt    1680
tcagacccac ctcccaaccc cgaggggacc cgacaggccc gaaggaatag aagaagaagg    1740
tggagagaga gacagagaca gatccattcg attagtgaac ggatctcgac ggtatcgcta    1800
gcttttaaaa gaaaaggggg gattgggggg tacagtgcag gggaaagaat agtagacata    1860
atagcaacag acatacaaac taagaatta caaaaacaaa ttacaaaaat tcaaaatttt    1920
actagtgatt atcggatcaa ctttgtatag aaaagttggg ctccggtgcc cgtcagtggg    1980
cagagcgcac atcgcccaca gtccccgaga agttggggg aggggtcggc aattgaaccg    2040
gtgcctagag aaggtggcgc ggggtaaact gggaaagtga tgtcgtgtac tggctccgcc    2100
tttttcccga gggtggggga gaaccgtata taagtgcagt agtcgccgtg aacgttcttt    2160
ttcgcaacgg gtttgccgcc agaacacagg taagtgccgt gtgtggttcc cgcgggcctg    2220
```

```
gcctctttac gggttatggc ccttgcgtgc cttgaattac ttccacctgg ctgcagtacg    2280
tgattcttga tcccgagctt cgggttggaa gtgggtggga gagttcgagg ccttgcgctt    2340
aaggagcccc ttcgcctcgt gcttgagttg aggcctggcc tgggcgctgg ggccgccgcg    2400
tgcgaatctg gtggcacctt cgcgcctgtc tcgctgcttt cgataagtct ctagccattt    2460 aaaattttg atgacctgct gcgacgcttt ttttctggca agatagtctt gtaaatgcgg    2520
gccaagatct gcacactggt atttcggttt ttggggccgc gggcggcgac ggggcccgtg    2580
cgtcccagcg cacatgttcg gcgaggcggg gcctgcgagc gcggccaccg agaatcggac    2640
gggggtagtc tcaagctggc cggcctgctc tggtgcctgg tctcgcgccc ccgtgtatcg    2700
ccccgccctg ggcggcaagg ctggcccggt cggcaccagt tgcgtgagcg aaagatggc     2760 cgcttcccgg ccctgctgca gggagctcaa aatggaggac gcggcgctcg ggagagcggg    2820
cgggtgagtc acccacacaa aggaaaaggg cctttccgtc ctcagccgtc gcttcatgtg    2880
actccacgga gtaccgggcg ccgtccaggc acctcgatta gttctcgagc ttttggagta    2940
cgtcgtcttt aggttggggg gaggggtttt atgcgatgga gtttccccac actgagtggg    3000
tggagactga agttaggcca gcttggcact tgatgtaatt ctccttggaa tttgcccttt    3060
ttgagtttgg atcttggttc attctcaagc ctcagacagg ggttcaaagt ttttttcttc    3120
catttcaggt gtcgtgacaa gtttgtacaa aaaagcaggc tgccaccatg gtgagcaagg    3180
gcgaggagct gttcaccggg gtggtgccca tcctggtcga gctggacggc gacgtaaacg    3240
gccacaagtt cagcgtgtcc ggcgagggcg agggcgatgc cacctacggc aagctgaccc    3300
tgaagttcat ctgcaccacc ggcaagctgc cgtgccctg gcccaccctc gtgaccaccc     3360
tgacctacgg cgtgcagtgc ttcagccgct accccgacca catgaagcag cacgacttct    3420
tcaagtccgc catgcccgaa ggctacgtcc aggagcgcac catcttcttc aaggacgacg    3480
gcaactacaa gacccgcgcc gaggtgaagt tcgagggcga caccctggtg aaccgcatcg    3540
agctgaaggg catcgacttc aaggaggacg gcaacatcct ggggcacaag ctggagtaca    3600
actacaacag ccacaacgtc tatatcatgg ccgacaagca gaagaacggc atcaaggtga    3660
acttcaagat ccgccacaac atcgaggacg gcagcgtgca gctcgccgac cactaccagc    3720
agaacacccc catcggcgac ggccccgtgc tgctgcccga caaccactac ctgagcaccc    3780
agtccgccct gagcaaagac cccaacgaga gcgcgatca catggtcctg ctggagttcg    3840
tgaccgccgc cgggatcact ctcggcatgg acgagctgta caagtaaacc cagctttctt    3900
gtacaaagtg gtgataatcg aattccgata atcaacctct ggattacaaa atttgtgaaa    3960
gattgactgg tattcttaac tatgttgctc cttttacgct atgtggatac gctgctttaa    4020
tgcctttgta tcatgctatt gcttcccgta tggctttcat tttctcctcc ttgtataaat    4080
cctggttgct gtctctttat gaggagttgt ggcccgttgt caggcaacgt ggcgtggtgt    4140
gcactgtgtt tgctgacgca acccccactg gttgggcat tgccaccacc tgtcagctcc    4200
tttccgggac tttcgctttc cccctcccta ttgccacggc ggaactcatc gccgcctgcc    4260
ttgcccgctg ctggacaggg gctcggctgt tgggcactga caattccgtg tgttgtcgg    4320 ggaagctgac gtcctttcca tggctgctcg cctgtgttgc cacctggatt ctgcgcggga    4380
cgtccttctg ctacgtccct tcggccctca atccagcgga ccttccttcc cgcggcctgc    4440
tgccggctct gcggcctctt ccgcgtcttc gccttcgccc tcagacgagt cggatctccc    4500
tttgggccgc ctccccgcat cgggaattcc cgcggttcgc tttaagacca atgacttaca    4560
aggcagctgt agatcttagc cacttttta aagaaaaggg gggactggaa gggctaattc     4620
```

```
actcccaacg aagacaagat ctgctttttg cttgtactgg gtctctctgg ttagaccaga    4680
tctgagcctg ggagctctct ggctaactag ggaacccact gcttaagcct caataaagct    4740
tgccttgagt gcttcaagta gtgtgtgccc gtctgttgtg tgactctggt aactagagat    4800
ccctcagacc cttttagtca gtgtggaaaa tctctagcag tagtagttca tgtcatctta    4860
ttattcagta tttataactt gcaaagaaat gaatatcaga gagtgagagg aacttgttta    4920
ttgcagctta taatggttac aaataaagca atagcatcac aaatttcaca aataaagcat    4980 tttttttcact gcattctagt tgtggtttgt ccaaactcat caatgtatct tatcatgtct    5040
ggctctagct atcccgcccc taactccgcc catcccgccc ctaactccgc ccagttccgc    5100
ccattctccg ccccatggct gactaatttt ttttatttat gcagaggccg aggccgcctc    5160
ggcctctgag ctattccaga agtagtgagg aggcttttt ggaggcctag ggacgtaccc    5220
aattcgccct atagtgagtc gtattacgcg cgctcactgg ccgtcgtttt acaacgtcgt    5280
gactgggaaa accctggcgt tacccaactt aatcgccttg cagcacatcc cctttcgcc    5340 agctggcgta atagcgaaga ggcccgcacc gatcgccctt cccaacagtt gcgcagcctg    5400
aatggcgaat gggacgcgcc ctgtagcggc gcattaagcg cggcgggtgt ggtggttacg    5460
cgcagcgtga ccgctacact tgccagcgcc ctagcgcccg ctcctttcgc tttcttccct    5520
tcctttctcg ccacgttcgc cggctttccc cgtcaagctc taaatcgggg gctcccttta    5580
gggttccgat ttagtgcttt acggcacctc gaccccaaaa aacttgatta gggtgatggt    5640
tcacgtagtg ggccatcgcc ctgatagacg gtttttcgcc ctttgacgtt ggagtccacg    5700
ttctttaata gtggactctt gttccaaact ggaacaacac tcaaccctat ctcggtctat    5760
tcttttgatt tataagggat tttgccgatt tcggcctatt ggttaaaaaa tgagctgatt    5820
taacaaaaat ttaacgcgaa ttttaacaaa atattaacgc ttacaattta ggtggcactt    5880
ttcggggaaa tgtgcgcgga acccctattt gtttatttt ctaaatacat tcaaatatgt    5940
atccgctcat gagacaataa ccctgataaa tgcttcaata atattgaaaa aggaagagta    6000
tgagtattca acatttccgt gtcgccctta ttcccttttt tgcggcattt tgccttcctg    6060
tttttgctca cccagaaacg ctggtgaaag taaaagatgc tgaagatcag ttgggtgcac    6120
gagtgggtta catcgaactg gatctcaaca gcggtaagat ccttgagagt tttcgccccg    6180
aagaacgttt tccaatgatg agcactttta aagttctgct atgtggcgcg gtattatccc    6240
gtattgacgc cgggcaagag caactcggtc gccgcataca ctattctcag aatgacttgg    6300
ttgagtactc accagtcaca gaaaagcatc ttacggatgg catgacagta agagaattat    6360
gcagtgctgc cataaccatg agtgataaca ctgcggccaa cttacttctg acaacgatcg    6420
gaggaccgaa ggagctaacc gcttttttgc acaacatggg ggatcatgta actcgccttg    6480
atcgttggga accggagctg aatgaagcca taccaaacga cgagcgtgac accacgatgc    6540
ctgtagcaat ggcaacaacg ttgcgcaaac tattaactgg cgaactactt actctagctt    6600
cccggcaaca attaatagac tggatggagg cggataaagt tgcaggacca cttctgcgct    6660
cggcccttcc ggctggctgg tttattgctg ataaatctgg agccggtgag cgtgggtctc    6720
gcggtatcat tgcagcactg gggccagatg gtaagccctc ccgtatcgta gttatctaca    6780
cgacggggag tcaggcaact atggatgaac gaaatagaca gatcgctgag ataggtgcct    6840
cactgattaa gcattggtaa ctgtcagacc aagtttactc atatatactt tagattgatt    6900
taaaacttca ttttaatttt aaaaggatct aggtgaagat cctttttgat aatctcatga    6960
```

| | |
|---|---|
| ccaaaatccc ttaacgtgag ttttcgttcc actgagcgtc agaccccgta gaaaagatca | 7020 |
| aaggatcttc ttgagatcct ttttttctgc gcgtaatctg ctgcttgcaa acaaaaaaac | 7080 |
| caccgctacc agcggtggtt tgtttgccgg atcaagagct accaactctt tttccgaagg | 7140 |
| taactggctt cagcagagcg cagataccaa atactgttct tctagtgtag ccgtagttag | 7200 |
| gccaccactt caagaactct gtagcaccgc ctacatacct cgctctgcta atcctgttac | 7260 |
| cagtggctgc tgccagtggc gataagtcgt gtcttaccgg gttggactca agacgatagt | 7320 |
| taccggataa ggcgcagcgg tcgggctgaa cggggggttc gtgcacacag cccagcttgg | 7380 |
| agcgaacgac ctacaccgaa ctgagatacc tacagcgtga gctatgagaa agcgccacgc | 7440 |
| ttcccgaaga gagaaaggcg acaggtatc cggtaagcgg cagggtcgga acaggagagc | 7500 |
| gcacgaggga gcttccaggg ggaaacgcct ggtatcttta tagtcctgtc gggtttcgcc | 7560 |
| acctctgact tgagcgtcga tttttgtgat gctcgtcagg gggcggagc ctatggaaaa | 7620 |
| acgccagcaa cgcggccttt ttacggttcc tggccttttg ctggcctttt gctcacatgt | 7680 |
| tctttcctgc gttatcccct gattctgtgg ataaccgtat taccgccttt gagtgagctg | 7740 |
| ataccgctcg ccgcagccga acgaccgagc gcagcgagtc agtgagcgag gaagcggaag | 7800 |
| agcgcccaat acgcaaaccg cctctccccg cgcgttggcc gattcattaa tgcagctggc | 7860 |
| acgacaggtt tcccgactgg aaagcgggca gtgagcgcaa cgcaattaat gtgagttagc | 7920 |
| tcactcatta ggcaccccag gctttacact ttatgcttcc ggctcgtatg ttgtgtggaa | 7980 |
| ttgtgagcgg ataacaattt cacacaggaa acagctatga ccatgattac gccaagcgcg | 8040 |
| caattaaccc tcactaaagg gaacaaaagc tggagctgca agctt | 8085 |

<210> SEQ ID NO 10
<211> LENGTH: 7138
<212> TYPE: DNA
<213> ORGANISM: Artificial Sequence
<220> FEATURE:
<223> OTHER INFORMATION: Synthetic lentiviral vector

<400> SEQUENCE: 10

| | |
|---|---|
| aatgtagtct tatgcaatac tcttgtagtc ttgcaacatg gtaacgatga gttagcaaca | 60 |
| tgccttacaa ggagagaaaa agcaccgtgc atgccgattg gtggaagtaa ggtggtacga | 120 |
| tcgtgcctta ttaggaaggc aacagacggg tctgacatgg attggacgaa ccactgaatt | 180 |
| gccgcattgc agagatattg tatttaagtg cctagctcga tacataaacg ggtctctctg | 240 |
| gttagaccag atctgagcct gggagctctc tggctaacta gggaacccac tgcttaagcc | 300 |
| tcaataaagc ttgccttgag tgcttcaagt agtgtgtgcc cgtctgttgt gtgactctgg | 360 |
| taactagaga tccctcagac ccttttagtc agtgtggaaa atctctagca gtggcgcccg | 420 |
| aacagggact tgaaagcgaa agggaaacca gaggagctct ctcgacgcag gactcggctt | 480 |
| gctgaagcgc gcacggcaag aggcgagggg cggcgactgg tgagtacgcc aaaaattttg | 540 |
| actagcggag gctagaagga gagagatggg tgcgagagc tcagtattaa gcgggggaga | 600 |
| attagatcgc gatgggaaaa aattcggtta aggccagggg gaaagaaaaa atataaatta | 660 |
| aaacatatag tatgggcaag cagggagcta gaacgattcg cagttaatcc tggcctgtta | 720 |
| gaaacatcag aaggctgtag acaaatactg ggacagctac aaccatccct tcagacagga | 780 |
| tcagaagaac ttagatcatt atataataca gtagcaaccc tctattgtgt gcatcaaagg | 840 |
| atagagataa aagacaccaa ggaagcttta gacaagatag aggaagagca aaacaaaagt | 900 |
| aagaccaccg cacagcaagc ggccgctgat cttcagacct ggaggaggag atatgaggga | 960 |

```
caattggaga agtgaattat ataaatataa agtagtaaaa attgaaccat taggagtagc   1020
acccaccaag gcaaagagaa gagtggtgca gagagaaaaa agagcagtgg gaataggagc   1080
tttgttcctt gggttcttgg gagcagcagg aagcactatg ggcgcagcgt caatgacgct   1140
gacggtacag gccagacaat tattgtctgg tatagtgcag cagcagaaca atttgctgag   1200
ggctattgag gcgcaacagc atctgttgca actcacagtc tggggcatca agcagctcca   1260
ggcaagaatc ctggctgtgg aaagatacct aaaggatcaa cagctcctgg ggatttgggg   1320
ttgctctgga aaactcattt gcaccactgc tgtgccttgg aatgctagtt ggagtaataa   1380
atctctggaa cagatttgga atcacacgac ctggatggag tgggacagag aaattaacaa   1440
ttacacaagc ttaatacact ccttaattga agaatcgcaa aaccagcaag aaaagaatga   1500
acaagaatta ttggaattag ataaatgggc aagtttgtgg aattggttta acataacaaa   1560
ttggctgtgg tatataaaat tattcataat gatagtagga ggcttggtag gtttaagaat   1620 agttttgct gtacttttcta tagtgaatag agttaggcag ggatattcac cattatcgtt   1680
tcagacccac ctcccaaccc cgaggggacc cgacaggccc gaaggaatag aagaagaagg   1740
tggagagaga gacagagaca gatccattcg attagtgaac ggatctcgac ggtatcgcta   1800
gcttttaaaa gaaaaggggg gattgggggg tacagtgcag gggaagaat agtagacata   1860 atagcaacag acatcaaac taagaatta caaaaacaaa ttacaaaaat tcaaaattt   1920 actagtgatt atcggatcaa cttttgtatag aaaagttggg ctccggtgcc cgtcagtggg   1980
cagagcgcac atcgcccaca gtccccgaga agttgggggg aggggtcggc aattgatccg   2040
gtgcctagag aaggtggcgc ggggtaaact gggaaagtga tgtcgtgtac tggctccgcc   2100
tttttcccga gggtggggga gaaccgtata taagtgcagt agtcgccgtg aacgttcttt   2160
ttcgcaacgg gtttgccgcc agaacacagg caagtttgta caaaaaagca ggctgccacc   2220
atggtgagca agggcgagga gctgttcacc ggggtggtgc ccatcctggt cgagctggac   2280
ggcgacgtaa acggccacaa gttcagcgtg tccggcgagg gcgagggcga tgccacctac   2340
ggcaagctga ccctgaagtt catctgcacc accggcaagc tgcccgtgcc ctggcccacc   2400
ctcgtgacca cctgaccta cggcgtgcag tgcttcagcc gctaccccga ccacatgaag   2460
cagcacgact tcttcaagtc cgccatgccc gaaggctacg tccaggagcg caccatcttc   2520
ttcaaggacg acggcaacta caagacccgc gccgaggtga agttcgaggg cgacaccctg   2580
gtgaaccgca tcgagctgaa gggcatcgac ttcaaggagg acggcaacat cctggggcac   2640
aagctggagt acaactacaa cagccacaac gtctatatca tggccgacaa gcagaagaac   2700
ggcatcaagg tgaacttcaa gatccgccac aacatcgagg acggcagcgt gcagctcgcc   2760
gaccactacc agcagaacac ccccatcggc gacggccccg tgctgctgcc cgacaaccac   2820
tacctgagca cccagtccgc cctgagcaaa gaccccaacg agaagcgcga tcacatggtc   2880
ctgctggagt tcgtgaccgc cgccgggatc actctcggca tggacgagct gtacaagtaa   2940
acccagcttt cttgtacaaa gtggtgataa tcgaattccg ataatcaacc tctggattac   3000
aaaatttgtg aaagattgac tggtattctt aactatgttg ctccttttac gctatgtgga   3060
tacgctgctt taatgccttt gtatcatgct attgcttccc gtatggcttt cattttctcc   3120
tccttgtata aatcctggtt gctgtctctt tatgaggagt tgtggcccgt tgtcaggcaa   3180
cgtggcgtgg tgtgcactgt gtttgctgac gcaaccccca ctggttgggg cattgccacc   3240
acctgtcagc tcctttccgg gactttcgct ttcccccctcc ctattgccac ggcggaactc   3300
```

```
atcgccgcct gccttgcccg ctgctggaca ggggctcggc tgttgggcac tgacaattcc    3360
gtggtgttgt cggggaagct gacgtccttt ccatggctgc tcgcctgtgt tgccacctgg    3420
attctgcgcg ggacgtcctt ctgctacgtc ccttcggccc tcaatccagc ggaccttcct    3480
tcccgcggcc tgctgccggc tctgcggcct cttccgcgtc ttcgccttcg ccctcagacg    3540
agtcggatct cccttttggg cgcctccccg catcgggaat cccgcggtt cgctttaaga    3600
ccaatgactt acaaggcagc tgtagatctt agccactttt taaaagaaaa gggggactg    3660
gaagggctaa ttcactccca acgaagacaa gatctgcttt ttgcttgtac tgggtctctc    3720
tggttagacc agatctgagc ctgggagctc tctggctaac tagggaaccc actgcttaag    3780
cctcaataaa gcttgccttg agtgcttcaa gtagtgtgtg cccgtctgtt gtgtgactct    3840
ggtaactaga gatccctcag acccttttag tcagtgtgga aaatctctag cagtagtagt    3900
tcatgtcatc ttattattca gtatttataa cttgcaaaga aatgaatatc agagagtgag    3960
aggaacttgt ttattgcagc ttataatggt tacaaataaa gcaatagcat cacaaatttc    4020
acaaataaag catttttttc actgcattct agttgtggtt tgtccaaact catcaatgta    4080
tcttatcatg tctggctcta gctatcccgc ccctaactcc gcccatcccg cccctaactc    4140
cgcccagttc cgcccattct ccgccccatg gctgactaat ttttttttatt tatgcagagg    4200
ccgaggccgc ctcggcctct gagctattcc agaagtagtg aggaggcttt tttggaggcc    4260
tagggacgta cccaattcgc cctatagtga gtcgtattac gcgcgctcac tggccgtcgt    4320
tttacaacgt cgtgactggg aaaaccctgg cgttacccaa cttaatcgcc ttgcagcaca    4380
tcccccttc gccagctggc gtaatagcga agaggcccgc accgatcgcc cttcccaaca    4440
gttgcgcagc ctgaatggcg aatgggacgc gccctgtagc ggcgcattaa gcgcggcggg    4500
tgtggtggtt acgcgcagcg tgaccgctac acttgccagc gccctagcgc ccgctccttt    4560
cgctttcttc ccttcctttc tcgccacgtt cgccggcttt ccccgtcaag ctctaaatcg    4620
ggggctccct ttagggttcc gatttagtgc tttacggcac ctcgacccca aaaaacttga    4680
ttagggtgat ggttcacgta gtgggccatc gccctgatag acggtttttc gccctttgac    4740
gttggagtcc acgttcttta atagtggact cttgttccaa actggaacaa cactcaaccc    4800
tatctcggtc tattcttttg atttataagg gattttgccg atttcggcct attggttaaa    4860
aaatgagctg atttaacaaa aatttaacgc gaattttaac aaaatattaa cgcttacaat    4920
ttaggtggca cttttcgggg aaatgtgcgc ggaacccta tttgtttatt tttctaaata    4980
cattcaaata tgtatccgct catgagacaa taaccctgat aaatgcttca ataatattga    5040
aaaaggaaga gtatgagtat tcaacatttc cgtgtcgccc ttattccctt ttttgcggca    5100
ttttgccttc ctgttttgc tcacccagaa acgctggtga agtaaaaga tgctgaagat    5160
cagttgggtg cacgagtggg ttacatcgaa ctggatctca acagcggtaa gatccttgag    5220
agttttcgcc ccgaagaacg ttttccaatg atgagcactt taaagttct gctatgtggc    5280
gcggtattat cccgtattga cgccgggcaa gagcaactcg gtcgccgcat acactattct    5340
cagaatgact tggttgagta ctcaccagtc acagaaaagc atcttacgga tggcatgaca    5400
gtaagagaat tatgcagtgc tgccataacc atgagtgata acactgcggc caacttactt    5460
ctgacaacga tcggaggacc gaaggagcta accgcttttt tgcacaacat ggggatcat    5520
gtaactcgcc ttgatcgttg ggaaccggag ctgaatgaag ccataccaaa cgacgagcgt    5580
gacaccacga tgcctgtagc aatggcaaca acgttgcgca aactattaac tggcgaacta    5640
cttactctag cttcccggca acaattaata gactggatgg aggcggataa agttgcagga    5700
```

```
ccacttctgc gctcggccct tccggctggc tggtttattg ctgataaatc tggagccggt    5760
gagcgtgggt ctcgcggtat cattgcagca ctggggccag atggtaagcc ctcccgtatc    5820
gtagttatct acacgacggg gagtcaggca actatggatg aacgaaatag acagatcgct    5880
gagataggtg cctcactgat taagcattgg taactgtcag accaagttta ctcatatata    5940
ctttagattg atttaaaact tcatttttaa tttaaaagga tctaggtgaa gatcctttt     6000 gataatctca tgaccaaaat cccttaacgt gagttttcgt tccactgagc gtcagacccc    6060
gtagaaaaga tcaaaggatc ttcttgagat cctttttttc tgcgcgtaat ctgctgcttg    6120
caaacaaaaa aaccaccgct accagcggtg gtttgtttgc cggatcaaga gctaccaact    6180
ctttttccga aggtaactgg cttcagcaga gcgcagatac caaatactgt tcttctagtg    6240
tagccgtagt taggccacca cttcaagaac tctgtagcac cgcctacata cctcgctctg    6300
ctaatcctgt taccagtggc tgctgccagt ggcgataagt cgtgtcttac cgggttggac    6360
tcaagacgat agttaccgga taaggcgcag cggtcgggct gaacggggggg ttcgtgcaca    6420 cagcccagct tggagcgaac gacctacacc gaactgagat acctacagcg tgagctatga    6480
gaaagcgcca cgcttcccga agagagaaag gcggacaggt atccggtaag cggcagggtc    6540
ggaacaggag agcgcacgag ggagcttcca gggggaaacg cctggtatct ttatagtcct    6600
gtcgggtttc gccacctctg acttgagcgt cgatttttgt gatgctcgtc aggggggcgg    6660
agcctatgga aaaacgccag caacgcggcc ttttttacggt tcctggcctt ttgctggcct    6720
tttgctcaca tgttctttcc tgcgttatcc cctgattctg tggataaccg tattaccgcc    6780
tttgagtgag ctgataccgc tcgccgcagc cgaacgaccg agcgcagcga gtcagtgagc    6840
gaggaagcgg aagagcgccc aatacgcaaa ccgcctctcc ccgcgcgttg gccgattcat    6900
taatgcagct ggcacgacag gtttcccgac tggaaagcgg gcagtgagcg caacgcaatt    6960
aatgtgagtt agctcactca ttaggcaccc caggctttac actttatgct tccggctcgt    7020
atgttgtgtg gaattgtgag cggataacaa tttcacacag gaaacagcta tgaccatgat    7080
tacgccaagc gcgcaattaa ccctcactaa agggaacaaa agctggagct gcaagctt     7138
```

<210> SEQ ID NO 11
<211> LENGTH: 8639
<212> TYPE: DNA
<213> ORGANISM: Artificial Sequence
<220> FEATURE:
<223> OTHER INFORMATION: Synthetic lentiviral vector

<400> SEQUENCE: 11

```
aatgtagtct tatgcaatac tcttgtagtc ttgcaacatg gtaacgatga gttagcaaca      60
tgccttacaa ggagagaaaa agcaccgtgc atgccgattg gtggaagtaa ggtggtacga     120
tcgtgcctta ttaggaaggc aacagacggg tctgacatgg attggacgaa ccactgaatt     180
gccgcattgc agagatattg tatttaagtg cctagctcga tacataaacg ggtctctctg     240
gttagaccag atctgagcct gggagctctc tggctaacta gggaacccac tgcttaagcc     300
tcaataaagc ttgccttgag tgcttcaagt agtgtgtgcc cgtctgttgt gtgactctgg     360
taactagaga tccctcagac ccttttagtc agtgtggaaa atctctagca gtggcgcccg     420
aacagggact tgaaagcgaa agggaaacca gaggagctct ctcgacgcag gactcggctt     480
gctgaagcgc gcacggcaag aggcgagggg cggcgactgg tgagtacgcc aaaaattttg     540
actagcggag gctagaagga gagagatggg tgcgagagcg tcagtattaa gcgggggaga     600
```

```
attagatcgc gatgggaaaa aattcggtta aggccagggg gaaagaaaaa atataaatta    660
aaacatatag tatgggcaag cagggagcta gaacgattcg cagttaatcc tggcctgtta    720
gaaacatcag aaggctgtag acaaatactg ggacagctac aaccatccct tcagacagga    780
tcagaagaac ttagatcatt atataataca gtagcaaccc tctattgtgt gcatcaaagg    840
atagagataa aagacaccaa ggaagcttta gacaagatag aggaagagca aaacaaaagt    900
aagaccaccg cacagcaagc ggccgctgat cttcagacct ggaggaggag atatgaggga    960 caattgggaga agtgaattat ataaatataa agtagtaaaa attgaaccat taggagtagc   1020
acccaccaag gcaaagagaa gagtggtgca gagagaaaaa agagcagtgg gaataggagc   1080
tttgttcctt gggttcttgg gagcagcagg aagcactatg ggcgcagcgt caatgacgct   1140
gacggtacag gccagacaat tattgtctgg tatagtgcag cagcagaaca atttgctgag   1200
ggctattgag gcgcaacagc atctgttgca actcacagtc tggggcatca agcagctcca   1260
ggcaagaatc ctggctgtgg aaagatacct aaaggatcaa cagctcctgg ggatttgggg   1320
ttgctctgga aaactcattt gcaccactgc tgtgccttgg aatgctagtt ggagtaataa   1380
atctctggaa cagatttgga atcacacgac ctggatggag tgggacagag aaattaacaa   1440
ttacacaagc ttaatacact ccttaattga agaatcgcaa aaccagcaag aaaagaatga   1500
acaagaatta ttggaattag ataaatgggc aagtttgtgg aattggttta acataacaaa   1560
ttggctgtgg tatataaaat tattcataat gatagtagga ggcttggtag gtttaagaat   1620 agttttgct gtactttcta tagtgaatag agttaggcag ggatattcac cattatcgtt   1680
tcagacccac ctcccaaccc cgaggggacc cgacaggccc gaaggaatag aagaagaagg   1740
tggagagaga gacagagaca gatccattcg attagtgaac ggatctcgac ggtatcgcta   1800
gcttttaaaa gaaaaggggg gattgggggg tacagtgcag gggaagaat agtagacata   1860 atagcaacag acatacaaac taaagaatta caaaaacaaa ttacaaaaat tcaaaatttt   1920
actagtgatt atcggatcaa ctttgtatag aaaagttgct cgacattgat tattgactag   1980
ttattaatag taatcaatta cggggtcatt agttcatagc ccatatatgg agttccgcgt   2040
tacataactt acggtaaatg gcccgcctgg ctgaccgccc aacgacccc gcccattgac    2100 gtcaataatg acgtatgttc ccatagtaac gccaataggg actttccatt gacgtcaatg   2160
ggtggagtat ttacggtaaa ctgcccactt ggcagtacat caagtgtatc atatgccaag   2220
tacgccccct attgacgtca atgacggtaa atggcccgcc tggcattatg cccagtacat   2280
gaccttatgg gactttccta cttggcagta catctacgta ttagtcatcg ctattaccat   2340
ggtcgaggtg agccccacgt tctgcttcac tctccccatc tcccccccct ccccaccccc   2400
aattttgtat ttatttattt tttaattatt ttgtgcagcg atggggggcgg gggggggggg   2460 ggggcgcgcg ccaggcgggg cggggcgggg cgaggggcgg ggcggggcga ggcggagagg   2520
tgcggcggca gccaatcaga gcggcgcgct ccgaaagttt cctttatgg cgaggcggcg    2580 gcggcggcgg ccctataaaa agcgaagcgc gcggcgggcg ggagtcgctg cgcgctgcct   2640
tcgccccgtg ccccgctccg ccgccgcctc gcgccgcccg cccccggctct gactgaccgc   2700 gttactccca caggtgagcg ggcgggacgg cccttctcct ccgggctgta attagcgctt   2760
ggtttaatga cggcttgttt cttttctgtg gctgcgtgaa agccttgagg ggctccggga   2820
gggccctttg tgcggggga gcggctcggg gggtgcgtgc gtgtgtgtgt gcgtggggag   2880
cgccgcgtgc ggctccgcgc tgcccggcgg ctgtgagcgc tgcggcgcg gcgcggggct   2940 ttgtgcgctc cgcagtgtgc gcgaggggag cgcggccggg ggcggtgccc cgcggtgcgg   3000
```

```
ggggggctgc gaggggaaca aaggctgcgt gcggggtgtg tgcgtggggg ggtgagcagg   3060
gggtgtgggc gcgtcggtcg ggctgcaacc ccccctgcac cccctcccc gagttgctga    3120
gcacggcccg gcttcgggtg cggggctccg tacgggcgt ggcgcggggc tcgccgtgcc    3180
gggcggggg tggcggcagg tggggtgcc gggcggggcg gggccgcctc gggcgggga     3240
gggctcgggg gaggggcgcg gcggccccccg gagcgccggc ggctgtcgag gcgcggcgag   3300
ccgcagccat tgccttttat ggtaatcgtg cgagagggcg cagggacttc ctttgtccca   3360
aatctgtgcg gagccgaaat ctgggaggcg ccgccgcacc ccctctagcg ggcgcggggc   3420
gaagcggtgc ggcgccggca ggaaggaaat gggcggggag ggccttcgtg cgtcgccgcg   3480
ccgccgtccc cttctccctc tccagcctcg gggctgtccg cgggggggacg gctgccttcg   3540
gggggacgg ggcagggcgg ggttcggctt ctggcgtgtg accggcggct ctagagcctc    3600
tgctaaccat gttcatgcct tcttctttt cctacagctc ctgggcaacg tgctggttat    3660
tgtgctgtct catcatttg gcaaagaatt gcaagtttgt acaaaaagc aggctgccac    3720
catggtgagc aagggcgagg agctgttcac cggggtggtg cccatcctgg tcgagctgga   3780
cggcgacgta acggccaca agttcagcgt gtccggcgag ggcgagggcg atgccaccta   3840
cggcaagctg accctgaagt tcatctgcac caccggcaag ctgcccgtgc cctggcccac   3900
cctcgtgacc accctgacct acggcgtgca gtgcttcagc cgctaccccg accacatgaa   3960
gcagcacgac ttcttcaagt ccgccatgcc cgaaggctac gtccaggagc gcaccatctt   4020
cttcaaggac gacggcaact acaagacccg cgccgaggtg aagttcgagg gcgacaccct   4080
ggtgaaccgc atcgagctga agggcatcga cttcaaggag gacggcaaca tcctggggca   4140
caagctggag tacaactaca acagccacaa cgtctatatc atggccgaca gcagaagaa   4200
cggcatcaag gtgaacttca agatccgcca caacatcgag gacggcagcg tgcagctcgc   4260
cgaccactac cagcagaaca ccccccatcgg cgacggcccc gtgctgctgc ccgacaacca   4320
ctacctgagc acccagtccg ccctgagcaa agaccccaac gagaagcgcg atcacatggt   4380
cctgctggag ttcgtgaccg ccgccgggat cactctcggc atggacgagc tgtacaagta   4440
aacccagctt tcttgtacaa agtggtgata atcgaattcc gataatcaac ctctggatta   4500
caaaatttgt gaaagattga ctggtattct taactatgtt gctcctttta cgctatgtgg   4560
atacgctgct ttaatgcctt tgtatcatgc tattgcttcc cgtatggctt tcattttctc   4620
ctccttgtat aaatcctggt tgctgtctct ttatgaggag ttgtggcccg ttgtcaggca   4680
acgtggcgtg gtgtgcactg tgtttgctga cgcaaccccc actggttggg gcattgccac   4740
cacctgtcag ctccttccg ggactttcgc tttccccctc cctattgcca cggcggaact   4800
catcgccgcc tgccttgccc gctgctggac aggggctcgg ctgttgggca ctgacaattc   4860
cgtggtgttg tcggggaagc tgacgtcctt tccatggctg ctcgcctgtg ttgccacctg   4920
gattctgcgc gggacgtcct tctgctacgt cccttcggcc ctcaatccag cggaccttcc   4980
ttcccgcggc ctgctgccgg ctctgcggcc tcttccgcgt cttcgccttc gccctcagac   5040
gagtcggatc tccctttggg ccgcctcccc gcatcgggaa ttcccgcggt tcgctttaag   5100
accaatgact tacaaggcag ctgtagatct tagccacttt ttaaaagaaa aggggggact   5160
ggaagggcta attcactccc aacgaagaca agatctgctt tttgcttgta ctgggtctct   5220
ctggttagac cagatctgag cctgggagct ctctggctaa ctaggaacc cactgcttaa   5280
gcctcaataa agcttgcctt gagtgcttca agtagtgtgt gcccgtctgt tgtgtgactc   5340
```

```
tggtaactag agatccctca gacccttttta gtcagtgtgg aaaatctcta gcagtagtag   5400
ttcatgtcat cttattattc agtatttata acttgcaaag aaatgaatat cagagagtga   5460
gaggaacttg tttattgcag cttataatgg ttacaaataa agcaatagca tcacaaattt   5520
cacaaataaa gcattttttt cactgcattc tagttgtggt ttgtccaaac tcatcaatgt   5580
atcttatcat gtctggctct agctatcccg cccctaactc cgcccatccc gcccctaact   5640
ccgcccagtt ccgcccattc tccgccccat ggctgactaa ttttttttat ttatgcagag   5700
gccgaggccg cctcggcctc tgagctattc cagaagtagt gaggaggctt ttttggaggc   5760
ctagggacgt acccaattcg ccctatagtg agtcgtatta cgcgcgctca ctggccgtcg   5820
ttttacaacg tcgtgactgg gaaaaccctg gcgttaccca acttaatcgc cttgcagcac   5880
atccccctt cgccagctgg cgtaatagcg aagaggcccg caccgatcgc ccttcccaac   5940
agttgcgcag cctgaatggc gaatgggacg cgccctgtag cggcgcatta gcgcggcgg   6000
gtgtggtggt tacgcgcagc gtgaccgcta cacttgccag cgccctagcg cccgctcctt   6060
tcgctttctt cccttccttt ctcgccacgt tcgccggctt tccccgtcaa gctctaaatc   6120
gggggctccc tttagggttc cgatttagtg ctttacggca cctcgacccc aaaaaacttg   6180
attagggtga tggttcacgt agtgggccat cgccctgata acggttttt cgcccttga   6240
cgttggagtc cacgttcttt aatagtggac tcttgttcca aactggaaca cactcaacc   6300
ctatctcggt ctattctttt gatttataag ggattttgcc gatttcggcc tattggttaa   6360
aaaatgagct gatttaacaa aaatttaacg cgaattttaa caaaatatta acgcttacaa   6420
tttaggtggc acttttcggg gaaatgtgcg cggaacccct atttgtttat ttttctaaat   6480
acattcaaat atgtatccgc tcatgagaca ataaccctga taaatgcttc aataatattg   6540
aaaaaggaag agtatgagta ttcaacattt ccgtgtcgcc cttattccct ttttttgcggc   6600
attttgcctt cctgttttg ctcacccaga aacgctggtg aaagtaaaag atgctgaaga   6660
tcagttgggg cacgagtgg gttacatcga actggatctc aacagcggta agatccttga   6720
gagttttcgc cccgaagaac gttttccaat gatgagcact tttaaagttc tgctatgtgg   6780
cgcggtatta tcccgtattg acgccgggca agagcaactc ggtcgccgca tacactattc   6840
tcagaatgac ttggttgagt actcaccagt cacagaaaag catcttacgg atggcatgac   6900
agtaagagaa ttatgcagtg ctgccataac catgagtgat aacactgcgg ccaacttact   6960
tctgacaacg atcggaggac cgaaggagct aaccgctttt ttgcacaaca tgggggatca   7020
tgtaactcgc cttgatcgtt gggaaccgga gctgaatgaa gccataccaa acgacgagcg   7080
tgacaccacg atgcctgtag caatggcaac aacgttgcgc aaactattaa ctggcgaact   7140
acttactcta gcttcccggc aacaattaat agactggatg gaggcggata agttgcagg   7200
accacttctg cgctcggccc ttccggctgg ctggtttatt gctgataaat ctggagccgg   7260
tgagcgtggg tctcgcggta tcattgcagc actggggcca gatggtaagc cctcccgtat   7320
cgtagttatc tacacgacgg ggagtcaggc aactatggat gaacgaaata gacagatcgc   7380
tgagataggt gcctcactga ttaagcattg gtaactgtca gaccaagttt actcatatat   7440
actttagatt gatttaaaac ttcattttta atttaaaagg atctaggtga agatcctttt   7500
tgataatctc atgaccaaaa tcccttaacg tgagttttcg ttccactgag cgtcagaccc   7560
cgtagaaaag atcaaaggat cttcttgaga tcctttttt ctgcgcgtaa tctgctgctt   7620
gcaaacaaaa aaaccaccgc taccagcggt ggtttgtttg ccggatcaag agctaccaac   7680
tctttttccg aaggtaactg gcttcagcag agcgcagata ccaaatactg ttcttctagt   7740
```

```
gtagccgtag ttaggccacc acttcaagaa ctctgtagca ccgcctacat acctcgctct    7800
gctaatcctg ttaccagtgg ctgctgccag tggcgataag tcgtgtctta ccgggttgga    7860
ctcaagacga tagttaccgg ataaggcgca gcggtcgggc tgaacggggg gttcgtgcac    7920
acagcccagc ttggagcgaa cgacctacac cgaactgaga tacctacagc gtgagctatg    7980
agaaagcgcc acgcttcccg aagagagaaa ggcggacagg tatccggtaa gcggcagggt    8040
cggaacagga gagcgcacga gggagcttcc agggggaaac gcctggtatc tttatagtcc    8100
tgtcgggttt cgccacctct gacttgagcg tcgatttttg tgatgctcgt caggggggcg    8160
gagcctatgg aaaaacgcca gcaacgcggc cttttacgg ttcctggcct tttgctggcc    8220
ttttgctcac atgttctttc ctgcgttatc ccctgattct gtggataacc gtattaccgc    8280
ctttgagtga gctgataccg ctcgccgcag ccgaacgacc gagcgcagcg agtcagtgag    8340
cgaggaagcg gaagagcgcc caatacgcaa accgcctctc cccgcgcgtt ggccgattca    8400
ttaatgcagc tggcacgaca ggtttcccga ctggaaagcg ggcagtgagc gcaacgcaat    8460
taatgtgagt tagctcactc attaggcacc ccaggcttta cactttatgc ttccggctcg    8520
tatgttgtgt ggaattgtga gcggataaca atttcacaca ggaaacagct atgaccatga    8580
ttacgccaag cgcgcaatta accctcacta aagggaacaa aagctggagc tgcaagctt     8639

<210> SEQ ID NO 12
<211> LENGTH: 7704
<212> TYPE: DNA
<213> ORGANISM: Artificial Sequence
<220> FEATURE:
<223> OTHER INFORMATION: Synthetic lentiviral vector

<400> SEQUENCE: 12
aatgtagtct tatgcaatac tcttgtagtc ttgcaacatg gtaacgatga gttagcaaca      60
tgccttacaa ggagagaaaa agcaccgtgc atgccgattg gtggaagtaa ggtggtacga     120
tcgtgcctta ttaggaaggc aacagacggg tctgacatgg attggacgaa ccactgaatt     180
gccgcattgc agagatattg tatttaagtg cctagctcga tacataaacg gtctctctg      240 gttagaccag atctgagcct gggagctctc tggctaacta gggaacccac tgcttaagcc     300
tcaataaagc ttgccttgag tgcttcaagt agtgtgtgcc cgtctgttgt gtgactctgg     360
taactagaga tccctcagac ccttttagtc agtgtggaaa atctctagca gtggcgcccg     420
aacagggact tgaaagcgaa agggaaacca gaggagctct ctcgacgcag gactcggctt     480
gctgaagcgc gcacggcaag aggcgagggg cggcgactgg tgagtacgcc aaaaattttg     540
actagcggag gctagaagga gagagatggg tgcgagagcg tcagtattaa gcggggagaa     600
attagatcgc gatgggaaaa aattcggtta aggccagggg gaagaaaaa atataaatta     660 aaacatatag tatgggcaag cagggagcta gaacgattcg cagttaatcc tggcctgtta     720
gaaacatcag aaggctgtag acaaatactg ggacagctac aaccatccct tcagacagga     780
tcagaagaac ttagatcatt atataataca gtagcaaccc tctattgtgt gcatcaaagg     840
atagagataa aagacaccaa ggaagcttta gacaagatag aggaagagca aaacaaaagt     900
aagaccaccg cacagcaagc ggccgctgat cttcagacct ggaggaggag atatgaggga     960
caattggaga agtgaattat ataaatataa agtagtaaaa attgaaccat taggagtagc    1020
acccaccaag gcaaagagaa gagtggtgca gagagaaaaa agagcagtgg aataggagc     1080 tttgttcctt gggttcttgg gagcagcagg aagcactatg ggcgcagcgt caatgacgct    1140
```

```
gacggtacag gccagacaat tattgtctgg tatagtgcag cagcagaaca atttgctgag    1200
ggctattgag gcgcaacagc atctgttgca actcacagtc tggggcatca agcagctcca    1260
ggcaagaatc ctggctgtgg aaagatacct aaaggatcaa cagctcctgg ggatttgggg    1320
ttgctctgga aaactcattt gcaccactgc tgtgccttgg aatgctagtt ggagtaataa    1380
atctctggaa cagatttgga atcacacgac ctggatggag tgggacagag aaattaacaa    1440
ttacacaagc ttaatacact ccttaattga gaatcgcaa accagcaag aaaagaatga      1500 acaagaatta ttggaattag ataaatgggc aagtttgtgg aattggttta acataacaaa    1560
ttggctgtgg tatataaaat tattcataat gatagtagga ggcttggtag gtttaagaat    1620 agttttgct gtactttcta tagtgaatag agttaggcag ggatattcac cattatcgtt      1680
tcagacccac ctcccaaccc cgaggggacc cgacaggccc gaaggaatag aagaagaagg    1740
tggagagaga gacagagaca gatccattcg attagtgaac ggatctcgac ggtatcgcta    1800
gcttttaaaa gaaaggggg gattgggggg tacagtgcag gggaagaat agtagacata       1860 atagcaacag acatacaaac taaagaatta caaaaacaaa ttacaaaaat tcaaaattt       1920 actagtgatt atcggatcaa ctttgtatag aaaagttgcg ttacataact acggtaaat       1980 ggcccgcctg gctgaccgcc caacgacccc cgcccattga cgtcaatagt aacgccaata    2040
gggactttcc attgacgtca atgggtggag tatttacggt aaactgccca cttggcagta    2100
catcaagtgt atcatatgcc aagtacgccc cctattgacg tcaatgacgg taaatggccc    2160
gcctggcatt gtgcccagta catgacctta tgggactttc ctacttggca gtacatctac    2220
gtattagtca tcgctattac catggtcgag gtgagcccca cgttctgctt cactctcccc    2280
atctcccccc cctccccacc cccaattttg tatttattta ttttttaatt attttgtgca    2340
gcgatggggg cggggggggg ggggggcgc gcgccaggcg gggcggggcg gggcgagggg      2400
cggggcgggg cgaggcggag aggtgcggcg gcagccaatc agagcggcgc gctccgaaag    2460 tttccttta tggcgaggcg gcggcggcg cggccctata aaaagcgaag cgcgcggcgg       2520
gcgggagtcg ctgcgcgctg ccttcgcccc gtgccccgct ccgccgccgc ctcgcgccgc    2580 ccgcccggc tctgactgac cgcgttactc ccacaggtga gcgggcggga cggccccttct    2640 cctccgggct gtaattagct gagcaagagg taagggttta agggatggtt ggttggtggg    2700
gtattaatgt ttaattacct ggagcacctg cctgaaatca ctttttttca ggttggcaag    2760
tttgtacaaa aaagcaggct gccaccatgg tgagcaaggg cgaggagctg ttcaccgggg    2820
tggtgcccat cctggtcgag ctggacgcg acgtaaacgg ccacaagttc agcgtgtccg    2880
gcgagggcga gggcgatgcc acctacggca agctgaccct gaagttcatc tgcaccaccg    2940
gcaagctgcc cgtgccctgg cccaccctcg tgaccaccct gacctacggc gtgcagtgct    3000
tcagccgcta ccccgaccac atgaagcagc acgacttctt caagtccgcc atgcccgaag    3060
gctacgtcca ggagcgcacc atcttcttca aggacgacgg caactacaag acccgcgccg    3120
aggtgaagtt cgagggcgac accctggtga accgcatcga gctgaagggc atcgacttca    3180
aggaggacgg caacatcctg ggcacaagc tggagtacaa ctacaacagc cacaacgtct     3240
atatcatggc cgacaagcag aagaacggca tcaaggtgaa cttcaagatc cgccacaaca    3300
tcgaggacgg cagcgtgcag ctcgccgacc actaccagca gaacacccc atcggcgacg     3360 gccccgtgct gctgcccgac aaccactacc tgagcaccca gtccgccctg agcaaagacc    3420
ccaacgagaa gcgcgatcac atggtcctgc tggagttcgt gaccgccgcc gggatcactc    3480
tcggcatgga cgagctgtac aagtaaaccc agctttcttg tacaaagtgg tgataatcga    3540
```

```
attccgataa tcaacctctg gattacaaaa tttgtgaaag attgactggt attcttaact   3600
atgttgctcc ttttacgcta tgtggatacg ctgctttaat gcctttgtat catgctattg   3660
cttcccgtat ggcttcatt ttctcctcct tgtataaatc ctggttgctg tctctttatg   3720
aggagttgtg gcccgttgtc aggcaacgtg gcgtggtgtg cactgtgttt gctgacgcaa   3780
cccccactgg ttggggcatt gccaccacct gtcagctcct ttccgggact ttcgctttcc   3840
ccctccctat tgccacggcg gaactcatcg ccgcctgcct tgcccgctgc tggacagggg   3900
ctcggctgtt gggcactgac aattccgtgg tgttgtcggg gaagctgacg tcctttccat   3960
ggctgctcgc ctgtgttgcc acctggattc tgcgcgggac gtccttctgc tacgtccctt   4020
cggccctcaa tccagcggac cttccttccc gcggcctgct gccggctctg cggcctcttc   4080
cgcgtcttcg ccttcgccct cagacgagtc ggatctccct ttgggccgcc tccccgcatc   4140
gggaattccc gcggttcgct ttaagaccaa tgacttacaa ggcagctgta gatcttagcc   4200 acttttaaa agaaaagggg ggactggaag ggctaattca ctcccaacga agacaagatc   4260 tgcttttgc ttgtactggg tctctctggt tagaccagat ctgagcctgg gagctctctg   4320
gctaactagg gaacccactg cttaagcctc aataaagctt gccttgagtg cttcaagtag   4380
tgtgtgcccg tctgttgtgt gactctggta actagagatc cctcagaccc ttttagtcag   4440
tgtggaaaat ctctagcagt agtagttcat gtcatcttat tattcagtat ttataacttg   4500
caaagaaatg aatatcagag agtgagagga acttgtttat tgcagcttat aatggttaca   4560
aataaagcaa tagcatcaca aatttcacaa ataaagcatt ttttcactg cattctagtt   4620 gtggtttgtc caaactcatc aatgtatctt atcatgtctg gctctagcta tcccgcccct   4680
aactccgccc atcccgcccc taactccgcc cagttccgcc cattctccgc ccatggctg   4740 actaattttt tttatttatg cagaggccga ggccgcctcg gcctctgagc tattccagaa   4800
gtagtgagga ggcttttttg gaggcctagg gacgtaccca attcgcccta tagtgagtcg   4860
tattacgcgc gctcactggc cgtcgtttta caacgtcgtg actgggaaaa ccctggcgtt   4920
acccaactta atcgccttgc agcacatccc cctttcgcca gctggcgtaa tagcgaagag   4980
gcccgcaccg atcgcccttc ccaacagttg cgcagcctga atggcgaatg ggacgcgccc   5040
tgtagcggcg cattaagcgc ggcgggtgtg gtggttacgc gcagcgtgac cgctacactt   5100
gccagcgccc tagcgcccgc tcctttcgct ttcttccctt cctttctcgc cacgttcgcc   5160
ggctttcccc gtcaagctct aaatcggggg ctcccttag ggttccgatt tagtgcttta   5220
cggcacctcg accccaaaaa acttgattag ggtgatggt cacgtagtgg gccatcgccc   5280
tgatagacgg ttttcgccc tttgacgttg gagtccacgt tctttaatag tggactcttg   5340
ttccaaactg gaacaacact caaccctatc tcggtctatt cttttgattt ataagggatt   5400
ttgccgattt cggcctattg gttaaaaaat gagctgattt aacaaaaatt taacgcgaat   5460
tttaacaaaa tattaacgct tacaatttag gtggcacttt tcggggaaat gtgcgcggaa   5520
cccctatttg tttatttttc taaatacatt caaatatgta tccgctcatg agacaataac   5580
cctgataaat gcttcaataa tattgaaaaa ggaagagtat gagtattcaa catttccgtg   5640
tcgcccttat tcccttttt gcggcatttt gccttcctgt ttttgctcac ccagaaacgc   5700
tggtgaaagt aaaagatgct gaagatcagt tgggtgcacg agtgggttac atcgaactgg   5760
atctcaacag cggtaagatc cttgagagtt ttcgccccga agaacgtttt ccaatgatga   5820 gcactttaa agttctgcta tgtggcgcgg tattatcccg tattgacgcc gggcaagagc   5880
```

| aactcggtcg | ccgcatacac | tattctcaga | atgacttggt | tgagtactca | ccagtcacag | 5940 |
| aaaagcatct | tacggatggc | atgacagtaa | gagaattatg | cagtgctgcc | ataaccatga | 6000 |
| gtgataacac | tgcggccaac | ttacttctga | caacgatcgg | aggaccgaag | gagctaaccg | 6060 |
| cttttttgca | caacatgggg | gatcatgtaa | ctcgccttga | tcgttgggaa | ccggagctga | 6120 |
| atgaagccat | accaaacgac | gagcgtgaca | ccacgatgcc | tgtagcaatg | gcaacaacgt | 6180 |
| tgcgcaaact | attaactggc | gaactactta | ctctagcttc | ccggcaacaa | ttaatagact | 6240 |
| ggatggaggc | ggataaagtt | gcaggaccac | ttctgcgctc | ggcccttccg | gctggctggt | 6300 |
| ttattgctga | taaatctgga | gccggtgagc | gtgggtctcg | cggtatcatt | gcagcactgg | 6360 |
| ggccagatgg | taagccctcc | cgtatcgtag | ttatctacac | gacggggagt | caggcaacta | 6420 |
| tggatgaacg | aaatagacag | atcgctgaga | taggtgcctc | actgattaag | cattggtaac | 6480 |
| tgtcagacca | agtttactca | tatatacttt | agattgattt | aaaacttcat | ttttaattta | 6540 |
| aaaggatcta | ggtgaagatc | ctttttgata | atctcatgac | caaaatccct | taacgtgagt | 6600 |
| tttcgttcca | ctgagcgtca | gaccccgtag | aaaagatcaa | aggatcttct | tgagatcctt | 6660 |
| tttttctgcg | cgtaatctgc | tgcttgcaaa | caaaaaaacc | accgctacca | gcggtggttt | 6720 |
| gtttgccgga | tcaagagcta | ccaactcttt | ttccgaaggt | aactggcttc | agcagagcgc | 6780 |
| agataccaaa | tactgttctt | ctagtgtagc | cgtagttagg | ccaccacttc | aagaactctg | 6840 |
| tagcaccgcc | tacatacctc | gctctgctaa | tcctgttacc | agtggctgct | gccagtggcg | 6900 |
| ataagtcgtg | tcttaccggg | ttggactcaa | gacgatagtt | accggataag | gcgcagcggt | 6960 |
| cgggctgaac | ggggggttcg | tgcacacagc | ccagcttgga | gcgaacgacc | tacaccgaac | 7020 |
| tgagatacct | acagcgtgag | ctatgagaaa | gcgccacgct | tcccgaagag | agaaaggcgg | 7080 |
| acaggtatcc | ggtaagcggc | agggtcggaa | caggagagcg | cacgagggag | cttccagggg | 7140 |
| gaaacgcctg | gtatctttat | agtcctgtcg | ggtttcgcca | cctctgactt | gagcgtcgat | 7200 |
| ttttgtgatg | ctcgtcaggg | gggcggagcc | tatggaaaaa | cgccagcaac | gcggcctttt | 7260 |
| tacggttcct | ggccttttgc | tggccttttg | ctcacatgtt | ctttcctgcg | ttatcccctg | 7320 |
| attctgtgga | taaccgtatt | accgcctttg | agtgagctga | taccgctcgc | cgcagccgaa | 7380 |
| cgaccgagcg | cagcgagtca | gtgagcgagg | aagcggaaga | gcgcccaata | cgcaaaccgc | 7440 |
| ctctccccgc | gcgttggccg | attcattaat | gcagctggca | cgacaggttt | cccgactgga | 7500 |
| aagcgggcag | tgagcgcaac | gcaattaatg | tgagttagct | cactcattag | gcaccccagg | 7560 |
| ctttacactt | tatgcttccg | gctcgtatgt | tgtgtggaat | tgtgagcgga | taacaatttc | 7620 |
| acacaggaaa | cagctatgac | catgattacg | ccaagcgcgc | aattaaccct | cactaaaggg | 7680 |
| aacaaaagct | ggagctgcaa | gctt | | | | 7704 |

<210> SEQ ID NO 13
<211> LENGTH: 7250
<212> TYPE: DNA
<213> ORGANISM: Artificial Sequence
<220> FEATURE:
<223> OTHER INFORMATION: Synthetic lentiviral vector

<400> SEQUENCE: 13

| aatgtagtct | tatgcaatac | tcttgtagtc | ttgcaacatg | gtaacgatga | gttagcaaca | 60 |
| tgccttacaa | ggagagaaaa | agcaccgtgc | atgccgattg | gtggaagtaa | ggtggtacga | 120 |
| tcgtgcctta | ttaggaaggc | aacagacggg | tctgacatgg | attggacgaa | ccactgaatt | 180 |
| gccgcattgc | agagatattg | tatttaagtg | cctagctcga | tacataaacg | ggtctctctg | 240 |

```
gttagaccag atctgagcct gggagctctc tggctaacta gggaacccac tgcttaagcc    300
tcaataaagc ttgccttgag tgcttcaagt agtgtgtgcc cgtctgttgt gtgactctgg    360
taactagaga tccctcagac cctttagtc agtgtggaaa atctctagca gtggcgcccg    420
aacagggact tgaaagcgaa agggaaacca gaggagctct ctcgacgcag gactcggctt    480
gctgaagcgc gcacggcaag aggcgagggg cggcgactgg tgagtacgcc aaaaattttg    540
actagcggag gctagaagga gagagatggg tgcgagagcg tcagtattaa gcggggagaa    600
attagatcgc gatgggaaaa aattcggtta aggccagggg gaaagaaaaa atataaatta    660
aaacatatag tatgggcaag cagggagcta gaacgattcg cagttaatcc tggcctgtta    720
gaaacatcag aaggctgtag acaaatactg ggacagctac aaccatccct tcagacagga    780
tcagaagaac ttagatcatt atataataca gtagcaaccc tctattgtgt gcatcaaagg    840
atagagataa aagacaccaa ggaagcttta acaagatag aggaagagca aaacaaaagt    900
aagaccaccg cacagcaagc ggccgctgat cttcagacct ggaggaggag atatgaggga    960
caattggaga agtgaattat ataaatataa agtagtaaaa attgaaccat taggagtagc   1020
acccaccaag gcaaagagaa gagtggtgca gagagaaaaa agagcagtgg gaataggagc   1080
tttgttcctt gggttcttgg gagcagcagg aagcactatg ggcgcagcgt caatgacgct   1140
gacggtacag gccagacaat tattgtctgg tatagtgcag cagcagaaca atttgctgag   1200
ggctattgag gcgcaacagc atctgttgca actcacagtc tggggcatca agcagctcca   1260
ggcaagaatc ctggctgtgg aaagatacct aaaggatcaa cagctcctgg ggatttgggg   1320
ttgctctgga aaactcattt gcaccactgc tgtgccttgg aatgctagtt ggagtaataa   1380
atctctggaa cagatttgga atcacacgac ctggatggag tgggacagag aaattaacaa   1440
ttacacaagc ttaatacact ccttaattga agaatcgcaa aaccagcaag aaaagaatga   1500
acaagaatta ttggaattag ataaatgggc aagtttgtgg aattggttta acataacaaa   1560
ttggctgtgg tatataaaat tattcataat gatagtagga ggcttggtag gtttaagaat   1620 agttttgct gtactttcta tagtgaatag agttaggcag ggatattcac cattatcgtt   1680
tcagacccac ctcccaaccc cgaggggacc cgacaggccc gaaggaatag aagaagaagg   1740
tggagagaga gacagagaca gatccattcg attagtgaac ggatctcgac ggtatcgcta   1800
gcttttaaaa gaaaaggggg gattggggggg tacagtgcag gggaagaat agtagacata   1860 atagcaacag acatacaaac taaagaatta caaaaacaaa ttacaaaaat tcaaaatttt   1920
actagtgatt atcggatcaa ctttgtatag aaaagttgct gtggaatgtg tgtcagttag   1980
ggtgtggaaa gtccccaggc tccccagcag gcagaagtat gcaaagcatg catctcaatt   2040
agtcagcaac caggtgtgga agtccccag gctcccagc aggcagaagt atgcaaagca   2100
tgcatctcaa ttagtcagca accatagtcc cgcccctaac tccgcccatc ccgcccctaa   2160
ctccgcccag ttccgcccat tctccgcccc atggctgact aatttttttt atttatgcag   2220
aggccgaggc cgcctctgcc tctgagctat tccagaagta gtgaggaggc ttttttggag   2280
gcctaggctt ttgcaaaaag ctcaagtttg tacaaaaaag caggctgcca ccatggtgag   2340
caagggcgag gagctgttca ccggggtggt gcccatcctg gtcgagctgg acggcgacgt   2400
aaacggccac aagttcagcg tgtccggcga gggcgagggc gatgccacct acggcaagct   2460
gaccctgaag ttcatctgca ccaccggcaa gctgcccgtg ccctggccca ccctcgtgac   2520 cacccctgacc tacggcgtgc agtgcttcag ccgctacccc gaccacatga agcagcacga   2580
```

```
cttcttcaag tccgccatgc ccgaaggcta cgtccaggag cgcaccatct tcttcaagga    2640
cgacggcaac tacaagaccc gcgccgaggt gaagttcgag ggcgacaccc tggtgaaccg    2700
catcgagctg aagggcatcg acttcaagga ggacggcaac atcctggggc acaagctgga    2760
gtacaactac aacagccaca acgtctatat catggccgac aagcagaaga acggcatcaa    2820
ggtgaacttc aagatccgcc acaacatcga ggacggcagc gtgcagctcg ccgaccacta    2880
ccagcagaac acccccatcg gcgacggccc cgtgctgctg cccgacaacc actacctgag    2940
cacccagtcc gccctgagca agaccccaa cgagaagcgc gatcacatgg tcctgctgga    3000
gttcgtgacc gccgccggga tcactctcgg catggacgag ctgtacaagt aaacccagct    3060
ttcttgtaca agtggtgat aatcgaattc cgataatcaa cctctggatt acaaaatttg    3120
tgaaagattg actggtattc ttaactatgt tgctccttt acgctatgtg gatacgctgc    3180
tttaatgcct ttgtatcatg ctattgcttc ccgtatggct ttcatttct cctccttgta    3240 taaatcctgg ttgctgtctc tttatgagga gttgtggccc gttgtcaggc aacgtggcgt    3300
ggtgtgcact gtgtttgctg acgcaacccc cactggttgg ggcattgcca ccacctgtca    3360
gctcctttcc gggactttcg ctttccccct cctattgcc acggcggaac tcatcgccgc    3420
ctgccttgcc cgctgctgga cagggctcg gctgttgggc actgacaatt ccgtggtgtt    3480
gtcggggaag ctgacgtcct ttccatggct gctcgcctgt gttgccacct ggattctgcg    3540
cgggacgtcc ttctgctacg tcccttcggc cctcaatcca gcggacctc cttcccgcgg    3600 cctgctgccg gctctgcggc ctcttccgcg tcttcgcctt cgccctcaga cgagtcggat    3660 ctcccttttgg gccgcctccc cgcatcggga attcccgcgg ttcgctttaa gaccaatgac    3720
ttacaaggca gctgtagatc ttagccactt tttaaaagaa aagggggac tggaagggct    3780 aattcactcc caacgaagac aagatctgct ttttgcttgt actgggtctc tctggttaga    3840
ccagatctga gcctgggagc tctctggcta actagggaac ccactgctta agcctcaata    3900
aagcttgcct tgagtgcttc aagtagtgtg tgcccgtctg ttgtgtgact ctggtaacta    3960
gagatccctc agacccttt agtcagtgtg gaaaatctct agcagtagta gttcatgtca    4020
tcttattatt cagtatttat aacttgcaaa gaaatgaata tcagagagtg agaggaactt    4080
gtttattgca gcttataatg gttacaaata aagcaatagc atcacaaatt cacaaataa    4140 agcattttt tcactgcatt ctagttgtgg tttgtccaaa ctcatcaatg tatcttatca    4200
tgtctggctc tagctatccc gccctaact ccgcccatcc cgccctaac tccgcccagt    4260 tccgcccatt ctccgcccca tggctgacta atttttttta tttatgcaga ggccgaggcc    4320
gcctcggcct ctgagctatt ccagaagtag tgaggaggct ttttggagg cctagggacg    4380 tacccaattc gccctatagt gagtcgtatt acgcgcgctc actggccgtc gttttacaac    4440
gtcgtgactg ggaaaaccct ggcgttaccc aacttaatcg ccttgcagca catccccctt    4500
tcgccagctg gcgtaatagc gaagaggccc gcaccgatcg cccttcccaa cagttgcgca    4560
gcctgaatgg cgaatgggac gcgccctgta gcggcgcatt aagcgcggcg ggtgtggtgg    4620
ttacgcgcag cgtgaccgct acacttgcca gcgccctagc gcccgctcct ttcgctttct    4680
tcccttcctt tctcgccacg ttcgccggct tccccgtca gctctaaat cggggctcc    4740 ctttagggtt ccgatttagt gctttacggc acctcgaccc caaaaaactt gattagggtg    4800
atggttcacg tagtgggcca tcgccctgat agacggtttt tcgccctttg acgttggagt    4860
ccacgttctt taatagtgga ctcttgttcc aaactggaac aacactcaac cctatctcgg    4920
tctattcttt tgatttataa gggattttgc cgatttcggc ctattggtta aaaaatgagc    4980
```

```
tgatttaaca aaaatttaac gcgaattttta acaaaatatt aacgcttaca atttaggtgg      5040 cactttttcgg ggaaatgtgc gcggaacccc tatttgttta tttttctaaa tacattcaaa      5100
tatgtatccg ctcatgagac aataaccctg ataaatgctt caataatatt gaaaaaggaa      5160
gagtatgagt attcaacatt tccgtgtcgc ccttattccc ttttttgcgg cattttgcct      5220
tcctgttttt gctcacccag aaacgctggt gaaagtaaaa gatgctgaag atcagttggg      5280
tgcacgagtg ggttacatcg aactggatct caacagcggt aagatccttg agagttttcg      5340
ccccgaagaa cgttttccaa tgatgagcac ttttaaagtt ctgctatgtg gcgcggtatt      5400
atcccgtatt gacgccgggc aagagcaact cggtcgccgc atacactatt ctcagaatga      5460
cttggttgag tactcaccag tcacagaaaa gcatcttacg gatggcatga cagtaagaga      5520
attatgcagt gctgccataa ccatgagtga taacactgcg gccaacttac ttctgacaac      5580
gatcggagga ccgaaggagc taaccgcttt tttgcacaac atgggggatc atgtaactcg      5640
ccttgatcgt tgggaaccgg agctgaatga agccatacca aacgacgagc gtgacaccac      5700
gatgcctgta gcaatggcaa caacgttgcg caaactatta actggcgaac tacttactct      5760
agcttcccgg caacaattaa tagactggat ggaggcggat aaagttgcag gaccacttct      5820
gcgctcggcc cttccggctg gctggtttat tgctgataaa tctggagccg gtgagcgtgg      5880
gtctcgcggt atcattgcag cactggggcc agatggtaag ccctcccgta tcgtagttat      5940
ctacacgacg gggagtcagg caactatgga tgaacgaaat agacagatcg ctgagatagg      6000
tgcctcactg attaagcatt ggtaactgtc agaccaagtt tactcatata ctttagat      6060 tgatttaaaa cttcattttt aatttaaaag gatctaggtg aagatccttt ttgataatct      6120
catgaccaaa atcccttaac gtgagttttc gttccactga gcgtcagacc ccgtagaaaa      6180
gatcaaagga tcttcttgag atcctttttt tctgcgcgta atctgctgct tgcaaacaaa      6240
aaaaccaccg ctaccagcgg tggtttgttt gccggatcaa gagctaccaa ctctttttcc      6300
gaaggtaact ggcttcagca gagcgcagat accaaatact gttcttctag tgtagccgta      6360
gttaggccac cacttcaaga actctgtagc accgcctaca tacctcgctc tgctaatcct      6420
gttaccagtg gctgctgcca gtggcgataa gtcgtgtctt accgggttgg actcaagacg      6480
atagttaccg gataaggcgc agcggtcggg ctgaacgggg ggttcgtgca cacagcccag      6540
cttggagcga acgacctaca ccgaactgag atacctacag cgtgagctat gagaaagcgc      6600
cacgcttccc gaagagagaa aggcggacag gtatccggta agcggcaggg tcggaacagg      6660
agagcgcacg agggagcttc cagggggaaa cgcctggtat ctttatagtc ctgtcgggtt      6720
tcgccacctc tgacttgagc gtcgattttt gtgatgctcg tcaggggggc ggagcctatg      6780
gaaaaacgcc agcaacgcgg cctttttacg gttcctggcc ttttgctggc cttttgctca      6840
catgttcttt cctgcgttat cccctgattc tgtggataac cgtattaccg cctttgagtg      6900
agctgatacc gctcgccgca gccgaacgac cgagcgcagc gagtcagtga gcgaggaagc      6960
ggaagagcgc ccaatacgca aaccgcctct ccccgcgcgt tggccgattc attaatgcag      7020
ctggcacgac aggtttcccg actggaaagc gggcagtgag cgcaacgcaa ttaatgtgag      7080
ttagctcact cattaggcac cccaggcttt acactttatg cttccggctc gtatgttgtg      7140
tggaattgtg agcggataac aatttcacac aggaaacagc tatgaccatg attacgccaa      7200
gcgcgcaatt aaccctcact aaagggaaca aaagctggag ctgcaagctt              7250
```

<210> SEQ ID NO 14

<211> LENGTH: 7417
<212> TYPE: DNA
<213> ORGANISM: Artificial Sequence
<220> FEATURE:
<223> OTHER INFORMATION: Synthetic lentiviral vector

<400> SEQUENCE: 14

| | | | | | |
|---|---|---|---|---|---|
| aatgtagtct | tatgcaatac | tcttgtagtc | ttgcaacatg | gtaacgatga | gttagcaaca | 60 |
| tgccttacaa | ggagagaaaa | agcaccgtgc | atgccgattg | gtggaagtaa | ggtggtacga | 120 |
| tcgtgcctta | ttaggaaggc | aacagacggg | tctgacatgg | attggacgaa | ccactgaatt | 180 |
| gccgcattgc | agagatattg | tatttaagtg | cctagctcga | tacataaacg | ggtctctctg | 240 |
| gttagaccag | atctgagcct | gggagctctc | tggctaacta | gggaacccac | tgcttaagcc | 300 |
| tcaataaagc | ttgccttgag | tgcttcaagt | agtgtgtgcc | cgtctgttgt | gtgactctgg | 360 |
| taactagaga | tccctcagac | ccttttagtc | agtgtggaaa | atctctagca | gtggcgcccg | 420 |
| aacagggact | tgaaagcgaa | agggaaacca | gaggagctct | ctcgacgcag | gactcggctt | 480 |
| gctgaagcgc | gcacggcaag | aggcgagggg | cggcgactgg | tgagtacgcc | aaaaattttg | 540 |
| actagcggag | gctagaagga | gagagatggg | tgcgagagcg | tcagtattaa | gcggggggaga | 600 |
| attagatcgc | gatgggaaaa | aattcggtta | aggccagggg | gaaagaaaaa | atataaatta | 660 |
| aaacatatag | tatgggcaag | cagggagcta | gaacgattcg | cagttaatcc | tggcctgtta | 720 |
| gaaacatcag | aaggctgtag | acaaatactg | ggacagctac | aaccatccct | tcagacagga | 780 |
| tcagaagaac | ttagatcatt | atataataca | gtagcaaccc | tctattgtgt | gcatcaaagg | 840 |
| atagagataa | aagacaccaa | ggaagcttta | gacaagatag | aggaagagca | aaacaaaagt | 900 |
| aagaccaccg | cacagcaagc | ggccgctgat | cttcagacct | ggaggaggag | atatgaggga | 960 |
| caattggaga | agtgaattat | ataaatataa | agtagtaaaa | attgaaccat | taggagtagc | 1020 |
| acccaccaag | gcaaagagaa | gagtggtgca | gagagaaaaa | agagcagtgg | gaataggagc | 1080 |
| tttgttcctt | gggttcttgg | gagcagcagg | aagcactatg | ggcgcagcgt | caatgacgct | 1140 |
| gacggtacag | gccagacaat | tattgtctgg | tatagtgcag | cagcagaaca | atttgctgag | 1200 |
| ggctattgag | gcgcaacagc | atctgttgca | actcacagtc | tggggcatca | agcagctcca | 1260 |
| ggcaagaatc | ctggctgtgg | aaagatacct | aaaggatcaa | cagctcctgg | ggatttgggg | 1320 |
| ttgctctgga | aaactcattt | gcaccactgc | tgtgccttgg | aatgctagtt | ggagtaataa | 1380 |
| atctctggaa | cagatttgga | atcacacgac | ctggatggag | tgggacagag | aaattaacaa | 1440 |
| ttacacaagc | ttaatacact | ccttaattga | agaatcgcaa | aaccagcaag | aaaagaatga | 1500 |
| acaagaatta | ttggaattag | ataaatgggc | aagtttgtgg | aattggttta | acataacaaa | 1560 |
| ttggctgtgg | tatataaaat | tattcataat | gatagtagga | ggcttggtag | gtttaagaat | 1620 |
| agtttttgct | gtactttcta | tagtgaatag | agttaggcag | ggatattcac | cattatcgtt | 1680 |
| tcagacccac | ctcccaaccc | cgaggggacc | cgacaggccc | gaaggaatag | aagaagaagg | 1740 |
| tggagagaga | gacagagaca | gatccattcg | attagtgaac | ggatctcgac | ggtatcgcta | 1800 |
| gcttttaaaa | gaaaaggggg | gattgggggg | tacagtgcag | gggaaagaat | agtagacata | 1860 |
| atagcaacag | acatacaaac | taagaatta | caaaaacaaa | ttacaaaaat | tcaaaatttt | 1920 |
| actagtgatt | atcggatcaa | cttttgtatag | aaaagttgtt | ctaccgggta | ggggaggcgc | 1980 |
| ttttcccaag | gcagtctgga | gcatgcgctt | tagcagcccc | gctgggcact | tggcgctaca | 2040 |
| caagtggcct | ctggcctcgc | acacattcca | catccaccgg | taggcgccaa | ccggctccgt | 2100 |
| tctttggtgg | cccccttcgcg | ccaccttcta | ctcctccccct | agtcaggaag | ttcccccccg | 2160 |

```
ccccgcagct cgcgtcgtgc aggacgtgac aaatggaagt agcacgtctc actagtctcg    2220
tgcagatgga cagcaccgct gagcaatgga agcgggtagg cctttggggc agcggccaat    2280
agcagctttg ctccttcgct ttctgggctc agaggctggg aaggggtggg tccggggggcg   2340 ggctcagggg cgggctcagg ggcggggcgg gcgcccgaag gtcctccgga ggcccggcat    2400
tctgcacgct tcaaaagcgc acgtctgccg cgctgttctc ctcttcctca tctccgggcc    2460
tttcgacctc aagtttgtac aaaaaagcag gctgccacca tggtgagcaa gggcgaggag    2520
ctgttcaccg gggtggtgcc catcctggtc gagctggacg gcgacgtaaa cggccacaag    2580
ttcagcgtgt ccggcgaggg cgagggcgat gccacctacg gcaagctgac cctgaagttc    2640
atctgcacca ccggcaagct gcccgtgccc tggcccaccc tcgtgaccac cctgacctac    2700
ggcgtgcagt gcttcagccg ctaccccgac cacatgaagc agcacgactt cttcaagtcc    2760
gccatgcccg aaggctacgt ccaggagcgc accatcttct tcaaggacga cggcaactac    2820
aagacccgcg ccgaggtgaa gttcgagggc gacaccctgg tgaaccgcat cgagctgaag    2880
ggcatcgact tcaaggagga cggcaacatc ctggggcaca agctggagta caactacaac    2940
agccacaacg tctatatcat ggccgacaag cagaagaacg gcatcaaggt gaacttcaag    3000
atccgccaca acatcgagga cggcagcgtg cagctcgccg accactacca gcagaacacc    3060
cccatcggcg acggccccgt gctgctgccc gacaaccact acctgagcac ccagtccgcc    3120
ctgagcaaag accccaacga aagcgcgat cacatggtcc tgctggagtt cgtgaccgcc    3180
gccgggatca ctctcggcat ggacgagctg tacaagtaaa cccagctttc ttgtacaaag    3240
tggtgataat cgaattccga taatcaacct ctggattaca aaatttgtga agattgact    3300 ggtattctta actatgttgc tcctttacg ctatgtggat acgctgcttt aatgcctttg    3360
tatcatgcta ttgcttcccg tatggctttc attttctcct ccttgtataa atcctggttg    3420
ctgtctcttt atgaggagtt gtggcccgtt gtcaggcaac gtggcgtggt gtgcactgtg    3480
tttgctgacg caacccccac tggttggggc attgccacca cctgtcagct cctttccggg    3540
actttcgctt tccccctccc tattgccacg gcggaactca tcgccgcctg ccttgcccgc    3600
tgctggacag gggctcggct gttgggcact gacaattccg tggtgttgtc ggggaagctg    3660
acgtcctttc catggctgct cgcctgtgtt gccacctgga ttctgcgcgg gacgtccttc    3720
tgctacgtcc cttcggccct caatccagcg gaccttcctt cccgcggcct gctgccggct    3780
ctgcggcctc ttccgcgtct tcgccttcgc cctcagacga gtcggatctc cctttgggcc    3840
gcctccccgc atcgggaatt cccgcggttc gctttaagac caatgactta caaggcagct    3900
gtagatctta gccactttt aaaagaaaag ggggactgg aagggctaat tcactcccaa    3960
cgaagacaag atctgctttt tgcttgtact gggtctctct ggttagacca gatctgagcc   4020
tgggagctct ctggctaact agggaaccca ctgcttaagc ctcaataaag cttgccttga   4080
gtgcttcaag tagtgtgtgc ccgtctgttg tgtgactctg gtaactagag atccctcaga   4140
cccttttagt cagtgtggaa aatctctagc agtagtagtt catgtcatct tattattcag   4200
tatttataac ttgcaaagaa atgaatatca gagagtgaga ggaacttgtt tattgcagct   4260
tataatggtt acaaataaag caatagcatc acaaatttca caaataaagc attttttca    4320 ctgcattcta gttgtggttt gtccaaactc atcaatgtat cttatcatgt ctggctctag   4380
ctatcccgcc cctaactccg cccatcccgc cctaactccg cccagttccg cccattctc    4440 cgccccatgg ctgactaatt ttttttattt atgcagaggc cgaggccgcc tcggcctctg   4500
```

```
agctattcca gaagtagtga ggaggctttt ttggaggcct agggacgtac ccaattcgcc    4560
ctatagtgag tcgtattacg cgcgctcact ggccgtcgtt ttacaacgtc gtgactggga    4620
aaaccctggc gttacccaac ttaatcgcct tgcagcacat ccccctttcg ccagctggcg    4680
taatagcgaa gaggcccgca ccgatcgccc ttcccaacag ttgcgcagcc tgaatggcga    4740
atgggacgcg ccctgtagcg gcgcattaag cgcggcgggt gtggtggtta cgcgcagcgt    4800
gaccgctaca cttgccagcg ccctagcgcc cgctcctttc gctttcttcc cttcctttct    4860
cgccacgttc gccggctttc cccgtcaagc tctaaatcgg gggctccctt tagggttccg    4920
atttagtgct ttacggcacc tcgaccccaa aaaacttgat tagggtgatg gttcacgtag    4980
tgggccatcg ccctgataga cggttttttcg ccctttgacg ttggagtcca cgttctttaa    5040
tagtggactc ttgttccaaa ctggaacaac actcaaccct atctcggtct attcttttga    5100
tttataaggg attttgccga tttcggccta ttggttaaaa aatgagctga tttaacaaaa    5160
atttaacgcg aattttaaca aaatattaac gcttacaatt taggtggcac ttttcgggga    5220
aatgtgcgcg gaaccccctat ttgtttattt ttctaaatac attcaaatat gtatccgctc    5280
atgagacaat aaccctgata aatgcttcaa taatattgaa aaaggaagag tatgagtatt    5340
caacatttcc gtgtcgccct tattccctttt tttgcggcat tttgccttcc tgttttttgct   5400
cacccagaaa cgctggtgaa agtaaaagat gctgaagatc agttgggtgc acgagtgggt    5460
tacatcgaac tggatctcaa cagcggtaag atccttgaga gttttcgccc cgaagaacgt    5520
tttccaatga tgagcacttt taaagttctg ctatgtggcg cggtattatc ccgtattgac    5580
gccgggcaag agcaactcgg tcgccgcata cactattctc agaatgactt ggttgagtac    5640
tcaccagtca cagaaaagca tcttacggat ggcatgacag taagagaatt atgcagtgct    5700
gccataacca tgagtgataa cactgcggcc aacttacttc tgacaacgat cggaggaccg    5760
aaggagctaa ccgcttttttt gcacaacatg ggggatcatg taactcgcct tgatcgttgg    5820
gaaccggagc tgaatgaagc cataccaaac gacgagcgtg acaccacgat gcctgtagca    5880
atggcaacaa cgttgcgcaa actattaact ggcgaactac ttactctagc ttcccggcaa    5940
caattaatag actggatgga gcggataaaa gttgcaggac cacttctgcg ctcggccctt    6000
ccggctggct ggtttattgc tgataaatct ggagccggtg agcgtgggtc tcgcggtatc    6060
attgcagcac tggggccaga tggtaagccc tcccgtatcg tagttatcta cacgacgggg    6120
agtcaggcaa ctatggatga acgaaataga cagatcgctg agataggtgc ctcactgatt    6180
aagcattggt aactgtcaga ccaagtttac tcatatatac tttagattga tttaaaactt    6240
cattttttaat ttaaaaggat ctaggtgaag atccttttttg ataatctcat gaccaaaatc    6300
ccttaacgtg agttttcgtt ccactgagcg tcagaccccg tagaaaagat caaaggatct    6360
tcttgagatc cttttttttct gcgcgtaatc tgctgcttgc aaacaaaaaa accaccgcta    6420
ccagcggtgg tttgtttgcc ggatcaagag ctaccaactc tttttccgaa ggtaactggc    6480
ttcagcagag cgcagatacc aaatactgtt cttctagtgt agccgtagtt aggccaccac    6540
ttcaagaact ctgtagcacc gcctacatac ctcgctctgc taatcctgtt accagtggct    6600
gctgccagtg gcgataagtc gtgtcttacc gggttggact caagacgata gttaccggat    6660
aaggcgcagc ggtcgggctg aacggggggt tcgtgcacac agcccagctt ggagcgaacg    6720
acctacaccg aactgagata cctacagcgt gagctatgag aaagcgccac gcttcccgaa    6780
gagagaaagg cggacaggta tccggtaagc ggcagggtcg gaacaggaga gcgcacgagg    6840
gagcttccag ggggaaacgc ctggtatctt tatagtcctg tcgggtttcg ccacctctga    6900
```

```
cttgagcgtc gattttgtg atgctcgtca gggggcgga gcctatggaa aaacgccagc    6960
aacgcggcct ttttacggtt cctggccttt tgctggcctt ttgctcacat gttctttcct    7020
gcgttatccc ctgattctgt ggataaccgt attaccgcct ttgagtgagc tgataccgct    7080
cgccgcagcc gaacgaccga gcgcagcgag tcagtgagcg aggaagcgga gagcgccca     7140 atacgcaaac cgcctctccc cgcgcgttgg ccgattcatt aatgcagctg gcacgacagg    7200
tttcccgact ggaaagcggg cagtgagcgc aacgcaatta atgtgagtta gctcactcat    7260
taggcacccc aggctttaca ctttatgctt ccggctcgta tgttgtgtgg aattgtgagc    7320
ggataacaat ttcacacagg aaacagctat gaccatgatt acgccaagcg cgcaattaac    7380
cctcactaaa gggaacaaaa gctggagctg caagctt                             7417
```

<210> SEQ ID NO 15
<211> LENGTH: 8084
<212> TYPE: DNA
<213> ORGANISM: Artificial Sequence
<220> FEATURE:
<223> OTHER INFORMATION: Synthetic lentiviral vector

<400> SEQUENCE: 15

```
aatgtagtct tatgcaatac tcttgtagtc ttgcaacatg gtaacgatga gttagcaaca      60
tgccttacaa ggagagaaaa agcaccgtgc atgccgattg gtggaagtaa ggtggtacga     120
tcgtgcctta ttaggaaggc aacagacggg tctgacatgg attggacgaa ccactgaatt    180
gccgcattgc agagatattg tatttaagtg cctagctcga tacataaacg ggtctctctg    240
gttagaccag atctgagcct gggagctctc tggctaacta gggaacccac tgcttaagcc    300
tcaataaagc ttgccttgag tgcttcaagt agtgtgtgcc cgtctgttgt gtgactctgg    360
taactagaga tccctcagac ccttttagtc agtgtggaaa atctctagca gtggcgcccg    420
aacagggact tgaaagcgaa agggaaacca gaggagctct ctcgacgcag gactcggctt    480
gctgaagcgc gcacggcaag aggcgagggg cggcgactgg tgagtacgcc aaaaattttg    540
actagcggag gctagaagga gagagatggg tgcgagagcg tcagtattaa gcggggagaa    600
attagatcgc gatgggaaaa aattcggtta aggccagggg gaagaaaaa atataaatta     660 aaacatatag tatgggcaag cagggagcta gaacgattcg cagttaatcc tggcctgtta    720
gaaacatcag aaggctgtag acaaatactg ggacagctac aaccatccct tcagacagga    780
tcagaagaac ttagatcatt atataataca gtagcaaccc tctattgtgt gcatcaaagg    840
atagagataa aagacaccaa ggaagcttta gacaagatag aggaagagca aaacaaaagt    900
aagaccaccg cacagcaagc ggccgctgat cttcagacct ggaggaggag atatgaggga    960
caattggaga agtgaattat ataaatataa agtagtaaaa attgaaccat taggagtagc   1020
acccaccaag gcaaagagaa gagtggtgca gagagaaaaa agagcagtgg gaataggagc   1080
tttgttcctt gggttcttgg gagcagcagg aagcactatg ggcgcagcgt caatgacgct   1140
gacggtacag gccagacaat tattgtctgg tatagtgcag cagcagaaca atttgctgag   1200
ggctattgag gcgcaacagc atctgttgca actcacagtc tggggcatca agcagctcca   1260
ggcaagaatc ctggctgtgg aaagatacct aaaggatcaa cagctcctgg ggatttgggg   1320
ttgctctgga aaactcattt gcaccactgc tgtgccttgg aatgctagtt ggagtaataa   1380
atctctggaa cagatttgga atcacacgac ctggatggag tgggacagag aaattaacaa   1440
ttacacaagc ttaatacact ccttaattga agaatcgcaa aaccagcaag aaaagaatga   1500
```

```
acaagaatta ttggaattag ataaatgggc aagtttgtgg aattggttta acataacaaa    1560
ttggctgtgg tatataaaat tattcataat gatagtagga ggcttggtag gtttaagaat    1620 agttttgct gtactttcta tagtgaatag agttaggcag ggatattcac cattatcgtt     1680
tcagacccac ctcccaaccc cgaggggacc cgacaggccc gaaggaatag aagaagaagg    1740
tggagagaga gacagagaca gatccattcg attagtgaac ggatctcgac ggtatcgcta    1800
gcttttaaaa gaaaaggggg gattgggggg tacagtgcag gggaaagaat agtagacata    1860
atagcaacag acatacaaac taagaattca caaaacaaa ttacaaaaat tcaaaatttt     1920
actagtgatt atcggatcaa ctttgtatag aaaagttggg tgcagcggcc tccgcgccgg    1980
gttttggcgc ctcccgcggg cgccccctc ctcacggcga gcgctgccac gtcagacgaa     2040
gggcgcagcg agcgtcctga tccttccgcc cggacgctca ggacagcggc ccgctgctca    2100
taagactcgg ccttagaacc ccagtatcag cagaaggaca ttttaggacg ggacttgggt    2160
gactctaggg cactggtttt ctttccagag agcggaacag gcgaggaaaa gtagtcccct    2220
ctcggcgatt ctgcggaggg atctccgtgg ggcggtgaac gccgatgatt atataaggac    2280
gcgccgggtg tggcacagct agttccgtcg cagccgggat ttgggtcgcg gttcttgttt    2340
gtggatcgct gtgatcgtca cttggtgagt agcgggctgc tgggctggcc ggggcttttcg   2400 tggccgccgg gccgctcggt gggacggaag cgtgtggaga gaccgccaag ggctgtagtc    2460
tgggtccgcg agcaaggttg ccctgaactg ggggttgggg ggagcgcagc aaaatggcgg    2520
ctgttcccga gtcttgaatg gaagacgctt gtgaggcggg ctgtgaggtc gttgaaacaa    2580 ggtgggggc atggtgggcg gcaagaaccc aaggtcttga ggccttcgct aatgcgggaa     2640
agctcttatt cgggtgagat gggctggggc accatctggg gaccctgacg tgaagtttgt    2700
cactgactgg agaactcggt ttgtcgtctg ttgcgggggc ggcagttatg gcggtgccgt    2760
tgggcagtgc acccgtacct ttgggagcgc gcgccctcgt cgtgtcgtga cgtcacccgt    2820
tctgttggct tataatgcag ggtgggggcca cctgccggta ggtgtgcggt aggcttttct    2880
ccgtcgcagg acgcagggtt cgggcctagg gtaggctctc ctgaatcgac aggcgccgga    2940
cctctggtga ggggagggat aagtgaggcg tcagtttctt tggtcggttt tatgtaccta    3000
tcttcttaag tagctgaagc tccggttttg aactatgcgc tcggggttgg cgagtgtgtt    3060
ttgtgaagtt ttttaggcac cttttgaaat gtaatcattt gggtcaatat gtaattttca    3120
gtgttagact agtaaacaag tttgtacaaa aaagcaggct gccaccatgg tgagcaaggg    3180
cgaggagctg ttcaccgggg tggtgcccat cctggtcgag ctggacggcg acgtaaacgg    3240
ccacaagttc agcgtgtccg gcgagggcga gggcgatgcc acctacggca agctgaccct    3300
gaagttcatc tgcaccaccg gcaagctgcc cgtgccctgg cccaccctcg tgaccaccct    3360
gacctacggc gtgcagtgct tcagccgcta ccccgaccac atgaagcagc acgacttctt    3420
caagtccgcc atgcccgaag gctacgtcca ggagcgcacc atcttcttca aggacgacgg    3480
caactacaag acccgcgccg aggtgaagtt cgagggcgac accctggtga accgcatcga    3540
gctgaagggc atcgacttca aggaggacgg caacatcctg gggcacaagc tggagtacaa    3600
ctacaacagc cacaacgtct atatcatggc cgacaagcag aagaacggca tcaaggtgaa    3660
cttcaagatc cgccacaaca tcgaggacgg cagcgtgcag ctcgccgacc actaccagca    3720 gaacacccccc atcggcgacg gccccgtgct gctgcccgac aaccactacc tgagcaccca    3780
gtccgccctg agcaaagacc ccaacgagaa gcgcgatcac atggtcctgc tggagttcgt    3840
gaccgccgcc gggatcactc tcggcatgga cgagctgtac aagtaaaccc agctttcttg    3900
```

```
tacaaagtgg tgataatcga attccgataa tcaacctctg gattacaaaa tttgtgaaag    3960
attgactggt attcttaact atgttgctcc ttttacgcta tgtggatacg ctgctttaat    4020
gcctttgtat catgctattg cttcccgtat ggctttcatt ttctcctcct tgtataaatc    4080
ctggttgctg tctctttatg aggagttgtg gcccgttgtc aggcaacgtg gcgtggtgtg    4140
cactgtgttt gctgacgcaa ccccactgg ttggggcatt gccaccacct gtcagctcct    4200
ttccgggact ttcgctttcc ccctccctat gccacggcg gaactcatcg ccgcctgcct    4260
tgcccgctgc tggacagggg ctcggctgtt gggcactgac aattccgtgg tgttgtcggg    4320
gaagctgacg tcctttccat ggctgctcgc ctgtgttgcc acctggattc tgcgcgggac    4380
gtccttctgc tacgtcccct cggccctcaa tccagcggac cttccttccc gcggcctgct    4440
gccggctctg cggcctcttc cgcgtcttcg ccttcgccct cagacgagtc ggatctccct    4500
ttgggccgcc tccccgcatc gggaattccc gcggttcgct ttaagaccaa tgacttacaa    4560
ggcagctgta gatcttagcc acttttttaaa agaaaagggg ggactggaag gctaattca    4620
ctcccaacga agacaagatc tgcttttttgc ttgtactggg tctctctggt tagaccagat    4680
ctgagcctgg gagctctctg gctaactagg gaacccactg cttaagcctc aataaagctt    4740
gccttgagtg cttcaagtag tgtgtgcccg tctgttgtgt gactctggta actagagatc    4800
cctcagaccc tttagtcag tgtggaaaat ctctagcagt agtagttcat gtcatcttat    4860
tattcagtat ttataacttg caaagaaatg aatatcagag agtgagagga acttgtttat    4920
tgcagcttat aatggttaca aataaagcaa tagcatcaca aatttcacaa ataaagcatt    4980
ttttttcactg cattctagtt gtggtttgtc caaactcatc aatgtatctt atcatgtctg    5040
gctctagcta tcccgcccct aactccgccc atcccgcccc taactccgcc cagttccgcc    5100
cattctccgc cccatggctg actaattttt tttatttatg cagaggccga ggccgcctcg    5160
gcctctgagc tattccagaa gtagtgagga ggcttttttg gaggcctagg gacgtaccca    5220
attcgccta tagtgagtcg tattacgcgc gctcactggc cgtcgtttta caacgtcgtg    5280
actgggaaaa ccctggcgtt acccaactta atcgccttgc agcacatccc cctttcgcca    5340
gctggcgtaa tagcgaagag gcccgcaccg atcgcccttc ccaacagttg cgcagcctga    5400
atggcgaatg ggacgcgccc tgtagcggcg cattaagcgc ggcgggtgtg tggttacgc    5460
gcagcgtgac cgctacactt gccagcgccc tagcgcccgc tcctttcgct ttcttccctt    5520
cctttctcgc cacgttcgcc ggctttcccc gtcaagctct aaatcggggg ctccctttag    5580
ggttccgatt tagtgcttta cggcacctcg accccaaaaa acttgattag ggtgatggtt    5640
cacgtagtgg gccatcgccc tgatagacgg ttttcgccc tttgacgttg gagtccacgt    5700
tctttaatag tggactcttg ttccaaactg gaacaacact caaccctatc tcggtctatt    5760
cttttgattt ataagggatt tgccgatttc ggcctattg gttaaaaaat gagctgattt    5820
aacaaaaatt taacgcgaat tttaacaaaa tattaacgct tacaatttag gtggcacttt    5880
tcggggaaat gtgcgcggaa cccctatttg tttatttttc taaatacatt caaatatgta    5940
tccgctcatg agacaataac cctgataaat gcttcaataa tattgaaaaa ggaagagtat    6000
gagtattcaa catttccgtg tcgcccttat tcccttttttt gcggcatttt gccttcctgt    6060
ttttgctcac ccagaaacgc tggtgaaagt aaaagatgct gaagatcagt tgggtgcacg    6120
agtgggttac atcgaactgg atctcaacag cggtaagatc cttgagagtt ttcgccccga    6180
agaacgtttt ccaatgatga gcactttaa agttctgcta tgtggcgcgg tattatcccg    6240
```

-continued

```
tattgacgcc gggcaagagc aactcggtcg ccgcatacac tattctcaga atgacttggt    6300
tgagtactca ccagtcacag aaaagcatct tacggatggc atgacagtaa gagaattatg    6360
cagtgctgcc ataaccatga gtgataacac tgcggccaac ttacttctga caacgatcgg    6420
aggaccgaag gagctaaccg cttttttgca caacatgggg gatcatgtaa ctcgccttga    6480
tcgttgggaa ccggagctga atgaagccat accaaacgac gagcgtgaca ccacgatgcc    6540
tgtagcaatg gcaacaacgt tgcgcaaact attaactggc gaactactta ctctagcttc    6600
ccggcaacaa ttaatagact ggatggaggc ggataaagtt gcaggaccac ttctgcgctc    6660
ggcccttccg gctggctggt ttattgctga taaatctgga gccggtgagc gtgggtctcg    6720
cggtatcatt gcagcactgg ggccagatgg taagccctcc cgtatcgtag ttatctacac    6780
gacggggagt caggcaacta tggatgaacg aaatagacag atcgctgaga taggtgcctc    6840
actgattaag cattggtaac tgtcagacca agtttactca tatatacttt agattgattt    6900
aaaacttcat ttttaattta aaaggatcta ggtgaagatc ctttttgata atctcatgac    6960
caaaatccct taacgtgagt tttcgttcca ctgagcgtca ccccgtag aaaagatcaa    7020 aggatcttct tgagatcctt ttttttctgcg cgtaatctgc tgcttgcaaa caaaaaaacc    7080
accgctacca gcggtggttt gtttgccgga tcaagagcta ccaactcttt ttccgaaggt    7140
aactggcttc agcagagcgc agataccaaa tactgttctt ctagtgtagc cgtagttagg    7200
ccaccacttc aagaactctg tagcaccgcc tacatacctc gctctgctaa tcctgttacc    7260
agtggctgct gccagtggcg ataagtcgtg tcttaccggg ttggactcaa gacgatagtt    7320
accggataag gcgcagcggt cgggctgaac ggggggttcg tgcacacagc ccagcttgga    7380
gcgaacgacc tacaccgaac tgagatacct acagcgtgag ctatgagaaa gcgccacgct    7440
tcccgaagag agaaaggcgg acaggtatcc ggtaagcggc agggtcggaa caggagagcg    7500
cacgagggag cttccagggg gaaacgcctg gtatctttat agtcctgtcg ggtttcgcca    7560
cctctgactt gagcgtcgat ttttgtgatg ctcgtcaggg gggcggagcc tatgaaaaa    7620 cgccagcaac gcggcctttt tacggttcct ggccttttgc tggccttttg ctcacatgtt    7680
ctttcctgcg ttatcccctg attctgtgga taaccgtatt accgcctttg agtgagctga    7740
taccgctcgc cgcagccgaa cgaccgagcg cagcgagtca gtgagcgagg aagcggaaga    7800
gcgcccaata cgcaaaccgc ctctccccgc gcgttggccg attcattaat gcagctggca    7860
cgacaggttt cccgactgga aagcgggcag tgagcgcaac gcaattaatg tgagttagct    7920
cactcattag gcaccccagg ctttacactt tatgcttccg gctcgtatgt tgtgtggaat    7980
tgtgagcgga taacaatttc acacaggaaa cagctatgac catgattacg ccaagcgcgc    8040 aattaacccct cactaaaggg aacaaaagct ggagctgcaa gctt    8084
```

<210> SEQ ID NO 16
<211> LENGTH: 7756
<212> TYPE: DNA
<213> ORGANISM: Artificial Sequence
<220> FEATURE:
<223> OTHER INFORMATION: Synthetic lentiviral vector

<400> SEQUENCE: 16

```
aatgtagtct tatgcaatac tcttgtagtc ttgcaacatg gtaacgatga gttagcaaca      60
tgccttacaa ggagagaaaa agcaccgtgc atgccgattg gtggaagtaa ggtggtacga     120
tcgtgcctta ttaggaaggc aacagacggg tctgacatgg attggacgaa ccactgaatt     180
gccgcattgc agagatattg tatttaagtg cctagctcga tacataaacg ggtctctctg     240
```

```
gttagaccag atctgagcct gggagctctc tggctaacta gggaacccac tgcttaagcc      300
tcaataaagc ttgccttgag tgcttcaagt agtgtgtgcc cgtctgttgt gtgactctgg      360
taactagaga tccctcagac ccttttagtc agtgtggaaa atctctagca gtggcgcccg      420
aacagggact tgaaagcgaa agggaaacca gaggagctct ctcgacgcag gactcggctt      480
gctgaagcgc gcacggcaag aggcgagggg cggcgactgg tgagtacgcc aaaaattttg      540
actagcggag gctagaagga gagagatggg tgcgagagcg tcagtattaa gcggggggaga      600 attagatcgc gatgggaaaa aattcggtta aggccagggg gaaagaaaaa atataaatta      660
aaacatatag tatgggcaag cagggagcta gaacgattcg cagttaatcc tggcctgtta      720
gaaacatcag aaggctgtag acaaatactg ggacagctac aaccatccct tcagacagga      780
tcagaagaac ttagatcatt atataataca gtagcaaccc tctattgtgt gcatcaaagg      840
atagagataa aagacaccaa ggaagcttta gacaagatag aggaagagca aaacaaaagt      900
aagaccaccg cacagcaagc ggccgctgat cttcagacct ggaggaggag atatgaggga      960
caattggaga agtgaattat ataaatataa agtagtaaaa attgaaccat taggagtagc     1020
acccaccaag gcaaagagaa gagtggtgca gagagaaaaa agagcagtgg gaataggagc     1080
tttgttcctt gggttcttgg gagcagcagg aagcactatg ggcgcagcgt caatgacgct     1140
gacggtacag gccagacaat tattgtctgg tatagtgcag cagcagaaca atttgctgag     1200
ggctattgag gcgcaacagc atctgttgca actcacagtc tggggcatca agcagctcca     1260
ggcaagaatc ctggctgtgg aaagatacct aaaggatcaa cagctcctgg ggatttgggg     1320
ttgctctgga aaactcattt gcaccactgc tgtgccttgg aatgctagtt ggagtaataa     1380
atctctggaa cagatttgga atcacacgac ctggatggag tgggacagag aaattaacaa     1440
ttacacaagc ttaatacact ccttaattga agaatcgcaa aaccagcaag aaaagaatga     1500
acaagaatta ttggaattag ataaatgggc aagtttgtgg aattggttta acataacaaa     1560
ttggctgtgg tatataaaat tattcataat gatagtagga ggcttggtag gtttaagaat     1620
agtttttgct gtactttcta tagtgaatag agttaggcag ggatattcac cattatcgtt     1680
tcagacccac ctcccaaccc cgaggggacc cgacaggccc gaaggaatag aagaagaagg     1740
tggagagaga gacagagaca gatccattcg attagtgaac ggatctcgac ggtatcgcta     1800
gcttttaaaa gaaaaggggg gattgggggg tacagtgcag gggaaagaat agtagacata     1860
atagcaacag acatacaaac taaagaatta caaaaacaaa ttacaaaaat tcaaaatttt     1920
actagtgatt atcggatcaa ctttgtatag aaaagttgtt ctaccgggta ggggaggcgc     1980
ttttcccaag gcagtctgga gcatgcgctt tagcagcccc gctgggcact ggcgctaca      2040 caagtggcct ctggcctcgc acacattcca catccaccgg taggcgccaa ccggctccgt     2100
tctttggtgg cccccttcgcg ccaccttcta ctcctcccct agtcaggaag ttccccccg      2160 ccccgcagct cgcgtcgtgc aggacgtgac aaatggaagt agcacgtctc actagtctcg     2220
tgcagatgga cagcaccgct gagcaatgga agcgggtagg cctttggggc agcggccaat     2280
agcagctttg ctccttcgct ttctgggctc agaggctggg aagggtggg tccggggcg       2340 ggctcagggg cgggctcagg ggcggggcgg gcgcccgaag gtcctccgga ggcccggcat     2400
tctgcacgct tcaaaagcgc acgtctgccg cgctgttctc ctcttcctca tctccgggcc     2460
tttcgacctc aagtttgtac aaaaaagcag gctgccacca tggaggggat cagtatatac     2520
acttcagata actacaccga ggaaatgggc tcaggggact atgactccat gaaggaaccc     2580
```

```
tgtttccgtg aagaaaatgc taatttcaat aaaatcttcc tgcccaccat ctactccatc    2640
atcttcttaa ctggcattgt gggcaatgga ttggtcatcc tggtcatggg ttaccagaag    2700
aaactgagaa gcatgacgga caagtacagg ctgcacctgt cagtggccga cctcctcttt    2760
gtcatcacgc ttcccttctg ggcagttgat gccgtggcaa actggtactt tgggaacttc    2820
ctatgcaagg cagtccatgt catctacaca gtcaacctct acagcagtgt cctcatcctg    2880
gccttcatca gtctggaccg ctacctggcc atcgtccacg ccaccaacag tcagaggcca    2940
aggaagctgt tggctgaaaa ggtggtctat gttggcgtct ggatccctgc cctcctgctg    3000
actattcccg acttcatctt tgccaacgtc agtgaggcag atgacagata tatctgtgac    3060
cgcttctacc ccaatgactt gtgggtggtt gtgttccagt ttcagcacat catggttggc    3120
cttatcctgc ctggtattgt catcctgtcc tgctattgca ttatcatctc caagctgtca    3180
cactccaagg gccaccagaa gcgcaaggcc ctcaagacca cagtcatcct catcctggct    3240
ttcttcgcct gttggctgcc ttactacatt gggatcagca tcgactcctt catcctcctg    3300
gaaatcatca agcaagggtg tgagtttgag aacactgtgc acaagtggat ttccatcacc    3360
gaggccctag ctttcttcca ctgttgtctg aaccccatcc tctatgcttt ccttggagcc    3420
aaatttaaaa cctctgccca gcacgcactc acctctgtga gcagagggtc cagcctcaag    3480
atcctctcca aggaaagcg aggtggacat tcatctgttt ccactgagtc tgagtcttca    3540
agttttcact ccagctaaac ccagctttct tgtacaaagt ggtgataatc gaattccgat    3600
aatcaacctc tggattacaa aatttgtgaa agattgactg gtattcttaa ctatgttgct    3660
ccttttacgc tatgtggata cgctgcttta atgcctttgt atcatgctat tgcttccgt     3720 atggctttca ttttctcctc cttgtataaa tcctggttgc tgtctcttta tgaggagttg    3780
tggcccgttg tcaggcaacg tggcgtggtg tgcactgtgt ttgctgacgc aaccccact     3840 ggttggggca ttgccaccac ctgtcagctc ctttccggga cttttcgcttt cccctccct    3900 attgccacgg cggaactcat cgccgcctgc cttgcccgct gctggacagg gctcggctg     3960 ttgggcactg acaattccgt ggtgttgtcg gggaagctga cgtcctttcc atggctgctc    4020
gcctgtgttg ccacctggat tctgcgcggg acgtccttct gctacgtccc ttcggccctc    4080
aatccagcgg accttccttc ccgcggcctg ctgccggctc tgcggcctct tccgcgtctt    4140
cgccttcgcc ctcagacgag tcggatctcc ctttgggccg cctccccgca tcgggaattc    4200
ccgcggttcg ctttaagacc aatgacttac aaggcagctg tagatcttag ccactttta    4260 aaagaaaagg ggggactgga agggctaatt cactcccaac gaagacaaga tctgcttttt    4320
gcttgtactg ggtctctctg gttagaccag atctgagcct gggagctctc tggctaacta    4380
gggaacccac tgcttaagcc tcaataaagc ttgccttgag tgcttcaagt agtgtgtgcc    4440
cgtctgttgt gtgactctgg taactagaga tccctcagac ccttttagtc agtgtggaaa    4500
atctctagca gtagtagttc atgtcatctt attattcagt atttataact gcaaagaaa     4560 tgaatatcag agagtgagag gaacttgttt attgcagctt ataatggtta caaataaagc    4620
aatagcatca caaatttcac aaataaagca ttttttttcac tgcattctag ttgtggtttg    4680
tccaaactca tcaatgtatc ttatcatgtc tggctctagc tatcccgccc ctaactccgc    4740
ccatcccgcc cctaactccg cccagttccg cccattctcc gccccatggc tgactaattt    4800 ttttttattta tgcagaggcc gaggccgcct cggcctctga gctattccag aagtagtgag    4860
gaggcttttt tggaggccta gggacgtacc caattcgccc tatagtgagt cgtattacgc    4920
gcgctcactg gccgtcgttt tacaacgtcg tgactgggaa aaccctggcg ttacccaact    4980
```

```
taatcgcctt gcagcacatc cccctttcgc cagctggcgt aatagcgaag aggcccgcac   5040
cgatcgccct tcccaacagt tgcgcagcct gaatggcgaa tgggacgcgc cctgtagcgg   5100
cgcattaagc gcggcgggtg tggtggttac gcgcagcgtg accgctacac ttgccagcgc   5160
cctagcgccc gctcctttcg ctttcttccc ttcctttctc gccacgttcg ccggctttcc   5220
ccgtcaagct ctaaatcggg ggctcccttt agggttccga tttagtgctt tacggcacct   5280
cgaccccaaa aaacttgatt agggtgatgg ttcacgtagt gggccatcgc cctgatagac   5340 ggttttttcgc cctttgacgt tggagtccac gttctttaat agtggactct tgttccaaac   5400
tggaacaaca ctcaacccta tctcggtcta ttcttttgat ttataaggga ttttgccgat   5460
ttcggcctat tggttaaaaa atgagctgat ttaacaaaaa tttaacgcga attttaacaa   5520
aatattaacg cttacaattt aggtggcact tttcggggaa atgtgcgcgg aacccctatt   5580
tgtttatttt tctaaataca ttcaaatatg tatccgctca tgagacaata accctgataa   5640
atgcttcaat aatattgaaa aaggaagagt atgagtattc aacatttccg tgtcgccctt   5700
attccctttt ttgcggcatt ttgccttcct gttttгctc acccagaaac gctggtgaaa   5760
gtaaaagatg ctgaagatca gttgggtgca cgagtgggtt acatcgaact ggatctcaac   5820
agcggtaaga tccttgagag ttttcgcccc gaagaacgtt ttccaatgat gagcactttt   5880
aaagttctgc tatgtggcgc ggtattatcc cgtattgacg ccgggcaaga gcaactcggt   5940
cgccgcatac actattctca gaatgacttg gttgagtact caccagtcac agaaaagcat   6000
cttacggatg gcatgacagt aagagaatta tgcagtgctg ccataaccat gagtgataac   6060
actgcggcca acttacttct gacaacgatc ggaggaccga aggagctaac cgcttttttg   6120
cacaacatgg gggatcatgt aactcgcctt gatcgttggg aaccggagct gaatgaagcc   6180
ataccaaacg acgagcgtga caccacgatg cctgtagcaa tggcaacaac gttgcgcaaa   6240
ctattaactg gcgaactact tactctagct tcccggcaac aattaataga ctggatggag   6300
gcggataaag ttgcaggacc acttctgcgc tcggcccttc cggctggctg gtttattgct   6360
gataaatctg gagccggtga gcgtgggtct cgcggtatca ttgcagcact ggggccagat   6420
ggtaagccct cccgtatcgt agttatctac acgacgggga gtcaggcaac tatggatgaa   6480
cgaaatagac agatcgctga gataggtgcc tcactgatta agcattggta actgtcagac   6540
caagtttact catatatact ttagattgat ttaaaacttc atttttaatt taaaaggatc   6600
taggtgaaga tcctttttga taatctcatg accaaaatcc cttaacgtga gttttcgttc   6660
cactgagcgt cagaccccgt agaaaagatc aaaggatctt cttgagatcc tttttttctg   6720
cgcgtaatct gctgcttgca acaaaaaaa ccaccgctac cagcggtggt ttgtttgccg   6780
gatcaagagc taccaactct ttttccgaag gtaactggct tcagcagagc gcagatacca   6840
aatactgttc ttctagtgta gccgtagtta ggccaccact tcaagaactc tgtagcaccg   6900
cctacatacc tcgctctgct aatcctgtta ccagtggctg ctgccagtgg cgataagtcg   6960
tgtcttaccg ggttggactc aagacgatag ttaccggata aggcgcagcg tcgggctga   7020 acgggggggtt cgtgcacaca gcccagcttg gagcgaacga cctacaccga actgagatac   7080
ctacagcgtg agctatgaga aagcgccacg cttcccgaag agaaaaggc ggacaggtat   7140 ccggtaagcg gcagggtcgg aacaggagag cgcacgaggg agcttccagg gggaaacgcc   7200
tggtatcttt atagtcctgt cgggtttcgc cacctctgac ttgagcgtcg attttttgtga   7260 tgctcgtcag gggggcggag cctatggaaa aacgccagca acgcggcctt tttacggttc   7320
```

```
ctggcctttt gctggccttt tgctcacatg ttctttcctg cgttatcccc tgattctgtg    7380
gataaccgta ttaccgcctt tgagtgagct gataccgctc gccgcagccg aacgaccgag    7440
cgcagcgagt cagtgagcga ggaagcggaa gagcgcccaa tacgcaaacc gcctctcccc    7500
gcgcgttggc cgattcatta atgcagctgg cacgacaggt ttcccgactg gaaagcgggc    7560
agtgagcgca acgcaattaa tgtgagttag ctcactcatt aggcacccca ggctttacac    7620
tttatgcttc cggctcgtat gttgtgtgga attgtgagcg gataacaatt tcacacagga    7680
aacagctatg accatgatta cgccaagcgc gcaattaacc ctcactaaag ggaacaaaag    7740
ctggagctgc aagctt                                                    7756

<210> SEQ ID NO 17
<211> LENGTH: 8767
<212> TYPE: DNA
<213> ORGANISM: Artificial Sequence
<220> FEATURE:
<223> OTHER INFORMATION: Synthetic lentiviral vector

<400> SEQUENCE: 17
aatgtagtct tatgcaatac tcttgtagtc ttgcaacatg gtaacgatga gttagcaaca      60
tgccttacaa ggagagaaaa agcaccgtgc atgccgattg gtggaagtaa ggtggtacga     120
tcgtgcctta ttaggaaggc aacagacggg tctgacatgg attggacgaa ccactgaatt     180
gccgcattgc agagatattg tatttaagtg cctagctcga tacataaacg ggtctctctg     240
gttagaccag atctgagcct gggagctctc tggctaacta gggaacccac tgcttaagcc     300
tcaataaagc ttgccttgag tgcttcaagt agtgtgtgcc cgtctgttgt gtgactctgg     360
taactagaga tccctcagac ccttttagtc agtgtggaaa atctctagca gtggcgcccg     420
aacagggact tgaaagcgaa agggaaacca gaggagctct ctcgacgcag gactcggctt     480
gctgaagcgc gcacggcaag aggcgagggg cggcgactgg tgagtacgcc aaaaattttg     540
actagcggag gctagaagga gagagatggg tgcgagagcg tcagtattaa gcgggggaga     600
attagatcgc gatgggaaaa aattcggtta aggccagggg gaagaaaaaa atataaatta     660
aaacatatag tatgggcaag cagggagcta gaacgattcg cagttaatcc tggcctgtta     720
gaaacatcag aaggctgtag acaaatactg ggacagctac aaccatccct tcagacagga     780
tcagaagaac ttagatcatt atataataca gtagcaaccc tctattgtgt gcatcaaagg     840
atagagataa aagacaccaa ggaagcttta gacaagatag aggaagagca aaacaaaagt     900
aagaccaccg cacagcaagc ggccgctgat cttcagacct ggaggaggag atatgaggga     960
caattggaga agtgaattat ataaatataa agtagtaaaa attgaaccat taggagtagc    1020
acccaccaag gcaaagagaa gagtggtgca gagagaaaaa agagcagtgg gaataggagc    1080
tttgttcctt gggttcttgg gagcagcagg aagcactatg ggcgcagcgt caatgacgct    1140
gacggtacag gccagacaat tattgtctgg tatagtgcag cagcagaaca atttgctgag    1200
ggctattgag gcgcaacagc atctgttgca actcacagtc tggggcatca agcagctcca    1260
ggcaagaatc ctggctgtgg aaagatacct aaaggatcaa cagctcctgg ggatttgggg    1320
ttgctctgga aaactcattt gcaccactgc tgtgccttgg aatgctagtt ggagtaataa    1380
atctctggaa cagatttgga atcacacgac ctggatggag tgggacagag aaattaacaa    1440
ttacacaagc ttaatacact ccttaattga agaatcgcaa aaccagcaag aaaagaatga    1500
acaagaatta ttggaattag ataaatgggc aagtttgtgg aattggttta acataacaaa    1560
ttggctgtgg tatataaaat tattcataat gatagtagga ggcttggtag gtttaagaat    1620
```

```
agtttttgct gtactttcta tagtgaatag agttaggcag ggatattcac cattatcgtt    1680
tcagacccac ctcccaaccc cgagggtacc cgacaggccc gaaggaatag aagaagaagg    1740
tggagagaga gacagagaca gatccattcg attagtgaac ggatctcgac ggtatcgcta    1800
gcttttaaaa gaaaaggggg gattgggggg tacagtgcag gggaagaat agtagacata    1860 atagcaacag acatacaaac taagaatta caaaaacaaa ttacaaaaat tcaaaatttt    1920
actagtgatt atcggatcaa ctttgtatag aaaagttgtt ctaccgggta ggggaggcgc    1980
ttttcccaag gcagtctgga gcatgcgctt tagcagcccc gctgggcact tggcgctaca    2040
caagtggcct ctggcctcgc acacattcca catccaccgg taggcgccaa ccggctccgt    2100
tctttggtgg cccttcgcg ccaccttcta ctcctcccct agtcaggaag ttccccccg    2160 ccccgcagct cgcgtcgtgc aggacgtgac aaatggaagt agcacgtctc actagtctcg    2220
tgcagatgga cagcaccgct gagcaatgga agcgggtagg cctttgggc agcggccaat    2280 agcagctttg ctccttcgct ttctgggctc agaggctggg aaggggtggg tccgggggcg    2340
ggctcagggg cgggctcagg ggcggggcgg gcgcccgaag gtcctccgga ggcccggcat    2400
tctgcacgct tcaaaagcgc acgtctgccg cgctgttctc ctcttcctca tctccgggcc    2460
tttcgacctc aagtttgtac aaaaaagcag gctgccacca tgccgcgggg ctggaccgcg    2520
ctttgcttgc tgagtttgct gccttctggg ttcatgagtc ttgacaacaa cggtactgct    2580
accccagagt tacctaccca gggaacattt tcaaatgttt ctacaaatgt atcctaccaa    2640
gaaactacaa cacctagtac ccttggaagt accagcctgc accctgtgtc tcaacatggc    2700
aatgaggcca caacaaacat cacagaaacg acagtcaaat tcacatctac ctctgtgata    2760
acctcagttt atggaaacac aaactcttct gtccagtcac agacctctgt aatcagcaca    2820
gtgttcacca ccccagccaa cgtttcaact ccagagacaa ccttgaagcc tagcctgtca    2880
cctggaaatg tttcagacct ttcaaccact agcactagcc ttgcaacatc tcccactaaa    2940
ccctatacat catcttctcc tatcctaagt gacatcaagg cagaaatcaa atgttcaggc    3000
atcagagaag tgaaattgac tcagggcatc tgcctggagc aaaataagac ctccagctgt    3060
gcggagttta agaaggacag gggagagggc ctggcccgag tgctgtgtgg ggaggagcag    3120
gctgatgctg atgctggggc ccaggtatgc tccctgctcc ttgcccagtc tgaggtgagg    3180
cctcagtgtc tactgctggt cttggccaac agaacgaaa tttccagcaa actccaactt    3240
atgaaaaagc accaatctga cctgaaaaag ctggggatcc tagatttcac tgagcaagat    3300
gttgcaagcc accagagcta ttcccaaaag accctgattg cactggtcac ctcgggagcc    3360
ctgctggctg tcttgggcat cactggctat ttcctgatga atcgccgcag ctggagcccc    3420
acaggagaaa ggctggaact agaaccagga agcgagagg gcaggggaag tcttctaaca    3480
tgcggggacg tggaggaaaa tcccggcccc atggagggga tcagtatata cacttcagat    3540
aactacaccg aggaaatggg ctcagggac tatgactcca tgaaggaacc ctgtttccgt    3600
gaagaaaatg ctaatttcaa taaaatcttc ctgcccacca tctactccat catcttctta    3660
actggcattg tgggcaatgg attggtcatc ctggtcatgg gttaccagaa gaaactgaga    3720
agcatgacgg acaagtacag gctgcacctg tcagtgccg acctcctctt tgtcatcacg    3780
cttcccttct gggcagttga tgccgtggca aactggtact ttgggaactt cctatgcaag    3840
gcagtccatg tcatctacac agtcaacctc tacagcagtg tcctcatcct ggccttcatc    3900
agtctggacc gctacctggc catcgtccac gccaccaaca gtcagaggcc aaggaagctg    3960
```

```
ttggctgaaa aggtggtcta tgttggcgtc tggatccctg ccctcctgct gactattccc    4020
gacttcatct ttgccaacgt cagtgaggca gatgacagat atatctgtga ccgcttctac    4080
cccaatgact tgtgggtggt tgtgttccag tttcagcaca tcatggttgg ccttatcctg    4140
cctggtattg tcatcctgtc ctgctattgc attatcatct ccaagctgtc acactccaag    4200
ggccaccaga agcgcaaggc cctcaagacc acagtcatcc tcatcctggc tttcttcgcc    4260
tgttggctgc cttactacat tgggatcagc atcgactcct tcatcctcct ggaaatcatc    4320
aagcaagggt gtgagtttga gaacactgtg cacaagtgga tttccatcac cgaggcccta    4380
gctttcttcc actgttgtct gaaccccatc ctctatgctt tccttggagc caaatttaaa    4440
acctctgccc agcacgcact cacctctgtg agcagagggt ccagcctcaa gatcctctcc    4500
aaaggaaagc gaggtggaca ttcatctgtt tccactgagt ctgagtcttc aagttttcac    4560
tccagctaaa cccagctttc ttgtacaaag tggtgataat cgaattccga taatcaacct    4620
ctggattaca aaatttgtga agattgact  ggtattctta actatgttgc tccttttacg    4680
ctatgtggat acgctgcttt aatgcctttg tatcatgcta ttgcttcccg tatggctttc    4740
attttctcct ccttgtataa atcctggttg ctgtctcttt atgaggagtt gtggcccgtt    4800
gtcaggcaac gtggcgtggt gtgcactgtg tttgctgacg caaccccac  tggttggggc    4860 attgccacca cctgtcagct cctttccggg actttcgctt tccccctccc tattgccacg    4920
gcggaactca tcgccgcctg ccttgcccgc tgctggacag gggctcggct gttgggcact    4980
gacaattccg tggtgttgtc ggggaagctg acgtcctttc catggctgct cgcctgtgtt    5040
gccacctgga ttctgcgcgg gacgtccttc tgctacgtcc cttcggccct caatccagcg    5100
gaccttcctt cccgcggcct gctgccggct ctgcggcctc ttccgcgtct tcgccttcgc    5160
cctcagacga gtcggatctc cctttgggcc gcctccccgc atcgggaatt cccgcggttc    5220
gctttaagac caatgactta caaggcagct gtagatctta gccactttt  aaaagaaaag    5280 gggggactgg aagggctaat tcactcccaa cgaagacaag atctgctttt tgcttgtact    5340
gggtctctct ggttagacca gatctgagcc tgggagctct ctggctaact agggaaccca    5400
ctgcttaagc ctcaataaag cttgccttga gtgcttcaag tagtgtgtgc ccgtctgttg    5460
tgtgactctg gtaactagag atccctcaga ccctttagt  cagtgtggaa aatctctagc    5520
agtagtagtt catgtcatct tattattcag tatttataac ttgcaaagaa atgaatatca    5580
gagagtgaga ggaacttgtt tattgcagct tataatggtt acaaataaag caatagcatc    5640
acaaatttca caaataaagc atttttttca ctgcattcta gttgtggttt gtccaaactc    5700
atcaatgtat cttatcatgt ctggctctag ctatcccgcc cctaactccg cccatcccgc    5760
ccctaactcc gcccagttcc gcccattctc cgccccatgg ctgactaatt ttttttattt    5820
atgcagaggc cgaggccgcc tcggcctctg agctattcca gaagtagtga ggaggctttt    5880
ttggaggcct agggacgtac ccaattcgcc ctatagtgag tcgtattacg cgcgctcact    5940
ggccgtcgtt ttacaacgtc gtgactggga aaccctggc  gttacccaac ttaatcgcct    6000
tgcagcacat ccccctttcg ccagctggcg taatagcgaa gaggcccgca ccgatcgccc    6060
ttcccaacag ttgcgcagcc tgaatggcga atgggacgcg ccctgtagcg gcgcattaag    6120
cgcggcgggt gtggtggtta cgcgcagcgt gaccgctaca cttgccagcg ccctagcgcc    6180
cgctcctttc gctttcttcc cttcctttct cgccacgttc gccggctttc ccgtcaagc     6240 tctaaatcgg gggctccctt tagggttccg atttagtgct ttacggcacc tcgaccccaa    6300
aaaacttgat tagggtgatg gttcacgtag tgggccatcg ccctgataga cggttttcg     6360
```

| | | | | |
|---|---|---|---|---|
| cccctttgacg | ttggagtcca | cgttctttaa | tagtggactc | ttgttccaaa ctggaacaac | 6420 |
| actcaaccct | atctcggtct | attcttttga | tttataaggg | attttgccga tttcggccta | 6480 |
| ttggttaaaa | aatgagctga | tttaacaaaa | atttaacgcg | aattttaaca aaatattaac | 6540 |
| gcttacaatt | taggtggcac | ttttcgggga | aatgtgcgcg | gaacccctat tgtttattt | 6600 |
| ttctaaatac | attcaaatat | gtatccgctc | atgagacaat | aaccctgata aatgcttcaa | 6660 |
| taatattgaa | aaaggaagag | tatgagtatt | caacatttcc | gtgtcgccct tattcccttt | 6720 |
| tttgcggcat | tttgccttcc | tgttttttgct | cacccagaaa | cgctggtgaa agtaaaagat | 6780 |
| gctgaagatc | agttgggtgc | acgagtgggt | tacatcgaac | tggatctcaa cagcggtaag | 6840 |
| atccttgaga | gttttcgccc | cgaagaacgt | tttccaatga | tgagcacttt taaagttctg | 6900 |
| ctatgtggcg | cggtattatc | ccgtattgac | gccgggcaag | agcaactcgg tcgccgcata | 6960 |
| cactattctc | agaatgactt | ggttgagtac | tcaccagtca | cagaaaagca tcttacggat | 7020 |
| ggcatgacag | taagagaatt | atgcagtgct | gccataacca | tgagtgataa cactgcggcc | 7080 |
| aacttacttc | tgacaacgat | cggaggaccg | aaggagctaa | ccgcttttt gcacaacatg | 7140 |
| ggggatcatg | taactcgcct | tgatcgttgg | gaaccggagc | tgaatgaagc cataccaaac | 7200 |
| gacgagcgtg | acaccacgat | gcctgtagca | atggcaacaa | cgttgcgcaa actattaact | 7260 |
| ggcgaactac | ttactctagc | ttcccggcaa | caattaatag | actggatgga ggcggataaa | 7320 |
| gttgcaggac | cacttctgcg | ctcggccctt | ccggctggct | ggtttattgc tgataaatct | 7380 |
| ggagccggtg | agcgtgggtc | tcgcggtatc | attgcagcac | tggggccaga tggtaagccc | 7440 |
| tcccgtatcg | tagttatcta | cacgacgggg | agtcaggcaa | ctatggatga acgaaataga | 7500 |
| cagatcgctg | agataggtgc | ctcactgatt | aagcattggt | aactgtcaga ccaagtttac | 7560 |
| tcatatatac | tttagattga | tttaaaactt | catttttaat | ttaaaaggat ctaggtgaag | 7620 |
| atcctttttg | ataatctcat | gaccaaaatc | ccttaacgtg | agttttcgtt ccactgagcg | 7680 |
| tcagaccccg | tagaaaagat | caaaggatct | tcttgagatc | cttttttct gcgcgtaatc | 7740 |
| tgctgcttgc | aaacaaaaaa | accaccgcta | ccagcggtgg | tttgtttgcc ggatcaagag | 7800 |
| ctaccaactc | tttttccgaa | ggtaactggc | ttcagcagag | cgcagatacc aaatactgtt | 7860 |
| cttctagtgt | agccgtagtt | aggccaccac | ttcaagaact | ctgtagcacc gcctacatac | 7920 |
| ctcgctctgc | taatcctgtt | accagtggct | gctgccagtg | gcgataagtc gtgtcttacc | 7980 |
| gggttggact | caagacgata | gttaccggat | aaggcgcagc | ggtcgggctg aacggggggt | 8040 |
| tcgtgcacac | agcccagctt | ggagcgaacg | acctacaccg | aactgagata cctacagcgt | 8100 |
| gagctatgag | aaagcgccac | gcttcccgaa | gagagaaagg | cggacaggta tccggtaagc | 8160 |
| ggcagggtcg | gaacaggaga | gcgcacgagg | gagcttccag | ggggaaacgc ctggtatctt | 8220 |
| tatagtcctg | tcgggtttcg | ccacctctga | cttgagcgtc | gatttttgtg atgctcgtca | 8280 |
| ggggggcgga | gcctatggaa | aaacgccagc | aacgcggcct | ttttacggtt cctggccttt | 8340 |
| tgctggcctt | ttgctcacat | gttctttcct | gcgttatccc | ctgattctgt ggataaccgt | 8400 |
| attaccgcct | ttgagtgagc | tgataccgct | cgccgcagcc | gaacgaccga gcgcagcgag | 8460 |
| tcagtgagcg | aggaagcgga | agagcgccca | atacgcaaac | cgcctctccc cgcgcgttgg | 8520 |
| ccgattcatt | aatgcagctg | gcacgacagg | tttcccgact | ggaaagcggg cagtgagcgc | 8580 |
| aacgcaatta | atgtgagtta | gctcactcat | taggcacccc | aggctttaca ctttatgctt | 8640 |

```
ccggctcgta tgttgtgtgg aattgtgagc ggataacaat ttcacacagg aaacagctat    8700
gaccatgatt acgccaagcg cgcaattaac cctcactaaa gggaacaaaa gctggagctg    8760
caagctt                                                              8767
```

METHODS OF PRODUCING MODIFIED NATURAL KILLER CELLS AND METHODS OF USE

CROSS REFERENCE TO RELATED APPLICATIONS

This application is a continuation-in-part of International Application No. PCT/US2017/043774, filed Jul. 25, 2017, which claims the benefit of U.S. Provisional Application No. 62/366,493, filed Jul. 25, 2016, both of which are herein incorporated by reference in their entirety.

FIELD

This disclosure relates to methods of producing modified natural killer cells, compositions comprising the modified natural killer cells, and methods of their use.

BACKGROUND

Besides antigen-specific cytotoxic T lymphocytes, cellular components of the innate immune system can contribute to immune surveillance of malignant cell growth. In particular, natural killer (NK) cells can eliminate abnormal cells without priming or sensitization. Their activity is determined by the balance of signals from inhibitory and activating NK cell receptors. Inhibitory receptors, such as killer immunoglobulin receptors (KIRs), interact with self major histocompatibility complex (MHC) class I antigens and protect normal cells from NK cell attack.

Efforts at harnessing the anti-tumor activity of NK cells have been investigated for the immunotherapy of human cancer for over two decades. However, many malignant cells express MHC class I antigens and are thus naturally resistant to lysis by autologous NK cells. Accordingly, the first clinical trials using adoptive transfer of autologous NK cells have failed to produce significant therapeutic effects. Modulation of NK cell cytokine, chemokine, and activation/inhibitory receptor expression is an attractive strategy to bolster NK cell anti-tumor activity. However, efficient genetic modification of primary NK cells has been difficult to achieve.

SUMMARY

There is a need for simple and efficient gene transfer methods to effectively deliver and express genes of interest in primary NK cells. Disclosed herein are efficient viral vector-based methods for gene transfer into NK cells that demonstrate stable and robust long-term expression of transgenes.

Disclosed herein are method of producing NK cells that include or express one or more heterologous nucleic acids (referred to herein in some examples as "modified" NK cells). The methods include culturing a population of isolated NK cells (such as NK cells isolated or purified from a subject) in the presence of one or more cytokines (for example, interleukin (IL)-2, IL-15, and/or IL-21) to produce a population of activated NK cells. The population of activated NK cells are transduced with a viral vector including the one or more heterologous nucleic acids, for example by contacting the activated NK cells with viral particles including the viral vector. The resulting transduced NK cells are then cultured in the presence of one or more cytokines (for example, IL-2), and optionally in the presence of feeder cells, to produce a population of expanded transduced NK cells.

Also disclosed herein are methods of treating a subject with a disorder (such as a tumor or hyperproliferative disorder or a viral infection) with the modified NK cells. In some embodiments, the methods include obtaining a population of isolated NK cells from the subject or from a donor and culturing the population of isolated NK cells in the presence of one or more cytokines (for example, IL-2, IL-15, and/or IL-21) to produce a population of activated NK cells. The population of activated NK cells are transduced with a viral vector including one or more heterologous nucleic acids suitable for treating the subject's disorder, for example by contacting the activated NK cells with viral particles including the viral vector. The resulting transduced NK cells are then cultured in the presence of one or more cytokines (for example, IL-2), and optionally in the presence of feeder cells, to produce a population of expanded transduced NK cells, which are administered to the subject (for example, in a composition including a pharmaceutically acceptable carrier).

Also disclosed herein are modified NK cells (such as a population of modified NK cells) including one or more heterologous nucleic acids, such as NK cells transduced with a viral vector (such as a lentiviral vector) that includes one or more nucleic acids of interest. In some examples, the heterologous nucleic acid encodes CXCR4, CCR7, CXCR3, or CD16 (for example, high affinity CD16 or CD16-V158). Additional nucleic acids of interest are shown in Table 1, below. Also disclosed are compositions that include modified NK cells (such as a population of modified NK cells) and a pharmaceutically acceptable carrier. In some embodiments, the modified NK cells are produced by the methods disclosed herein.

The foregoing and other features of the disclosure will become more apparent from the following detailed description, which proceeds with reference to the accompanying figures.

BRIEF DESCRIPTION OF THE DRAWINGS

FIGS. 1A and 1B are schematic diagrams illustrating an exemplary three plasmid lentiviral vector system that can be utilized in the disclosed methods (FIG. 1A) and an exemplary method for producing non-replicating lentivirus that can be used to transduce target cells (FIG. 1B).

post-transduction in NK cells primed with 500 IU/ml IL-2 for three days prior to transduction.

Figure 6:
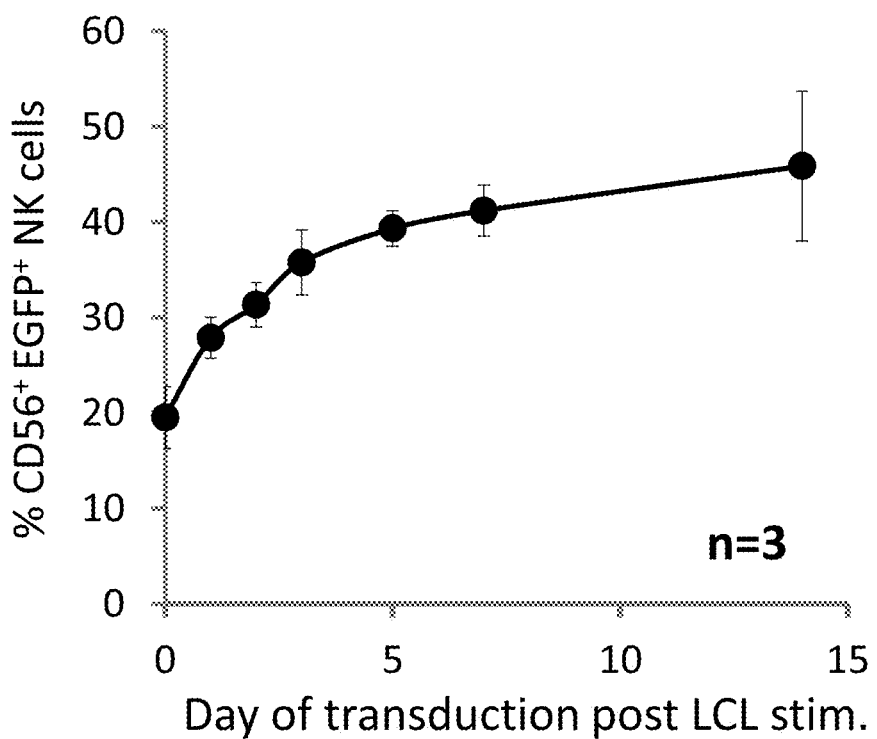

FIG. 6 is a graph showing transduction efficiency in CD56+ NK cells cultured on irradiated LCLs in media containing 500 IU/ml IL-2 for the indicated number of days prior to transduction. Two days after transduction, viral particles were removed and the cells were maintained in media containing 500 IU/ml IL-2. eGFP expression was analyzed by FACs seven days post-transduction.

Figure 7:
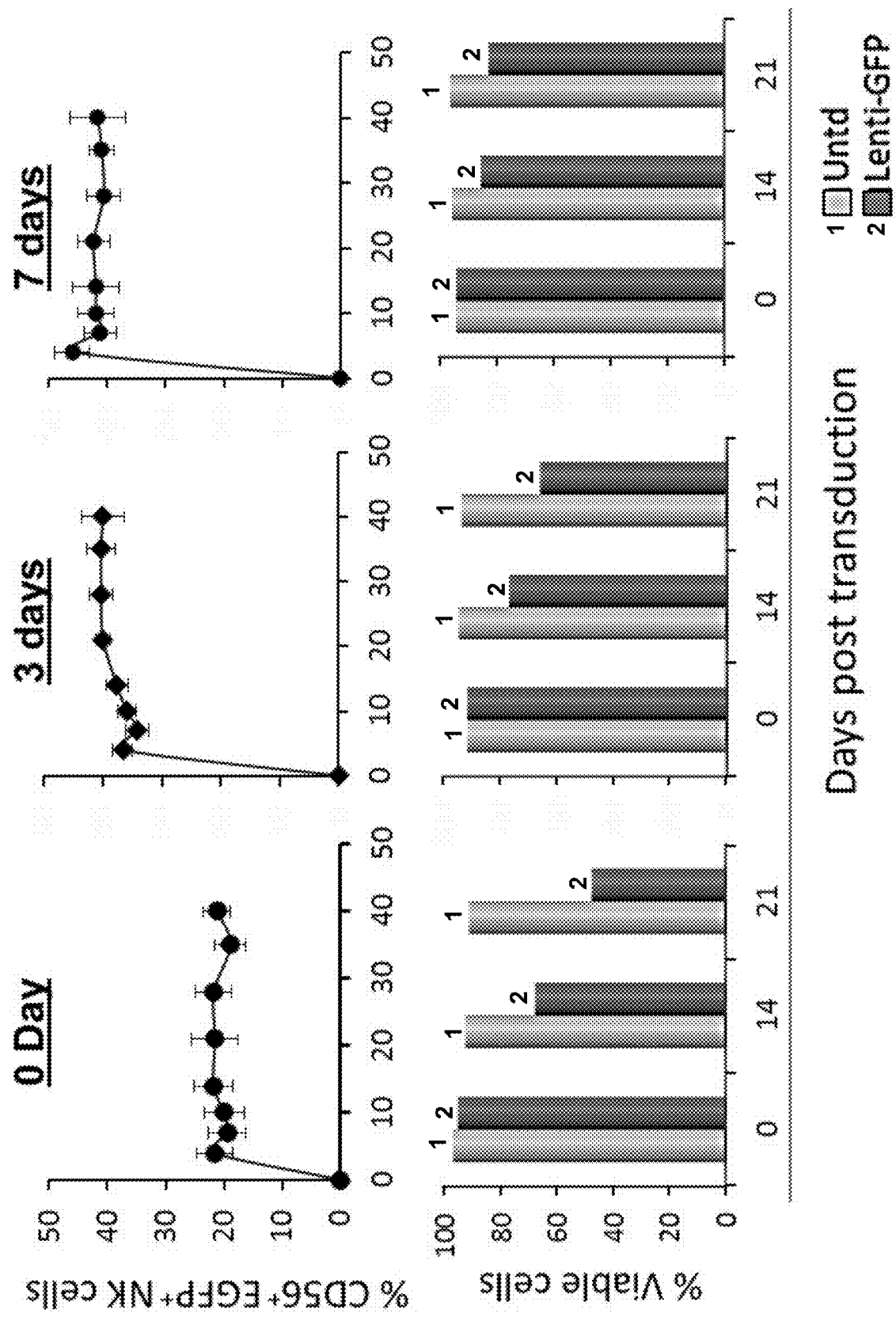

FIG. 7 is a series of graphs showing persistence of eGFP expression in transduced NK cells (top) and cell viability (bottom) at the indicated number of days post-transduction. Cells were cultured in medium containing 500 IU/ml IL-2 and irradiated feeder cells for 0, 3, or 7 days prior to transduction. eGFP expression was analyzed by FACS and cell viability was determined by trypan blue.

Figure 8A:
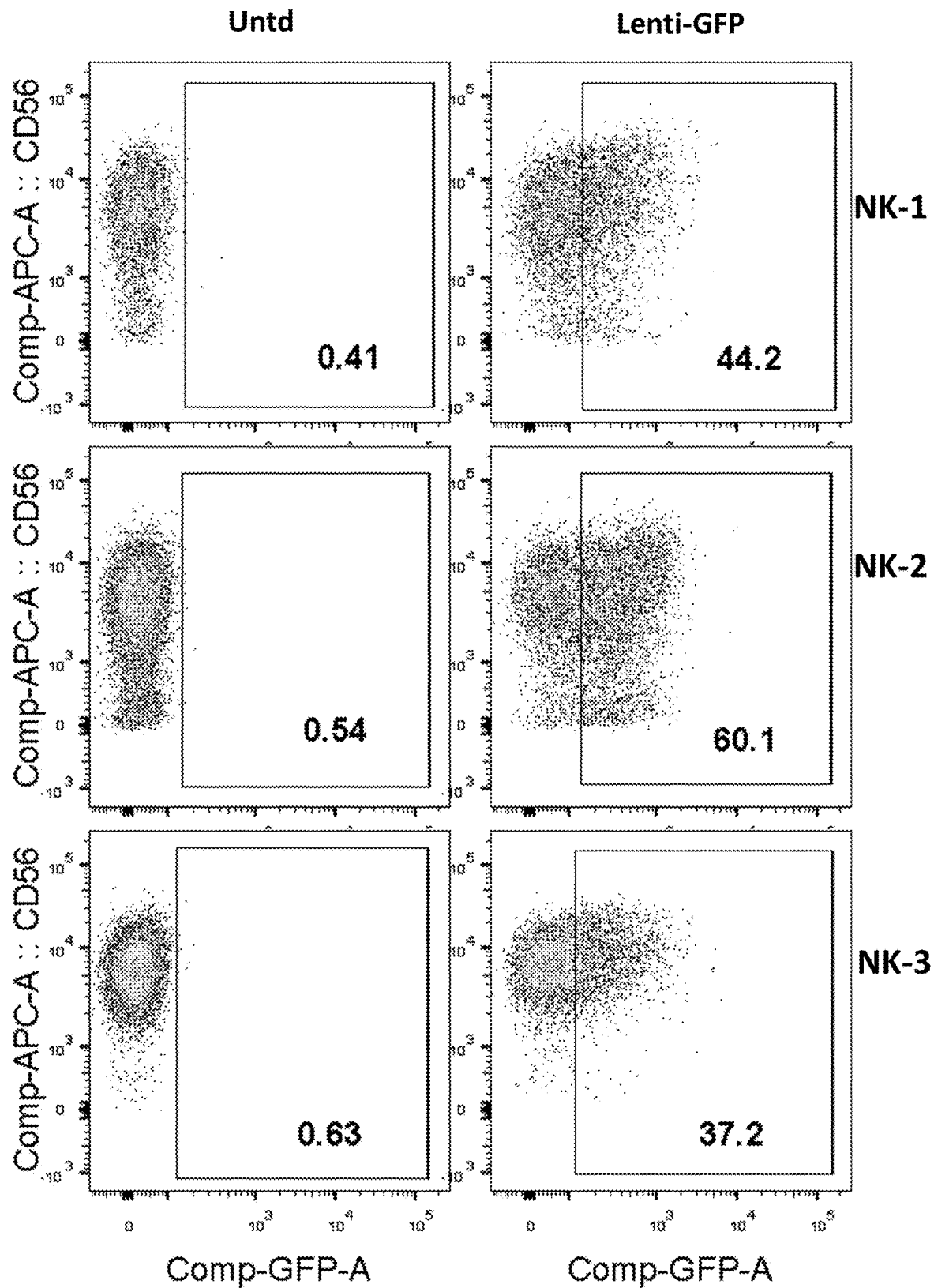
Figure 8B:
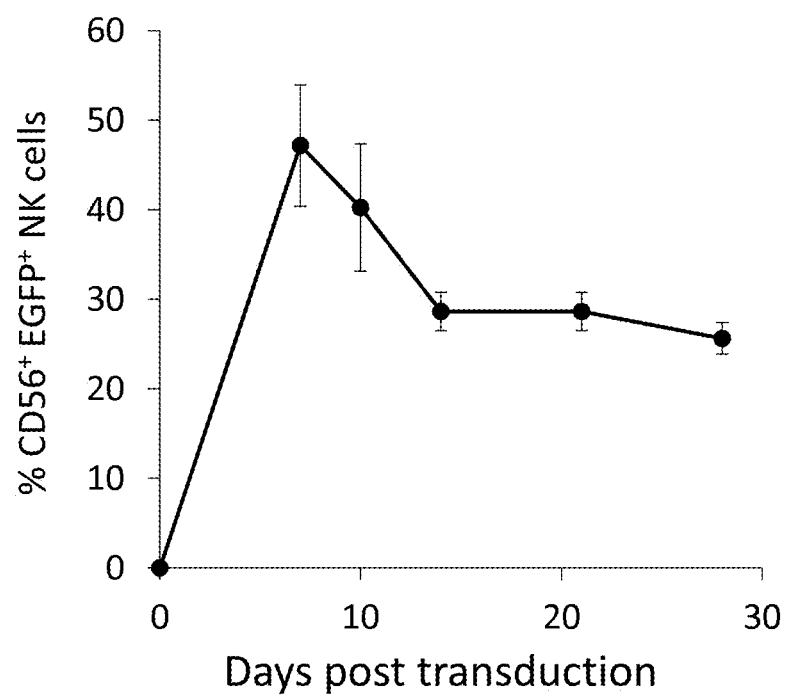

FIGS. 8A and 8B are a series of panels showing transduction efficiency of primary peripheral blood NK cells from three subjects (NK-1, NK-2, NK-3), expanded with irradiated LCL and 500 IU/ml IL-2 for 14 days prior to transduction. FIG. 8A shows FACS analysis of each cell line seven days post-transduction. FIG. 8B is a graph quantitating percent of CD56+ eGFP+NK cells on the indicated number of days post-transduction.

Figure 9:
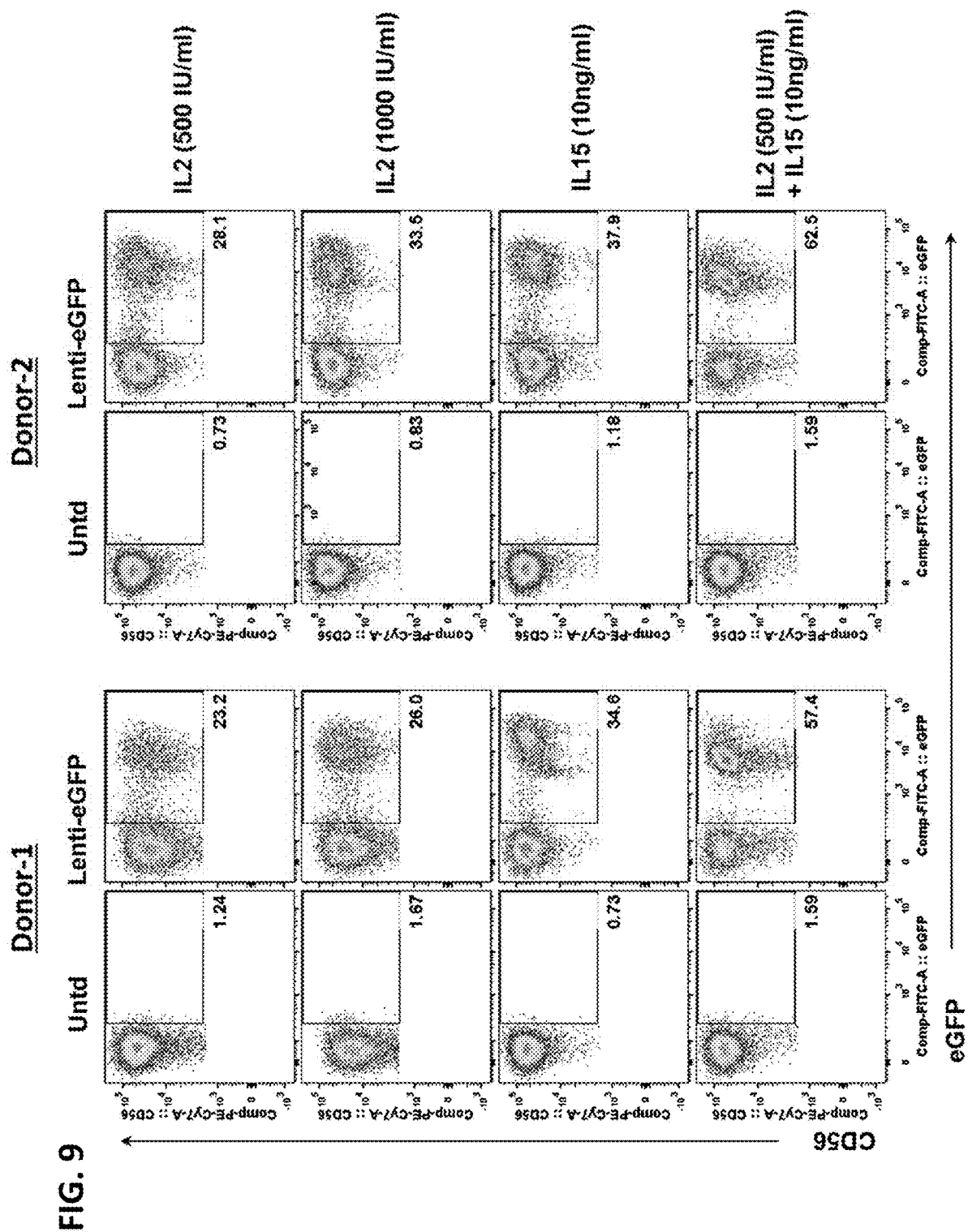

FIG. 9 is a series of panels showing eGFP expression in NK cells primed with 500 IU/ml IL-2 (top row), 1000 IU/ml IL-2 (second row), 10 ng/ml IL-15 (third row), or 500 IU/ml IL-2 plus 10 ng/ml IL-15 (bottom row) for three days prior to transduction. Two days post-transduction, viral particles were removed and cells were maintained on irradiated LCLs (10:1 LCL:NK) with 500 IU/ml IL-2. eGFP expression was analyzed by FACS two weeks post-transduction.

Figure 10:
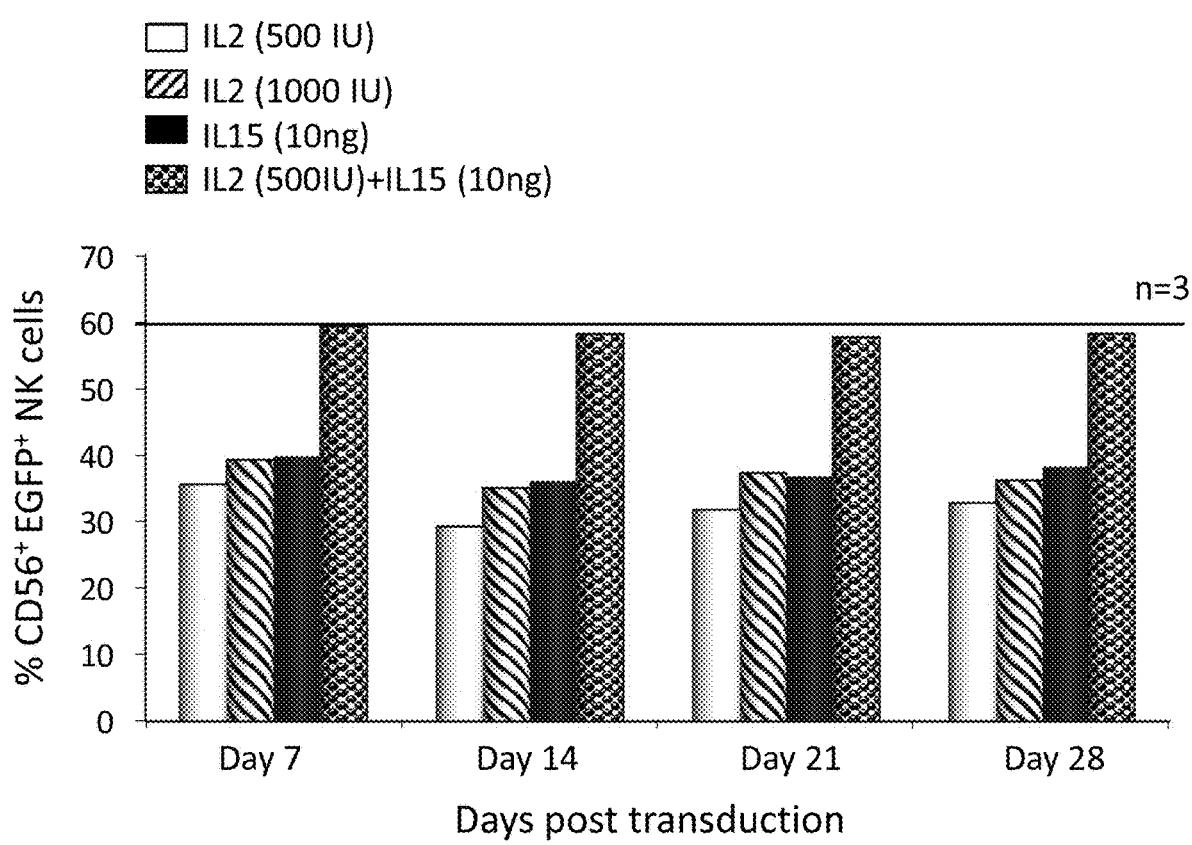

FIG. 10 is a graph showing persistence of transgene expression at the indicated number of days post-transduction with the indicated treatment for three days prior to transduction.

Figure 11:
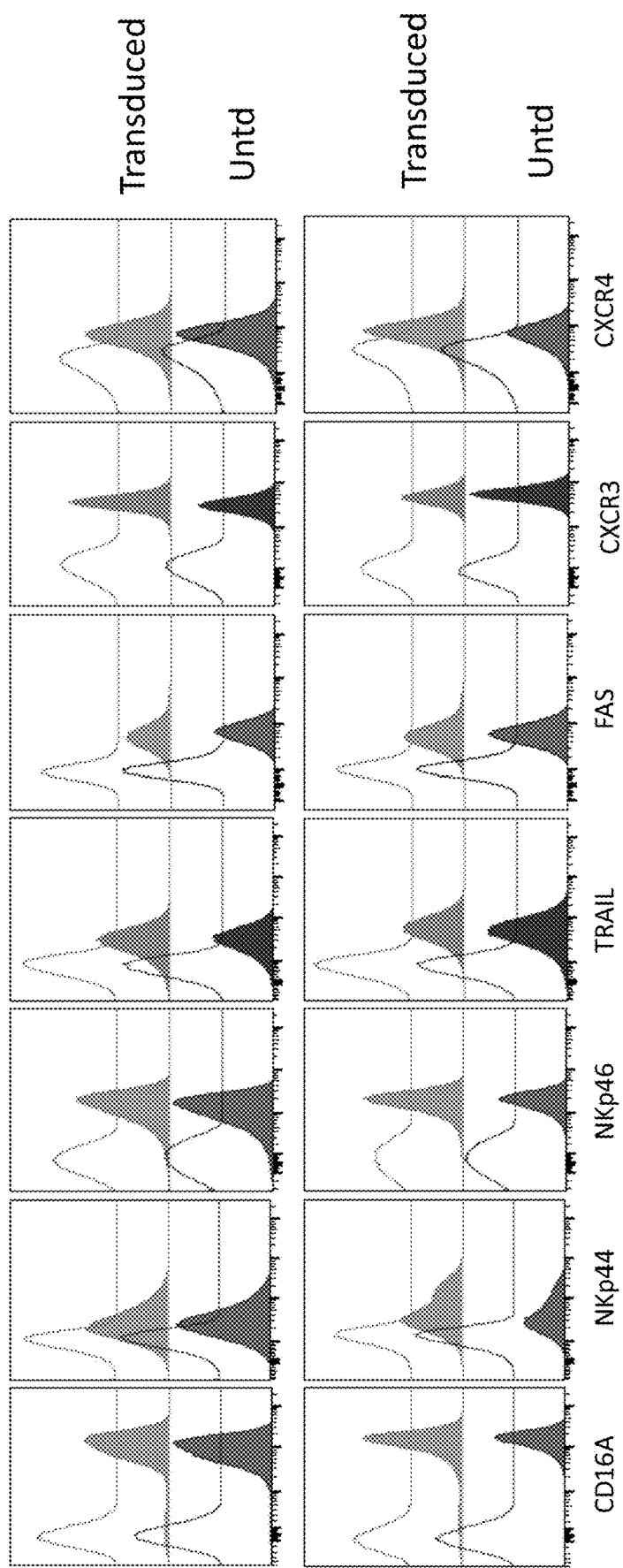

FIG. 11 is a series of panels showing expression of the indicated receptors on NK cells primed with 500 IU/ml IL (top) or 500 IU/ml IL-2 plus 10 ng/ml IL-15 (bottom) for three days prior to transduction. Two days post-transduction, viral particles were removed and irradiated LCLs (10:1 LCL:NK cells) were added and cells were maintained in media with 500 IU/ml IL-2. Analysis was by FACS at two weeks post-transduction. Open traces, IsoAb, filled traces, Ag-specific Ab.

Figure 12:
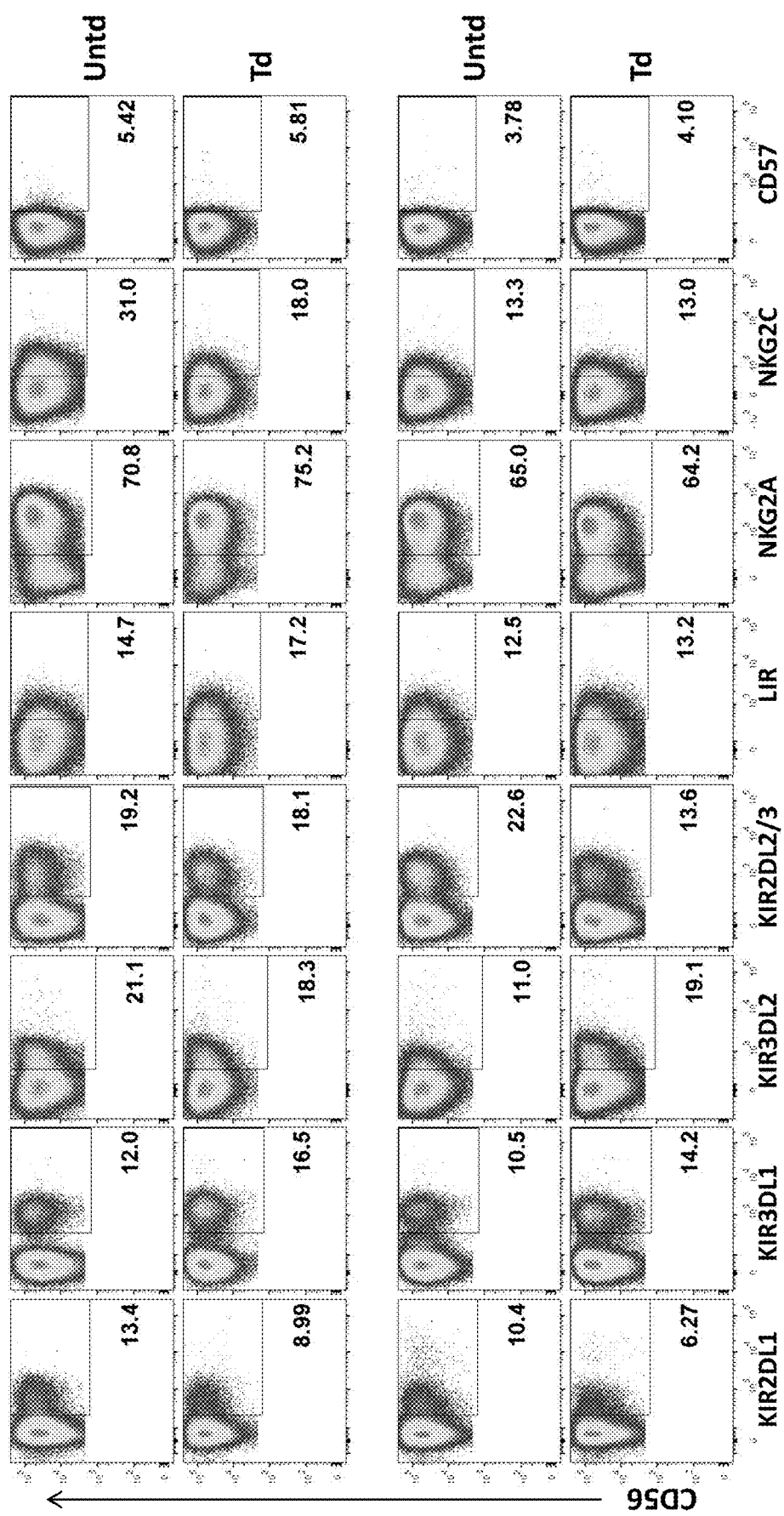

FIG. 12 is a series of panels showing expression of the indicated receptors on NK cells primed with 500 IU/ml IL (top) or 500 IU/ml IL-2 plus 10 ng/ml IL-15 (bottom) for three days prior to transduction. Two days post-transduction, viral particles were removed and irradiated LCLs (10:1 LCL:NK cells) were added and cells were maintained in media with 500 IU/ml IL-2. Analysis was by FACS at two weeks post-transduction.

Figure 13:
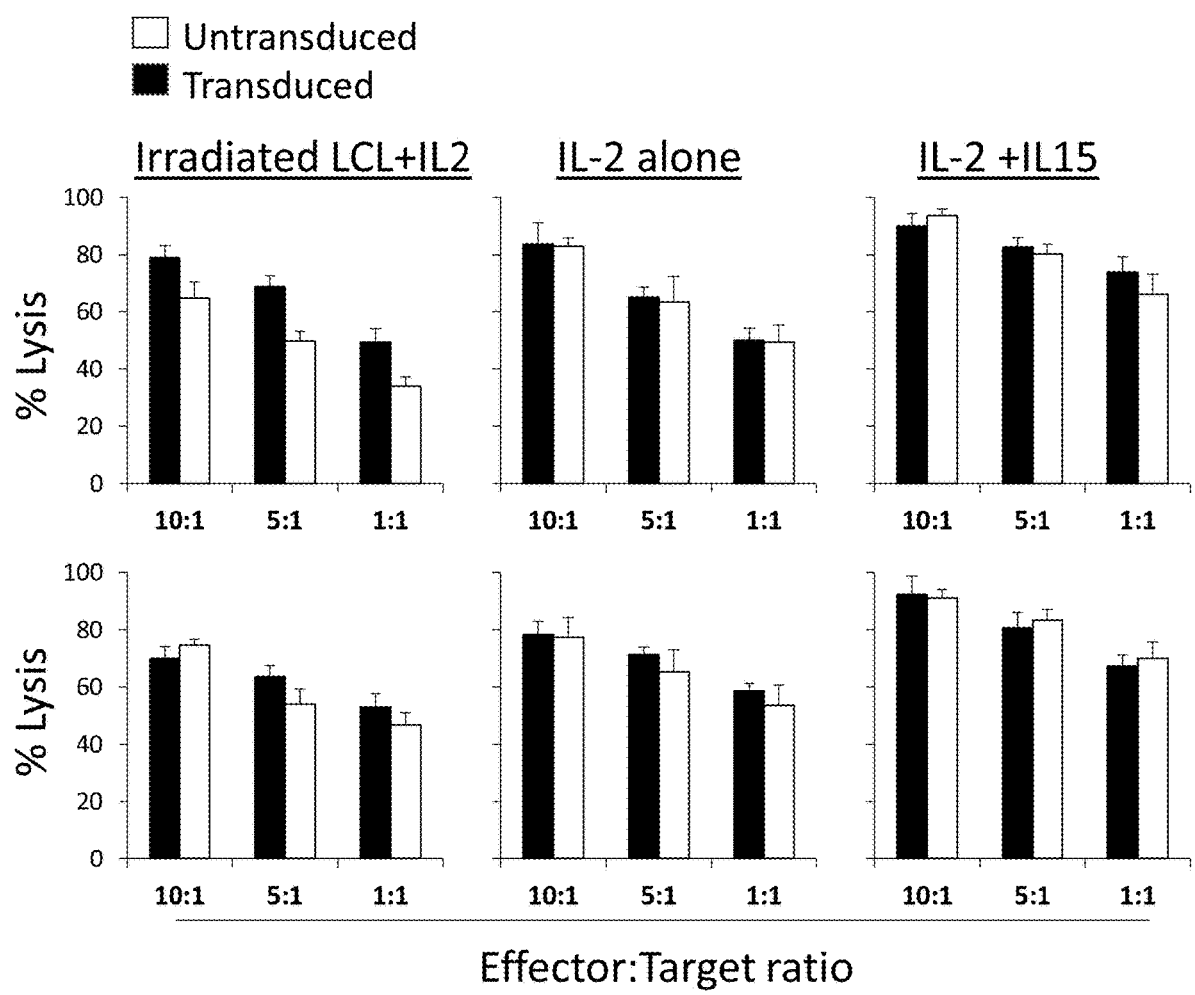

FIG. 13 is a series of graphs showing tumor cell lysis of K562 cells (top) or MOLM14 cells (bottom) in NK cells primed with the indicated conditions for three days prior to transduction. Cells were expanded with irradiated LCLs for 14 days prior to testing their tumor killing capacity by $^{51}$Cr release assay.

Figure 14:
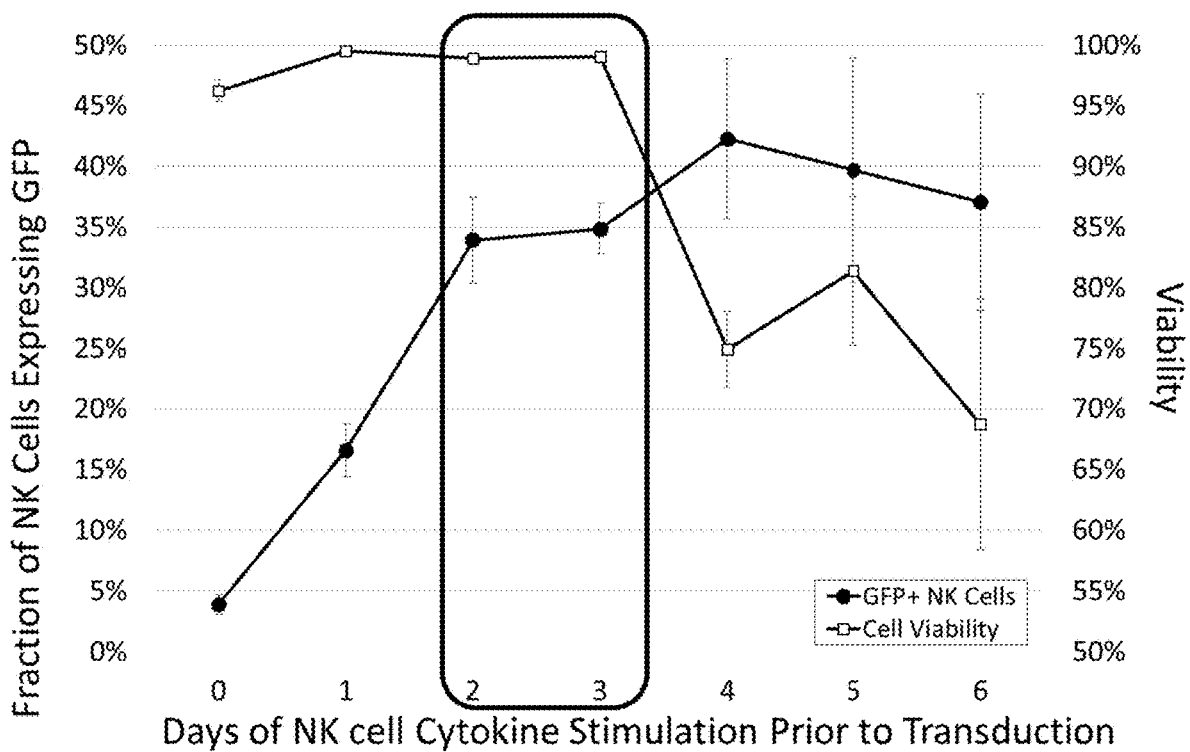

FIG. 14 is a graph showing fraction of NK cells expressing GFP (circles) and cell viability (squares) versus the number of days of cytokine stimulation (500 IU/ml IL-2) prior to transduction. A balance of transgene expression and viability was achieved with 2-3 days of cytokine stimulation prior to transduction (boxed area).

Figure 15:
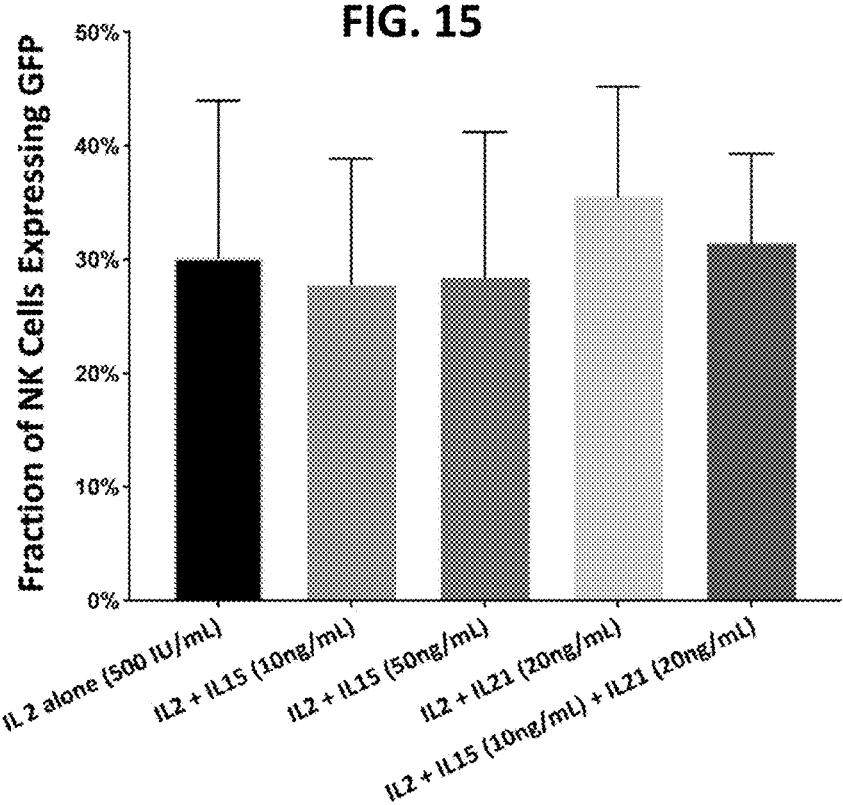

FIG. 15 is a graph showing the fraction of NK cells expressing GFP in NK cells treated with the indicated cytokines prior to transduction. There was no significant difference between IL-2 alone and combinations of IL-2 with IL-15 and/or IL-21.

Figure 16A:
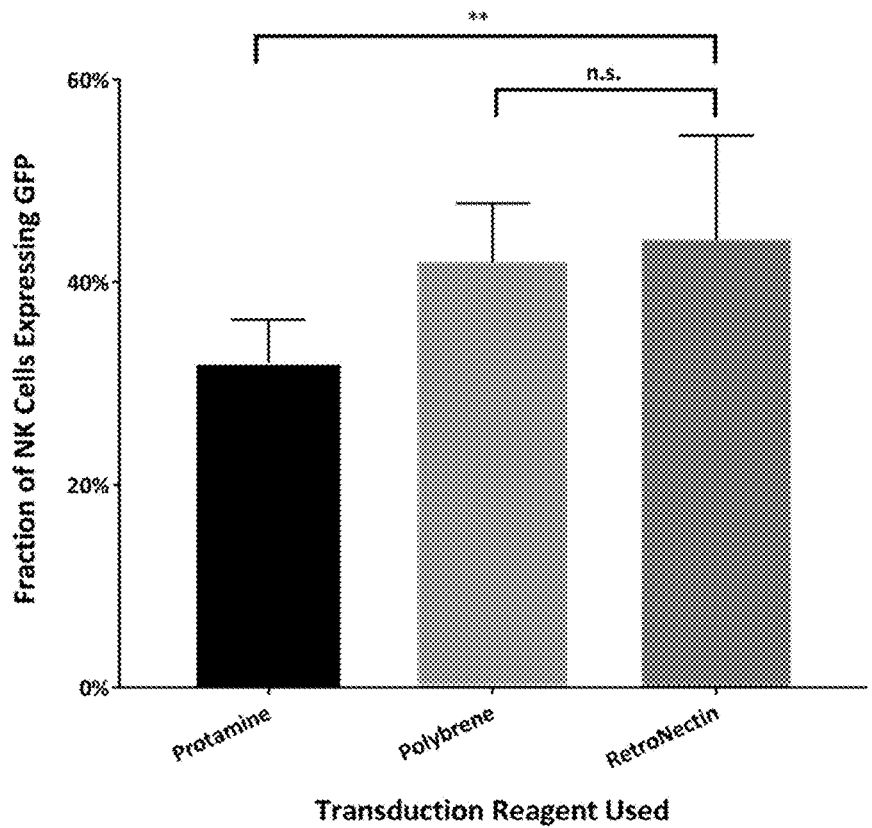
Figure 16B:
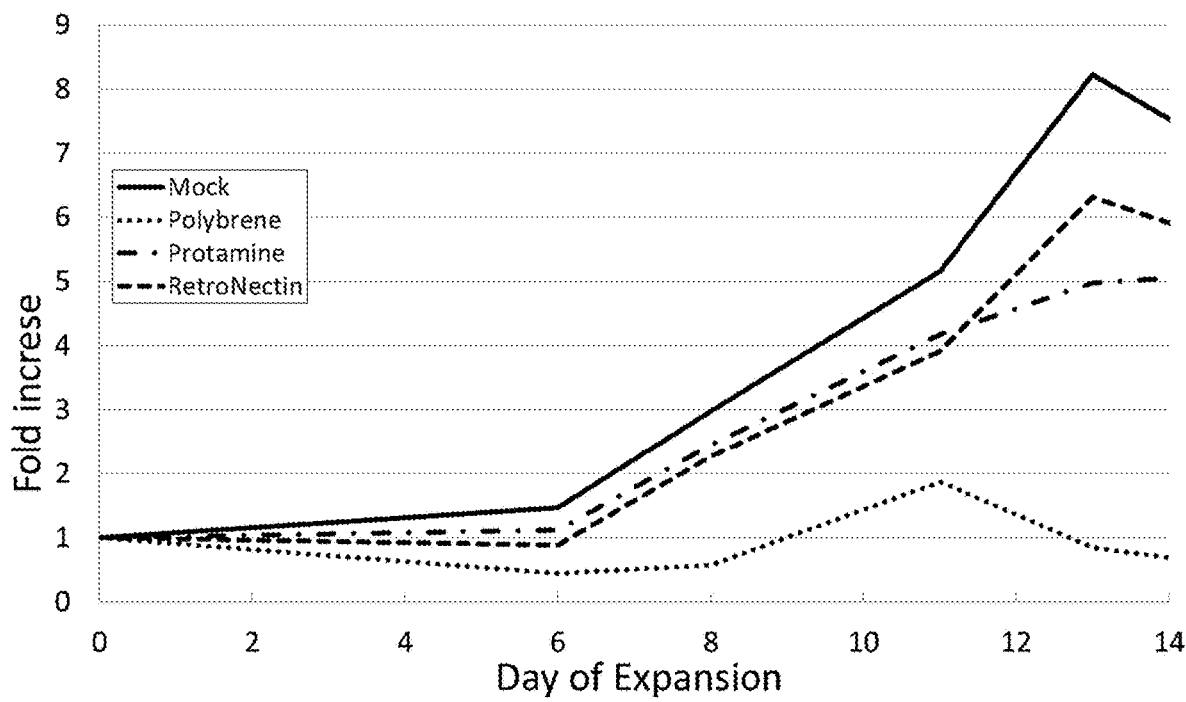

FIGS. 16A and 16B are graphs showing the effect of transduction reagents on transduction efficiency (FIG. 16A) and NK cell expansion (FIG. 16B).

Figure 17:
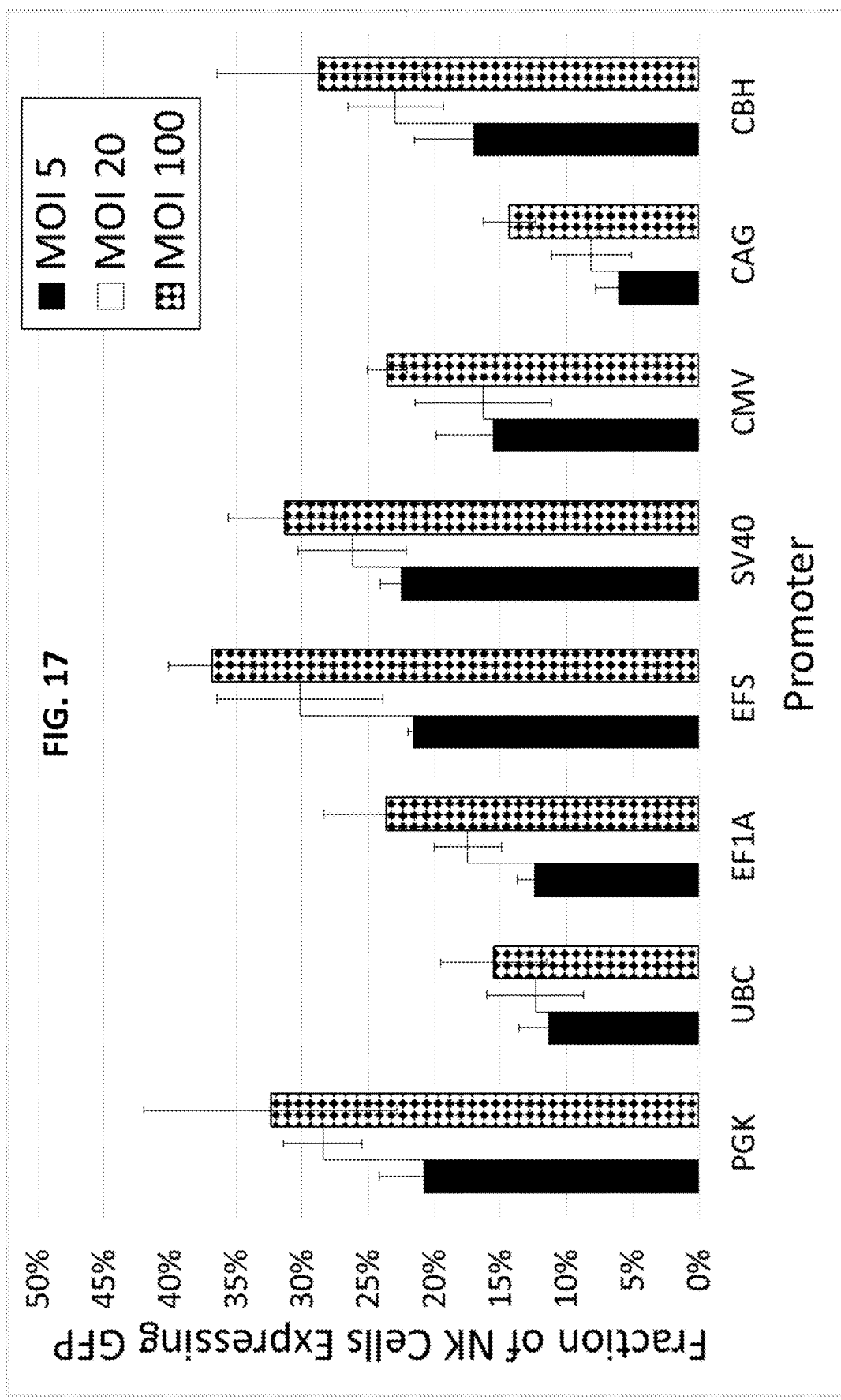

FIG. 17 is a graph showing transduction efficiency of NK cells transduced with GFP under the control of the indicated promoters at MOI of 5, 20, or 100.

Figure 18:
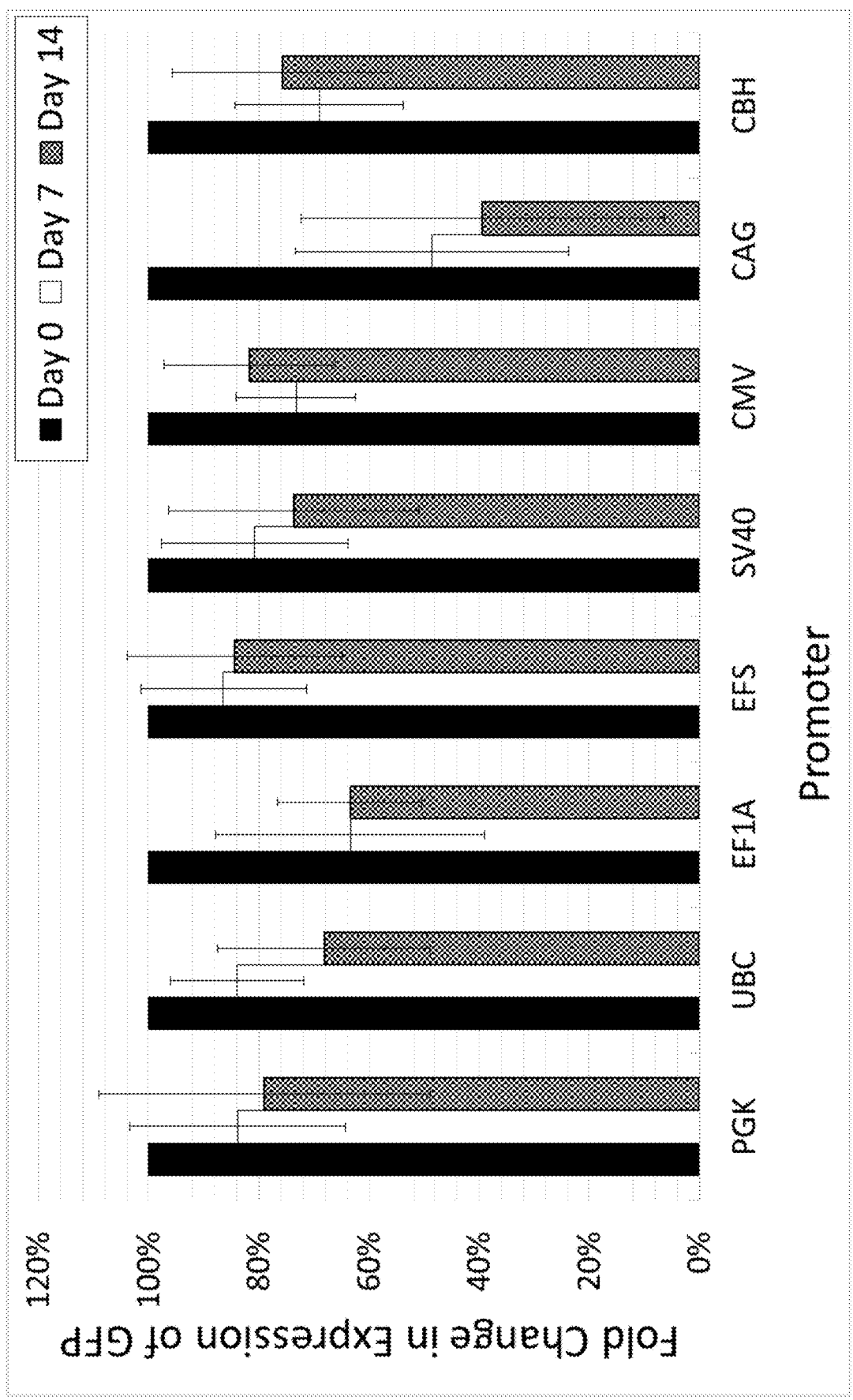

FIG. 18 is a graph showing the fold-change in expression of GFP in NK cells transduced with GFP under the control of the indicated promoters on days 7 and 14 post-transduction, compared to expression on day 0 (100%).

Figure 19:
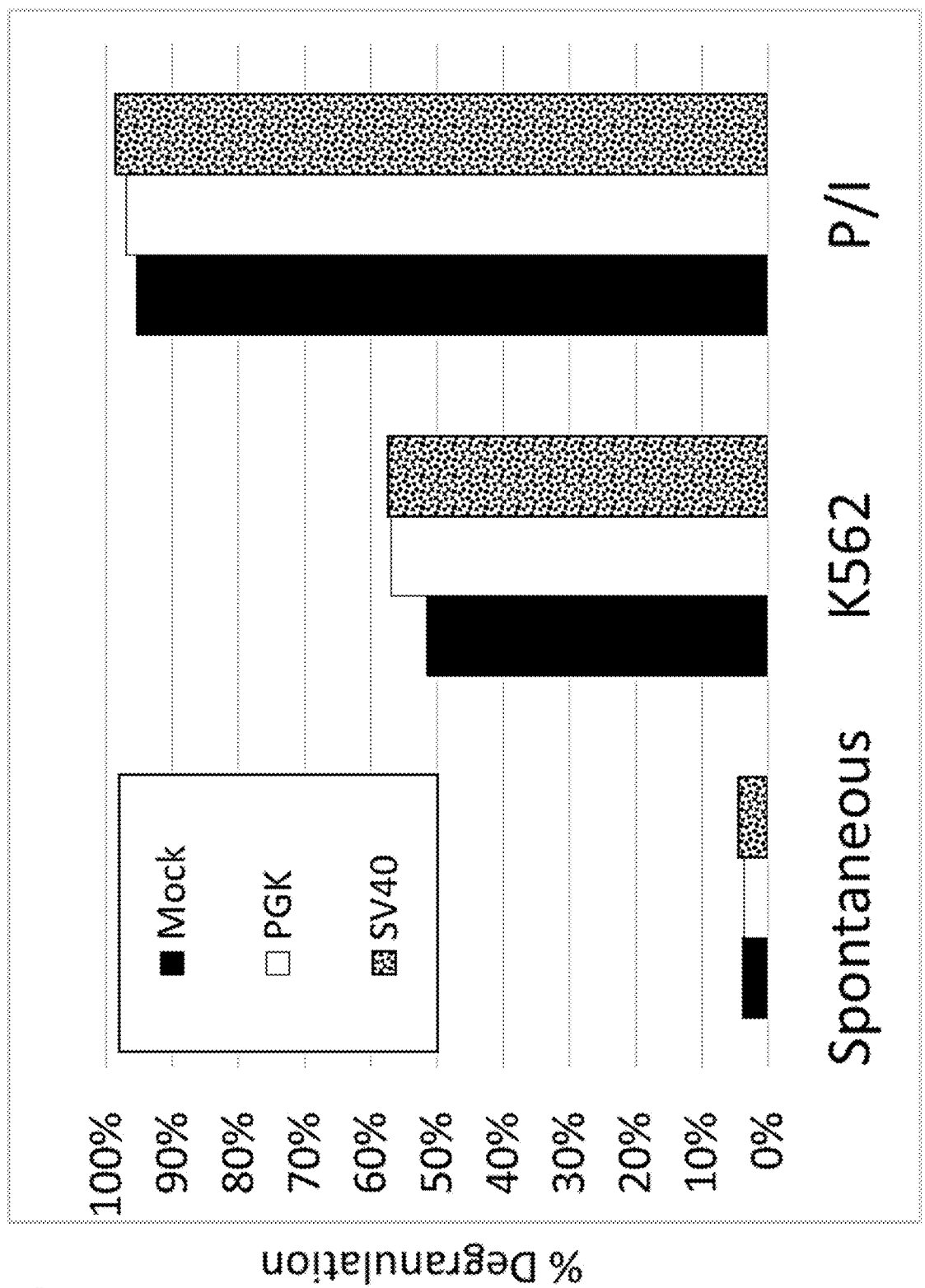

FIG. 19 is a graph showing activity (% degranulation) of NK cells transduced with GFP under the control of the indicated promoters or mock transduced cells after 14 days of expansion when contacted with K562 cells. P/I indicates treatment with PMA/ionomycin to show maximal degranulation capacity.

Figure 20:
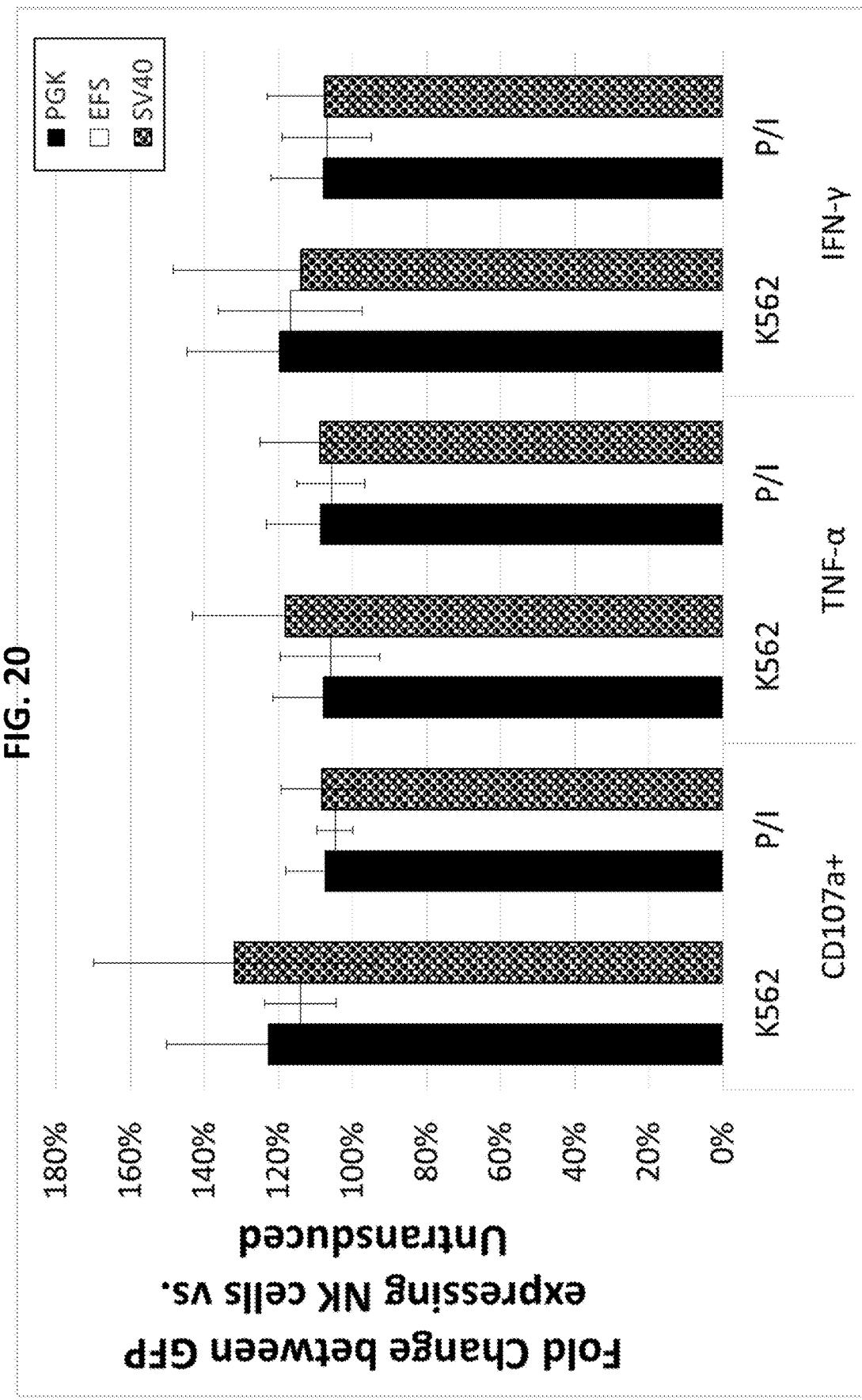

FIG. 20 is a graph showing activity of NK cells transduced with GFP under the control of the indicated promoters compared to untransduced cells after 14 days of expansion when contacted with K562 cells. P/I indicates treatment with PMA/ionomycin to show maximal degranulation capacity.

Figure 21A:
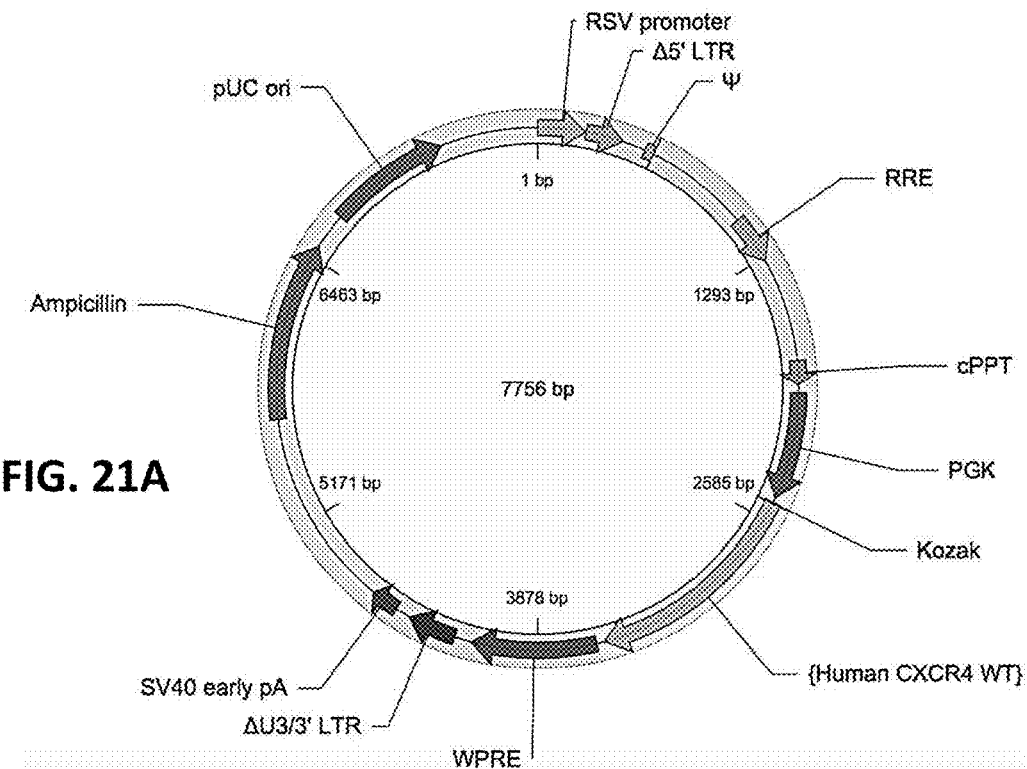
Figure 21B:
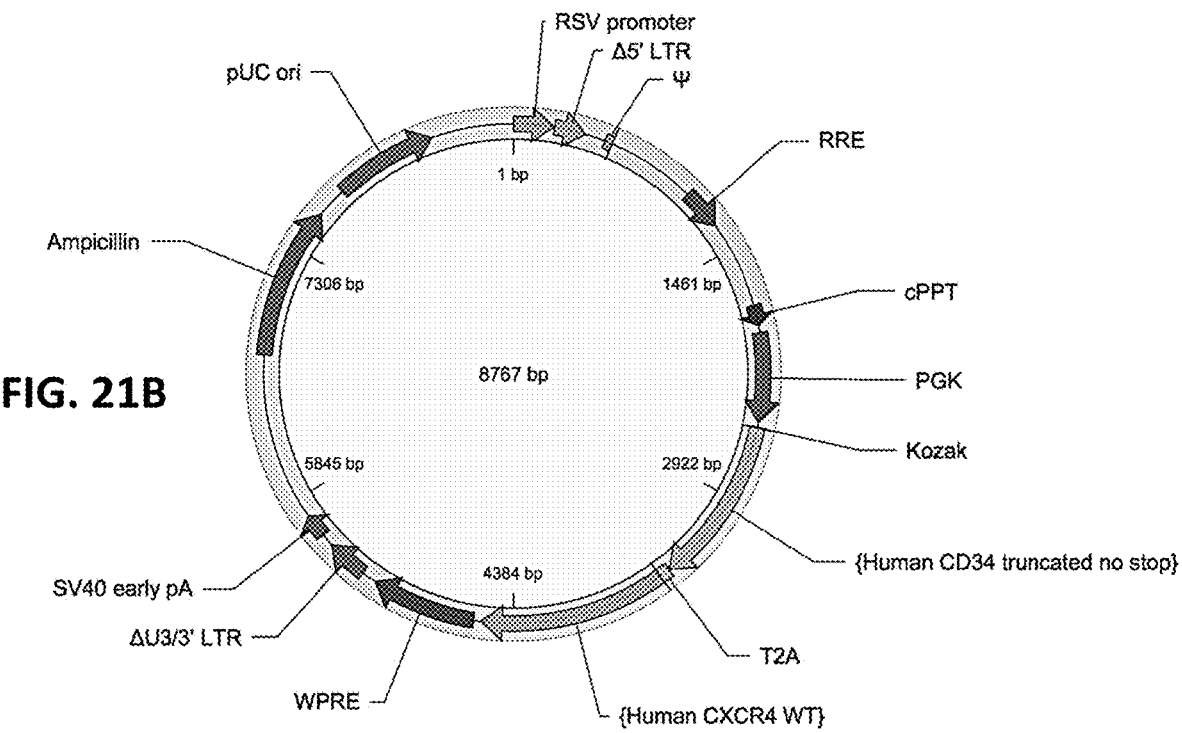

FIGS. 21A and 21B are schematic diagrams of a lentiviral vector for expression of CXCR4 (FIG. 21A) or a lentiviral vector for expression of CD34t and CXCR4 (FIG. 21B).

FIGS. 22A and 22B are plots showing CXCR4 and CD34 expression in NK cells transduced with a lentiviral vector encoding CXCR4 (FIG. 22A) or a lentiviral vector encoding both CD34t and CXCR4 (FIG. 221B).

Figure 23:
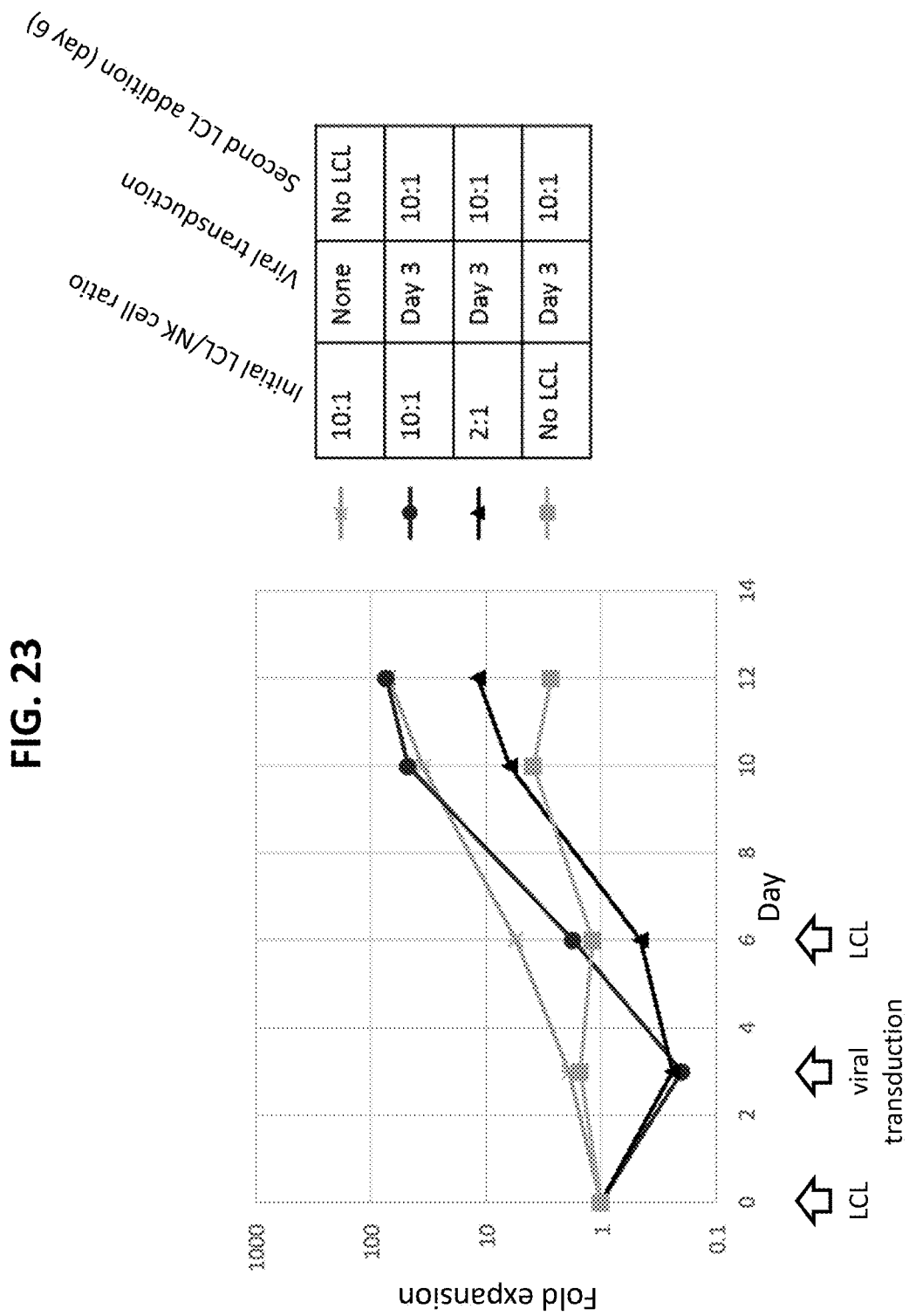

FIG. 23 is a graph showing fold-expansion of NK cells activated in the presence or absence of LCL feeder cells, followed by viral transduction and expansion in the presence or absence of LCL feeder cells.

SEQUENCE LISTING

Any nucleic acid and amino acid sequences listed herein or in the accompanying sequence listing are shown using standard letter abbreviations for nucleotide bases and amino acids, as defined in 37 C.F.R. § 1.822. In at least some cases, only one strand of each nucleic acid sequence is shown, but the complementary strand is understood as included by any reference to the displayed strand.

The Sequence Listing was submitted as an ASCII text file in the form of the file named Sequence_Listing.txt, which was created on Nov. 1, 2017, and is 126,752 bytes, which is incorporated by reference herein.

SEQ ID NOs: 1 and 2 are exemplary CXCR4 nucleic acid and amino acid sequences, respectively.

SEQ ID NOs: 3 and 4 are exemplary truncated CD34 nucleic acid and amino acid sequences, respectively.

SEQ ID NOs: 5 and 6 are exemplary high affinity CD16 nucleic acid and amino acid sequences, respectively.

SEQ ID NO: 7 is an exemplary codon-optimized high affinity CD16 nucleic acid.

SEQ ID NO: 8 is an exemplary lentiviral expression vector including human cytomegalovirus (CMV) immediate early promoter and EGFP.

SEQ ID NO: 9 is an exemplary lentiviral expression vector including human eukaryotic translation elongation factor 1α (EF1A) promoter and EGFP.

SEQ ID NO: 10 is an exemplary lentiviral expression vector including a short version of human EF1A promoter (EFS) and EGFP.

SEQ ID NO: 11 is an exemplary lentiviral expression vector including human CMV early enhancer fused with chicken β-actin (CAG) promoter and EGFP.

SEQ ID NO: 12 is an exemplary lentiviral expression vector including a short version of CAG promoter and EGFP.

SEQ ID NO: 13 is an exemplary lentiviral expression vector including simian SV40 early promoter and EGFP.

SEQ ID NO: 14 is an exemplary lentiviral expression vector including mouse phosphoglycerate kinase 1 (PGK) promoter and EGFP.

SEQ ID NO: 15 is an exemplary lentiviral expression vector including human ubiquitin C promoter and EGFP.

SEQ ID NO: 16 is an exemplary lentiviral expression vector including mouse PGK promoter and human CXCR4.

SEQ ID NO: 17 is an exemplary lentiviral expression vector including mouse PGK promoter and truncated human CD34, T2A peptide, and human CXCR4.

DETAILED DESCRIPTION

Disclosed herein are methods for efficiently and stably expressing a transgene in NK cells. The methods include an efficient viral vector-based method for gene transfer into NK cells and demonstrate stable and long-term robust expression of transgenes. High gene transfer rates into primary cells being transduced and the ability to produce high titers of virus particles for large-scale transduction of patient cells are important criteria for clinical trials. Lentiviral vectors, such as those utilized in examples herein, can be produced in high titer and concentrated without compromising their transduction efficiency. Additionally, the currently described method is cheaper and simpler to apply clinically as it does not require the need for several cumbersome and expensive steps adopted in current retroviral vector-mediated gene transfer protocols to obtain moderate transduction efficiency such as use of retronectin, spinoculation, and repeated/multiple transductions that might have a significant deleterious impact on the viability of the primary NK cells being transduced. In addition protocols for efficient ex vivo expansion of NK cells under Good Manufacturing Practice (GMP) conditions for adoptive NK cell based immunotherapy applications are available. The present highly efficient lentiviral vector-based gene transfer protocol can be used to complement a number of current ex vivo NK cell expansion protocols to generate large numbers of genetically reprogrammed NK cells, potentially revolutionizing NK cell based immunotherapeutic approaches by enhancing their antitumor efficacy in patients with cancer or viral infection.

The disclosed methods have several advantages over other methodologies for lentiviral vector-mediated genetic manipulation of human primary NK cells. The present lentiviral vector-based approach results in an efficient, robust, and highly reproducible method of stable gene transfer into primary human peripheral blood-derived NK cells. This is in contrast to episomal vectors that are lost with cell division/long-term culture, poxvirus vectors that inhibit nuclear function and eventually instigate host cell lysis, and the other non-viral-mediated gene delivery methods such as electroporation that allow only transient expression of the introduced genes. Furthermore, unlike gammaretroviral vectors, which integrate preferentially near transcription start sites and potentially activate oncogenes by promoter activation from the long terminal repeats (LTRs), lentiviral vectors integrate preferentially within highly expressed genes. Moreover, lentiviral vectors used in the disclosed methods have improved safety features such as a split genome lentiviral packaging design and have a self-inactivating design of the transfer vector through deletions in the 3' LTR, thereby reducing the potential for promoter activation.

Transduced primary NK cells obtained by the methods disclosed herein are phenotypically and functionally normal and therefore allow for a multitude of gene therapy and immunotherapy applications. Importantly, this current transduction method is simple and involves in vitro culture of NK cells with one or more cytokines, followed by exposure to concentrated viral particles. Following transduction, cells are expanded in large numbers by co-culturing them with irradiated feeder cells in media containing one or more cytokines.

I. Abbreviations

CAR chimeric antigen receptor
EBV-LCL Epstein-Barr virus transformed lymphoblastoid cell line
eGFP enhanced green fluorescent protein
FACS fluorescence-activated cell sorting
GMP good manufacturing practices
IL interleukin
LTR long terminal repeat
MOI multiplicity of infection
NK natural killer cell
PBMC peripheral blood monocyte cells
shRNA short hairpin RNA II. Terms Unless otherwise noted, technical terms are used according to conventional usage. Definitions of common terms in molecular biology may be found in *Lewin's Genes X*, ed. Krebs et al., Jones and Bartlett Publishers, 2009 (ISBN 0763766321); Kendrew et al. (eds.), *The Encyclopedia of Molecular Biology*, published by Blackwell Publishers, 1994 (ISBN 0632021829); Robert A. Meyers (ed.), *Molecular Biology and Biotechnology: a Comprehensive Desk Reference*, published by Wiley, John & Sons, Inc., 1995 (ISBN 0471186341); and George P. Rédei, *Encyclopedic Dictionary of Genetics, Genomics, Proteomics and Informatics*, 3$^{rd}$ Edition, Springer, 2008 (ISBN: 1402067534), and other similar references.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description.

Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

In order to facilitate review of the various embodiments of the disclosure, the following explanations of specific terms are provided:

Cancer: Also referred to herein as a "malignant tumor" or "malignant neoplasm." Any of a number of diseases that are characterized by uncontrolled, abnormal proliferation of cells, the potential of cancer cells to spread locally or through the bloodstream and lymphatic system to other parts of the body (e.g., metastasize), as well as any of a number of characteristic structural and/or molecular features. A "cancer cell" is a cell having specific structural properties, lacking differentiation, and being capable of invasion and metastasis.

CD34: A cell surface glycoprotein that functions as a cell-cell adhesion molecule. CD34 is a single-pass transmembrane protein with a highly glycosylated extracellular domain, a transmembrane domain, and an intracellular signaling domain. CD34 is expressed on hematopoietic cells and plays a role in cell migration. Exemplary human CD34 sequences include GenBank Accession Nos. NM_001025109 and NM_001773 (nucleic acid sequences) and NP_001020280 and NP_001764 (amino acid sequences), all of which are incorporated herein by reference as present in GenBank on Jul. 25, 2017.

Contacting: Placement in direct physical association, including both a solid and liquid form. In one example, contacting includes association between a substance (such as a cytokine) in a liquid medium and one or more cells (such as NK cells in culture). Contacting can occur in vitro with isolated cells or tissue or in vivo by administering to a subject.

Culturing or Cell culture: Growth of a population of cells in a defined set of conditions (such as culture medium, extracellular matrix, temperature, and/or time of culture) in vitro. In some examples, a cell culture includes a substantially pure culture (for example, isolated NK cells). In additional examples a cell culture includes a mixed culture, such as co-culture of two or more types of cells (for example a culture of NK cells with feeder cells). In further examples, a cell culture includes cells grown in contact with an extracellular matrix.

Culture Medium: A synthetic set of culture conditions with the nutrients necessary to support the viability, function, and/or growth of a specific population of cells, such as NK cells. Culture media generally include components such as a carbon source, a nitrogen source and a buffer to maintain pH. Additional components in culture media also may include one or more of serum (such as heat-inactivated serum), cytokines, hormones, growth factors, protease inhibitors, protein hydrolysates, shear force protectors, proteins, vitamins, glutamine, trace elements, inorganic salts, minerals, lipids, and/or attachment factors.

Cytokine: Proteins made by cells that affect the behavior of other cells, such as lymphocytes. In one embodiment, a cytokine is a chemokine, a molecule that affects cellular trafficking. The term "cytokine" is used as a generic name for a diverse group of soluble proteins and peptides that act as humoral regulators at nanomolar to picomolar concentrations and which, either under normal or pathological conditions, modulate the functional activities of individual cells and tissues. These proteins also mediate interactions between cells directly and regulate processes taking place in the extracellular environment. Examples of cytokines include, but are not limited to, tumor necrosis factor α (TNF-α), interleukin-2 (IL-2), interleukin-7 (IL-7), interleukin-15 (IL-15), interleukin-21 (IL-21), and interferon-γ (IFN-γ).

Effective amount: A quantity of a specified agent sufficient to achieve a desired effect, for example, in a subject being treated with that agent. In some examples, an effective amount of the modified NK cells disclosed herein is an amount sufficient to treat or inhibit a disease or disorder in a subject (such as a tumor, hyperproliferative disorder, or viral infection). In other examples, an effective amount is an amount of modified NK cells sufficient to reduce or ameliorate one or more symptoms of a disease or disorder in a subject. The effective amount (for example an amount ameliorating, inhibiting, and/or treating a disorder in a subject) will be dependent on, for example, the particular disorder being treated, the subject being treated, the manner of administration of the composition, and other factors.

Expression: The process by which the coded information of a gene is converted into an operational, non-operational, or structural part of a cell, such as the synthesis of a protein. Gene expression can be influenced by external signals. For instance, exposure of a cell to a hormone may stimulate expression of a hormone-induced gene. Different types of cells can respond differently to an identical signal. Expression of a gene also can be regulated anywhere in the pathway from DNA to RNA to protein. Regulation can include controls on transcription, translation, RNA transport and processing, degradation of intermediary molecules such as mRNA, or through activation, inactivation, compartmentalization or degradation of specific protein molecules after they are produced.

Feeder cells: Cells that provide support for another cell type in ex vivo or in vitro culture. Feeder cells may provide one or more factors required for survival, growth, and/or differentiation (or inhibiting differentiation) of the cells cultured with the feeder cells. Typically feeder cells are irradiated or otherwise treated to prevent their proliferation in culture. In some examples disclosed herein, NK cells are cultured with feeder cells, such as irradiated EBV-transformed lymphoblast cells (e.g., EBV-LCL cells).

Hyperproliferative disease: A disease or disorder in which the cells proliferate more rapidly than normal tissue growth. Thus, a hyperproliferating cell is a cell that is proliferating more rapidly than normal cells. In some examples, a hyperproliferative disorder includes a malignant tumor or cancer, but may also include a benign tumor.

Inhibiting or treating a condition: "Inhibiting" a condition refers to inhibiting the full development of a condition or disease, for example, a tumor. Inhibition of a condition can span the spectrum from partial inhibition to substantially complete inhibition (e.g., including, but not limited to prevention) of the disease. In some examples, the term "inhibiting" refers to reducing or delaying the onset or progression of a condition. "Treatment" refers to a therapeutic intervention that ameliorates a sign or symptom of a disease or condition after it has begun to develop. A subject to be administered an effective amount of the disclosed NK cells can be identified by standard diagnosing techniques for such a disorder, for example, presence of the disease or disorder or risk factors to develop the disease or disorder.

Isolated: An "isolated" or "purified" biological component (such as a cell, nucleic acid, peptide, protein, protein complex, or virus-like particle) has been substantially separated, produced apart from, or purified away from other components (for example, other biological components in the cell or the organism in which the component naturally occurs). Cells, nucleic acids, peptides and proteins that have been "isolated" or "purified" thus include cells, nucleic acids, and proteins purified by standard purification methods.

The term "isolated" or "purified" does not require absolute purity; rather, it is intended as a relative term. Thus, for example, an isolated biological component is one in which the biological component is more enriched than the biological component is in its natural environment within a cell, organism, sample, or production vessel (for example, a cell culture system). Preferably, a preparation is purified such that the biological component represents at least 50%, such as at least 70%, at least 80%, at least 90%, at least 95%, or greater, of the total biological component content of the preparation.

Natural Killer (NK) cells: Cells of the immune system that kill target cells in the absence of a specific antigenic stimulus and without restriction according to MHC class. Target cells can be tumor cells or cells harboring viruses. NK cells are characterized by the presence of CD56 and the absence of CD3 surface markers. NK cells typically comprise approximately 10 to 15% of the mononuclear cell fraction in normal peripheral blood. Historically, NK cells were first identified by their ability to lyse certain tumor cells without prior immunization or activation. NK cells are thought to provide a "back up" protective mechanism against viruses and tumors that might escape the CTL response by down-regulating MHC class I presentation. In addition to being involved in direct cytotoxic killing, NK cells also serve a role in cytokine production, which can be important to control cancer and infection.

In some examples, a "modified NK cell" is a NK cell transduced with a heterologous nucleic acid (such as one or more of the nucleic acids or vectors disclosed herein) or expressing one or more heterologous proteins. The terms "modified NK cell" and "transduced NK cell" are used interchangeably in some examples herein.

Pharmaceutically acceptable carrier: The pharmaceutically acceptable carriers (vehicles) useful in this disclosure are conventional. *Remington: The Science and Practice of Pharmacy*, The University of the Sciences in Philadelphia, Editor, Lippincott, Williams, & Wilkins, Philadelphia, Pa., 21' Edition (2005), describes compositions and formulations suitable for pharmaceutical delivery of one or more therapeutic compositions, such as one or more modified NK cells and/or additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example, sodium acetate or sorbitan monolaurate.

Subject: A living multi-cellular vertebrate organism, a category that includes both human and non-human mammals (such as mice, rats, rabbits, sheep, horses, cows, and non-human primates).

Transduce: Transferring nucleic acid into a cell, such as transfer of a heterologous nucleic acid into a host cell. As used herein, the term transduce (or transfect or transform) includes all techniques by which a nucleic acid is introduced into a cell, including but not limited to transformation with plasmid vectors, infection with viral vectors or viral particles, and introduction of naked DNA by electroporation, nucleofection, lipofection, or particle gun acceleration.

Transgene: A heterologous nucleic acid introduced into a cell, for example, by transduction. In some examples, a transgene is a nucleic acid encoding a protein of interest. In other examples, a transgene is a nucleic acid that is capable of modulating expression of a nucleic acid of interest, such as a short hairpin RNA (shRNA), small interfering RNA (siRNA), or antisense nucleic acid. The transgene may be operably linked to one or more expression control sequences, for example, a promoter.

A "heterologous" nucleic acid or protein refers to a nucleic acid or protein originating from a different genetic source. For example, a nucleic acid or protein that is heterologous to a cell originates from an organism or individual other than the cell in which it is expressed. In other examples, a heterologous nucleic acid or protein originates from a cell type other than the cell in which it is expressed (for example, a nucleic acid or protein not normally present in NK cells is heterologous to NK cells). In further examples, a heterologous nucleic acid includes a recombinant nucleic acid, such as a protein-encoding nucleic acid operably linked to a promoter from another gene and/or two or more operably linked nucleic acids from different sources.

Vector: A nucleic acid molecule allowing insertion of foreign or heterologous nucleic acid into a cell without disrupting the ability of the vector to replicate and/or integrate in a host cell. A vector can include nucleic acid sequences that permit it to replicate in a host cell, such as an origin of replication. A vector can also include one or more selectable marker genes and other genetic elements. An expression vector is a vector that contains the necessary regulatory sequences to allow transcription and/or translation of an inserted gene or genes. In some non-limiting examples, the vector is a viral vector, such as a retroviral vector or lentiviral vector.

II. Methods of Producing Modified NK Cells

Disclosed herein are methods of producing modified NK cells (such as NK cells including or expressing one or more heterologous nucleic acids or including all or a portion of a viral vector including one or more heterologous nucleic acids). In particular examples, the methods disclosed herein are utilized to transduce resting or short-term activated NK cells (rather than NK cell lines or expanded NK cells), which have previously been challenging to transduce with viral vectors at high efficiency.

Figure 1A:
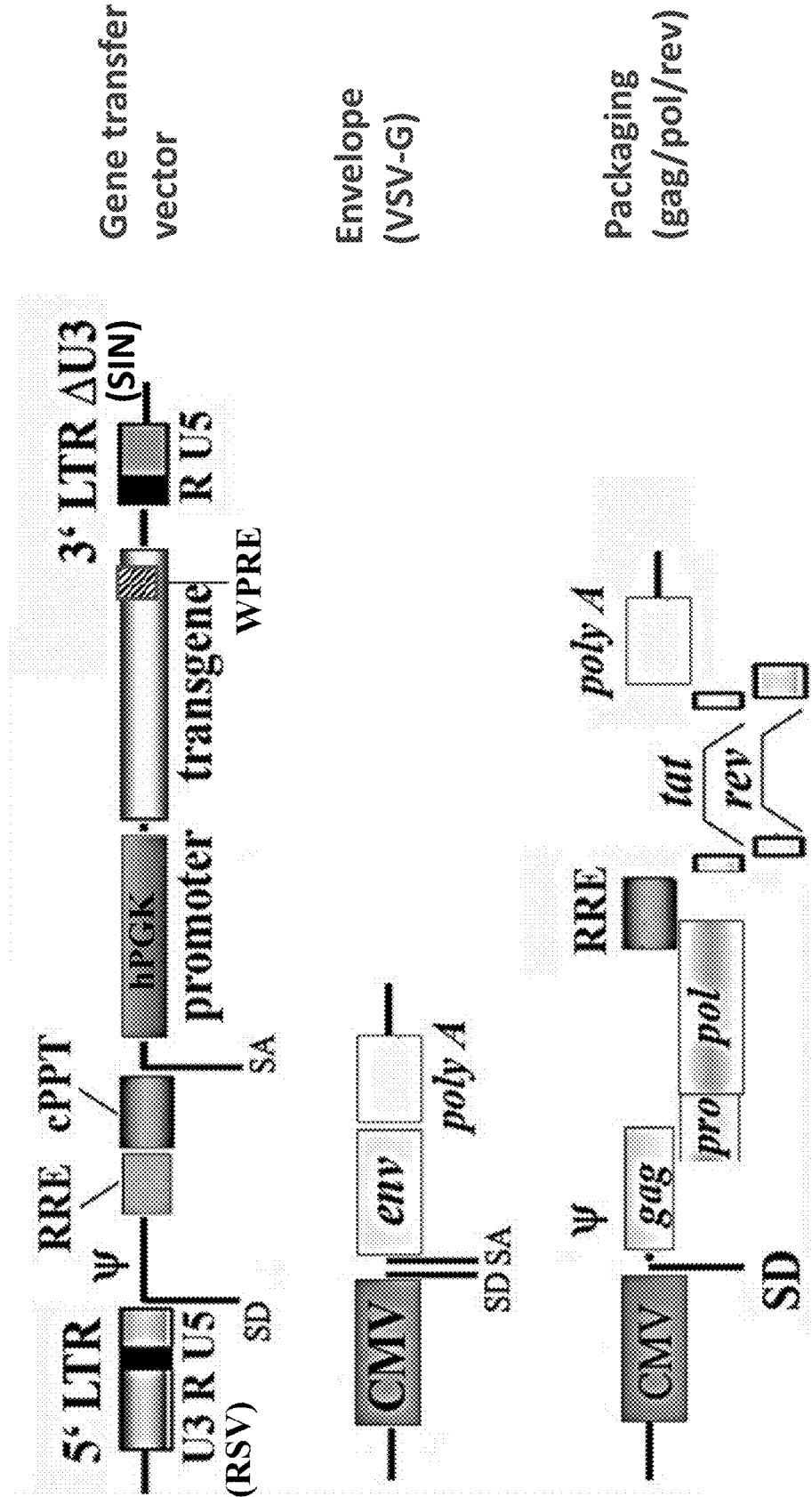

In some embodiments, the disclosed methods utilize a lentiviral system to introduce one or more heterologous nucleic acids ("transgenes") into NK cells. Lentivirus systems for virus production for transduction are generally split across multiple plasmids to increase their safety. Exemplary lentiviral systems include "second generation" systems with three plasmids or "third generation" systems with four plasmids. An exemplary three plasmid system is illustrated in FIG. 1A. The transgene nucleic acid is included in a transfer plasmid and is operably linked to a promoter (in a non-limiting example, an hPGK promoter). The transfer plasmid also includes 5' and 3' LTRs and may include additional elements, such as the psi packaging system. Lentivirus proteins for producing viral particles (such as env, gag, pol, rev, and/or tat) are encoded by two or three separate plasmids. Exemplary transfer vectors are also shown in FIGS. 21A and 21B. The lentivirus plasmids (three or four plasmids) are transfected in a mammalian cell line, which produces lentivirus particles that are not capable of replication. The lentivirus particles are then used to transduce other cells (such as NK cells). An exemplary method for producing lentiviruses (such as non-replicating lentivirus) for use in the methods disclosed herein is shown in FIG. 1B.

Figure 2:
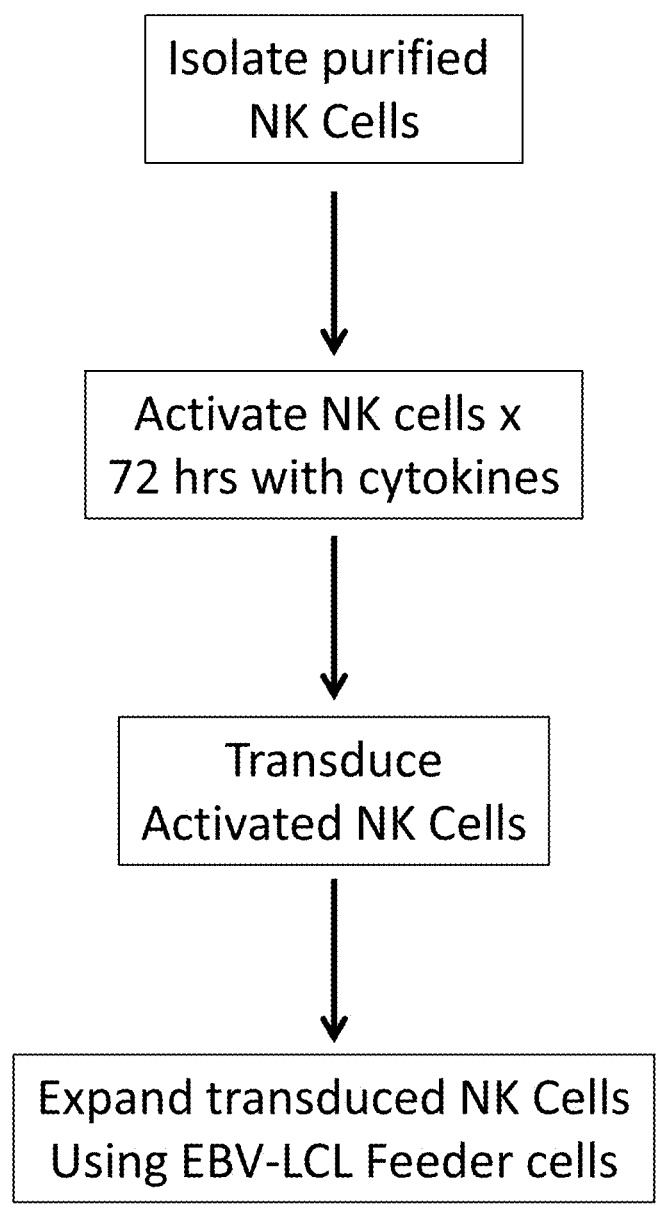
FIG. 2 is a schematic diagram illustrating an exemplary method for producing a population of expanded transduced NK cells.

In some embodiments, disclosed herein are methods for producing modified NK cells utilizing transduction with a viral vector. An overview of an exemplary process is shown in FIG. 2. In some examples, the methods include obtaining or preparing purified NK cells and activating (or "priming") the NK cells by culturing the purified NK cells in medium that includes one or more cytokines (such as IL-2, IL-15, and/or IL-21) for 1-14 days. The activated NK cells are transduced with a viral vector (such as a lentiviral vector) including one or more heterologous nucleic acids, for example, by incubating activated NK cells with the viral vector (for example, viral particles including the viral vector) for 1-3 days. The transduced NK cells are then expanded for 1-50 days (or more), for example, by culture with one or more cytokines (such as IL-2) and/or in the presence of feeder cells, to produce expanded modified NK cells. In some examples, the activated NK cells are transduced with a viral vector that includes a nucleic acid encoding a truncated CD34 protein (CD34t) lacking the intracellular signaling domain (for example a CD34t nucleic acid operably linked to another nucleic acid of interest). The CD34t protein includes the extracellular and transmembrane regions of CD34, and as a result, it is expressed on the cell surface, but does not affect activity of cells expressing the truncated protein (Norell et al., *Cancer Immunol. Immunother.* 59:851-862, 2010). To enrich for transduced cells, cells expressing CD34t (e.g., transduced cells) can be identified with an anti-CD34 antibody, and can be isolated using flow cytometry or immuno-magnetic methods. Methods for producing modified NK cells are discussed in more detail below.

In particular embodiments of the disclosed methods, purified or isolated NK cells are transduced prior to expansion and/or in the absence of feeder cells. By transducing NK cells prior to expansion, it is possible to reduce the amount of viral particles needed (such as reducing the amount of viral particles by least about 10-fold, 50-fold, 100-fold, 200-fold, 300-fold, 400-fold, 500-fold, 600-fold, 700-fold, 800-fold, 900-fold, 1000-fold, 2000-fold, 5000-fold, or 10,000-fold) than when transducing expanded NK cells. In addition, in some examples, it is simpler and/or requires less labor, cost, and/or time to transduce NK cells prior to expansion. In some examples, the inventors observed that when NK cells were contacted with viral particles in the presence of a feeder cell layer, the virus preferentially transduced the feeder cells, rather than the NK cells. Furthermore, is some examples, the transgene(s) may be toxic to the feeder cells, and may negatively impact NK cell expansion. Thus, in some non-limiting examples, NK cells are more efficiently transduced when feeder cells are not present.

In other embodiments, the NK cells are activated, transduced, and expanded in the presence of feeder cells (such as irradiated feeder cells). In some examples, NK cells are activated as described herein in the presence of feeder cells (e.g., at least 1:1 ratio (feeder cells:NK cells), for example, at least 2:1, 5:1, 10:1, 15:1, 20:1, or more) prior to transduction (for example for 1-5 days, such as 1, 2, 3, 4, or 5 days). The NK cells are then transduced and cultured for 1-5 days (such as 1, 2, 3, 4, or 5 days, for example for 3 days), still in the presence of feeder cells. The NK cells are then replated with feeder cells (for example, at least 2:1, 5:1, 10:1, 15:1, 20:1 ratio of feeder cells:NK cells) for expansion. In one non-limiting example, NK cells are isolated and plated with feeder cells at 10:1 feeder cells:NK cells. The NK cells are activated for 2-3 days with IL-2 prior to transduction. Three days after transduction, the NK cells are replated with 10:1 feeder cells:NK cells and continued to be cultured in the presence of IL-2 for expansion.

In other embodiments, the NK cells are activated in the presence of feeder cells. The feeder cells are substantially removed prior to transduction of the activated NK cells. Following transduction, the NK cells are expanded in the presence of feeder cells. In some examples, NK cells are activated as described herein in the presence of feeder cells (e.g., at least 1:1 ratio (feeder cells:NK cells), for example, at least 2:1, 5:1, 10:1, 15:1, 20:1, or more) prior to transduction (for example for 1-5 days, such as 1, 2, 3, 4, or 5 days). The feeder cells are then separated from the activated NK cells prior to transduction. In some examples, the feeder cells are removed using immunomagnetic depletion for a cell surface protein specific to the feeder cells (e.g., CD19 for LCL feeder cells). Alternatively, the feeder cells can be separated from the NK cells using an NK cell surface specific protein, such as CD56. The separated NK cells are then transduced and cultured for 1-5 days (such as 1, 2, 3, 4, or 5 days, for example for 3 days), in the absence of feeder cells. The transduced NK cells are replated with feeder cells (for example, at least 2:1, 5:1, 10:1, 15:1, 20:1 ratio of feeder cells:NK cells) for expansion. In one non-limiting example, NK cells are isolated and plated with feeder cells at 10:1 feeder cells:NK cells. The NK cells are activated for 2-3 days with IL-2 prior to transduction. Three days after transduction, the feeder cells are removed using CD19 depletion and the NK cells are replated with 10:1 feeder cells:NK cells and continued to be cultured in the presence of IL-2 for expansion.

The disclosed methods provide high efficiency transgene expression in the modified NK cells. In some embodiments, transgene expression in NK cells obtained with the disclosed methods is greater than 25%, such as at least 30%, at least 35%, at least 40%, at least 45%, at least 50%, at least 55%, at least 60%, at least 65%, at least 70%, at least 75%, at least 80%, such as 30-60%, 45-75%, 50-80%, 40-60%, or 40-50%. Transgene expression is also long-lasting post-transduction, for example for 1-10 weeks or more (such as 2-4 weeks, 3-6 weeks, 4-8 weeks, 7-10 weeks or more). In some examples, the transgene is expressed for at least 3 days, at least 5 days, at least 7 days, at least 10 days, at least 14 days, at least 21 days, at least 28 days, at least 35 days, at least 42 days, at least 49 days, at least 56 days, or more post-transduction. In other examples, the transgene expression continues for the lifetime of the NK cell either in vitro or following administration to a subject.

A. Isolation and Enrichment of NK Cells

Techniques for the in vitro isolation and enrichment of NK cells are described herein. An exemplary procedure is described in US Pat. App. Publ. No. 2014/0086890, incorporated herein by reference in its entirety. One of ordinary skill in the art can identify additional methods for expanding NK cells, for example as described in Childs et al., Hematol. *The Education Program* 2013:234-246, 2013, incorporated herein by reference in its entirety.

Mononuclear cells are collected from a subject (such as a donor subject or a subject with a tumor or hyperproliferative disease or viral infection) or from a donor HLA-matched to the subject to be treated. In some examples, mononuclear cells are collected by an apheresis procedure. The mononuclear cells are enriched for NK cells, for example by negative depletion using an immuno-magnetic bead strategy. In some examples, NK cells are enriched by depleting the mononuclear cell sample of T cells, B cells, monocytes, dendritic cells, platelets, macrophages, and erythrocytes utilizing a mixture of biotinylated monoclonal antibodies. The non-NK cells in the sample are removed with magnetic beads coupled to streptavidin, resulting in an enriched preparation of NK cells. An exemplary commercially available kit for this method is Dynabeads® Untouched™ Human NK Cells kit (ThermoFisher Scientific, Waltham, Mass.). In another example, NK cells are enriched by positive selection of CD56+ NK cells, for example utilizing magnetic beads conjugated to an anti-CD56 antibody (such as CD56 MicroBeads, Miltenyi Biotec, Inc., Auburn, Calif.). In other examples, a two-step method including negative depletion (such as T cell depletion) followed by positive selection of CD56+ NK cells is used for enriching NK cells. These methods can be carried out under or adapted for Current Good Manufacturing Practice (cGMP). One of ordinary skill in the art can identify other methods that can be used to prepare an enriched population of NK cells.

Bulk NK cells or NK cell subsets isolated by additional enriching procedures, such as through the use of immunomagnetic beads or flow sorting, may be grown in cell culture medium. In one example, the medium is Cellgro SCGM serum-free media (CellGenix, Gaithersburg, Md.) containing 10% human AB serum, 50 U/mL penicillin, 50 µg/mL streptomycin, and 500 IU/mL IL-2 or in X-VIVO™ 20 media containing 10% heat inactivated human AB serum or 10% autologous serum.

The isolated NK cells can be analyzed by flow cytometry for the expression of markers such as CD56, CD16, TRAIL, FasL, NKG2D, LFA-1, perforin, and granzymes A and B. Chromium release assays can be used to assess NK cell cytotoxicity against cell targets. One of ordinary skill in the art can identify other methods to assess the isolated NK cell population (for example, purity, viability, and/or activity).

In some embodiments, enriched NK cells (typically >99% CD3 negative and >85% CD56+) are optionally also expanded in vitro. In one non-limiting example, the enriched NK cells are cultured with an irradiated EBV-LCL feeder cell line (such as SMI-LCL) in medium including 500 IU/ml IL-2 for up to 21 days. Utilizing this technique, expansions of NK cells in the range of 200- to 1000-fold may be achieved (expanded NK cells are typically >99% CD3 negative and >90% CD56+). In some examples, the starting population of enriched NK cells is about $0.8$-$1.6 \times 10^8$ total NK cells, which over a 2-4 week period expand up to 1000-fold or greater in vitro. Similar numbers of NK cells have been expanded in scaled up experiments using GMP conditions. In some examples, NK cells are expanded in G-Rex® containers (Wilson Wolf, New Brighton, Minn.). The G-Rex®100 container supports NK expansions to doses of $2.5 \times 10^8$ NK cells/kg or higher. NK cells cultured in G-Rex®100 containers could be cultured at concentrations up to $4 \times 10^6$ NK cells/ml.

B. NK Cell Activation

The disclosed methods include activation (also referred to herein as "priming") of NK cells prior to transduction. Isolated NK cells (e.g., >95% CD3− and >85% CD56+ or >99% CD3− and >90% CD56+) are prepared as described in Section IIA or are otherwise obtained (for example, from a previous preparation, such as a cryopreserved isolated NK cell preparation). Cytokine stimulation induces metabolic activation and permits active gene expression in NK cells similar to other lymphocyte subsets, which may assist with efficient lentiviral vector mediated gene transduction.

In some embodiments of the disclosed methods, isolated NK cells (such as NK cells isolated from a subject or a donor or NK cells isolated and expanded from a subject or donor) are activated by culturing the isolated NK cells with one or more cytokines for a period of time prior to transduction. The NK cells are cultured in a culture medium including one or more cytokines for 1-14 days (such as 1-10 days, 1-7 days, 1-5 days, 2-6 days, 3-8 days, 1-4 days, or 1-3 days) prior to transduction. In some examples, the NK cells are cultured with one or more cytokines for 12 hours, 18 hours, or 1, 2, 3, 4, 5, 6, 7, 8, 9, 10, 11, 12, 13, or 14 days prior to transduction. In some examples, the NK cells are primed by culture with one or more cytokines in the absence of feeder cells. Optionally, the NK cells are primed by culture with one or more cytokines and irradiated feeder cells (such as those discussed in Section IIC) for 1-14 days prior to transduction.

The NK cells are cultured with one or more cytokines for 1-14 days prior to transduction. The one or more cytokines include IL-2, IL-15, and/or IL-21. In some examples, the NK cells are cultured in culture medium including IL-2 for 1-14 days prior to transduction (such as 1-7 days, 2-6 days, 5-10 days, or 7-14 days). IL-2 is included in the culture medium at about 10-2000 IU/ml (such as about 50-100 IU/ml, 100-500 IU/ml, 200-600 IU/ml, 500-1000 IU/ml, or 1000-2000 IU/ml, for example, about 10 IU/ml, 20 IU/ml, 50 IU/ml, 100 IU/ml, 200 IU/ml, 500 IU/ml, 1000 IU/ml, 1500 IU/ml, 2000 IU/ml, or more). In some non-limiting examples, the NK cells are activated in culture medium including 500 IU/ml IL-2 or 1000 IU/ml IL-2 for 1-6 days, 2-3 days, or 3-5 days. In other examples, the NK cells are cultured in culture medium including IL-15 for 1-14 days prior to transduction (such as 1-7 days, 2-6 days, 5-10 days, or 7-14 days). IL-15 is included in the culture medium at about 1-100 ng/ml (such as about 1-10 ng/ml, 5-20 ng/ml, 10-50 ng/ml, 25-75 ng/ml, or 50-100 ng/ml, for example, about 1 ng/ml, 5 ng/ml, 10 ng/ml, 20 ng/ml, 30 40 ng/ml, 50 ng/ml, 60 ng/ml, 70 ng/ml, 80 ng/ml, 90 ng/ml, or 100 ng/ml). In one non-limiting example, the NK cells are activated in culture medium including 10 ng/ml or 50 ng/ml IL-15 for 1-6 days, 2-3 days, or 3-5 days. In still further examples, the NK cells are cultured in culture medium including IL-2 and IL-15 for 1-14 days prior to transduction (such as 1-7 days, 2-6 days, 5-10 days, or 7-14 days), for example culture medium including 1-1000 IU/ml IL-2 and 1-100 ng/ml IL-15. In one non-limiting example, the NK cells are activated in culture medium including 500 IU/ml IL-2 and 10 ng/ml or 50 ng/ml IL-15 for 1-6 days, 2-3 days, or 3-5 days. In other examples, the NK cells are cultured in culture medium including IL-2 and IL-21 for 1-14 days prior to transduction (such as 1-7 days, 2-6 days, 5-10 days, or 7-14 days), for example culture medium including 1-1000 IU/ml IL-2 and 1-100 ng/ml IL-21. In one non-limiting example, the NK cells are activated in culture medium including 500 IU/ml IL-2 and 20 ng/ml IL-21 for 1-6 days, 2-3 days, or 3-5 days. In another example, the NK cells are cultured in culture medium including 1-1000 IU/ml IL-2, 1-100 ng/ml IL-15, and 1-100 ng/ml IL-21 for 1-14 days prior to transduction (such as 1-7 days, 2-6 days, 5-10 days, or 7-14 days). In one non-limiting example, the NK cells are activated in culture medium including 500 IU/ml IL-2, 10 ng/ml IL-15, and 20 ng/ml IL-21 for 1-6 days, 2-3 days, or 3-5 days.

C. Transduction and Expansion of Transduced NK Cells

The activated (primed) NK cells, such as those described in Section IIB are transduced with a viral vector including one or more heterologous nucleic acids, such as one or more nucleic acids encoding a protein of interest or another nucleic acid of interest (such as an shRNA). In particular non-limiting examples, the vector is a lentiviral vector.

Viral vectors suitable for gene delivery to NK cells include retrovirus, adenovirus, adeno-associated virus, vaccinia virus, fowlpox, and lentivirus vectors. In particular non-limiting examples disclosed herein, NK cells are transduced with lentiviral vectors including one or more heterologous nucleic acids of interest. Some advantages of using a lentiviral system include long-term expression of the transgene, the ability to transduce both dividing cells and non-dividing cells, the ability to deliver complex genetic elements, lack of expression of viral proteins after transduction, lack of insertional mutagenesis in human cells, high titer production, and ease of vector manipulation and production.

Disclosed herein are lentiviral vectors or constructs including one or more heterologous nucleic acids of interest. In particular examples, the nucleic acid(s) of interest (such as those described in Section III) is included in a lentiviral gene transfer vector (see, e.g., FIG. 1A). The nucleic acid(s) of interest in the transfer vector is operably linked to one or more expression control elements, such as a promoter. Exemplary promoters include constitutive promoters such as cytomegalovirus (CMV), SV40, phosphoglycerate kinase (PGK), ubiquitin C (UBC), elongation factor-1 (EFS), chicken β-action short promoter (CBH), EF-1 alpha (EF1a) promoter, or EF1a short promoter (EFS), a hybrid promoter (such as a CMV enhancer fused to chicken β-actin promoter (CAG)), or an inducible or tissue-specific promoter. In other examples, for example when the nucleic acid of interest is a shRNA, the nucleic acid may be operably linked to an RNA polymerase III promoter, such as a U6 or H1 promoter.

Additional expression control elements that may be included in the transfer vector include sequences that control or regulate transcription and/or translation of a nucleic acid, such as enhancers, leader sequences, transcription terminators, start and/or stop codons, internal ribosome entry sites (IRES), splicing signals, and polyadenylation signals. In examples where the vector or construct includes two (or more) heterologous nucleic acids of interest, the nucleic acids are operably linked, for example, separated by an IRES or other multicistronic element such as a P2A and/or T2A element. The vector may also contain additional elements such as packaging signals (e.g., lentivirus ψ packaging signal), a central polypurine tract (cPPT), a woodchuck hepatitis virus post-transcriptional regulatory element (WPRE), or a Rev Response element (RRE). In some examples, the lentivirus vector is self-inactivating.

Lentivirus vectors including one or more nucleic acids of interest can be prepared by one of ordinary skill in the art utilizing conventional molecular biology techniques. For example, the nucleic acid of interest can be cloned into a lentivirus transfer vector. Lentivirus plasmid systems (such as 3 or 4 plasmid systems) are commercially available, for example from Clontech (Mountain View, Calif.), ThermoFisher Scientific (Waltham, Mass.), or Addgene (Cambridge, Mass.). In some examples, lentivirus vectors are modified to suit a particular use, such as to obtain sustained in hematopoietic cells. In some examples, the modifications include one or more of the modifications described in Example 1, below.

In some embodiments, the lentiviral vector includes or consists of a nucleic acid sequence with at least 90% sequence identity (such as at least 90%, 91%, 92%, 93%, 94%, 95%, 96%, 97%, 98%, 99%, or 100% identity) to any one of SEQ ID NOs: 8-17. In some non-limiting examples, the lentiviral vector includes or consists of the nucleic acid sequence of any one of SEQ ID NOs: 8-17. A vector map of SEQ ID NO: 16 is shown in FIG. 21A and a vector map of SEQ ID NO: 17 is shown in FIG. 21B.

In some embodiments, the disclosed lentiviral vectors include a promoter operably linked to a nucleic acid(s) of interest. The promoter and/or the nucleic acid(s) of interest in SEQ ID NOs: 8-17 can be replaced with any promoter and/or nucleic acid(s) of interest. For example, the vectors of SEQ ID NOs: 16 and 17 include the PGK promoter (e.g., at nucleotide positions 1959-2469); however, this promoter could be replaced with a different promoter, such as the EFS promoter (e.g., nucleotides positions 1959-2190 of SEQ ID NO: 10). Alternatively, the nucleic acid linked to the promoter can be replaced with an alternative nucleic acid(s) for expression. In one example, the vector of SEQ ID NO: 10 includes the EFS promoter (e.g., at nucleotide positions 1959-2190) linked to a nucleic acid encoding EGFP (nucleotide positions 2221-2940). The nucleic acid encoding EGFP in the vectors disclosed herein can be replaced with a nucleic acid encoding a different nucleic acid of interest, including but not limited to a nucleic acid encoding CXCR4, CD16, CD34t, (nucleic acid positions in SEQ ID NOs: 16 and 17 are shown Table 3) or a nucleic acid encoding other nucleic acid(s) of interest, such as the transgenes shown in Table 1. In particular examples, the nucleic acid of interest is operably linked to a PGK, EFS, or SV40 promoter. Other elements of the disclosed vectors (shown in Table 4) can also be changed (for example, replaced) or modified, as desired.

Lentivirus particles are produced by transfecting a mammalian cell line (such as 293T cells or a derivative thereof) with the plasmids of the lentivirus system (such as the three plasmid system illustrated in FIG. 1A). Transfection is carried out by standard methods, for example utilizing calcium-phosphate or polyethylenimine-mediated transfection or commercially available transfection reagents such as Lipofectamine® (ThermoFisher Scientific, Waltham, Mass.), FuGene® (Promega, Madison, Wis.), Universal Transfection Reagent (Sigma-Aldrich, St. Louis, Mo.), or SuperFect® (Qiagen, Valencia, Calif.) transfection reagents. Following transfection, lentiviral particles are released into the culture medium and are harvested. In some examples, the transfected cells are cultured for about 18-72 hours (for example, about 18-36 hours, 24-48 hours, or 36-72 hours, such as 18, 24, 36, 48, 60, or 72 hours). The virus-containing medium, which contains the packaged lentivirus particles, is harvested. In some examples, the virus is concentrated (such as by about 2-fold, 5-fold, 10-fold, 20-fold, 50-fold, 100-fold, or more) for example, by ultracentrifugation of the culture supernatant. The virus preparation can be analyzed to determine the number of viral particles in a particular volume (e.g., pfu/ml, for example by p24 ELISA) or to determine the number of particles including the RNA of interest (e.g., transducing units (TU)/ml, for example by FACS analysis). In some examples, the concentrated virus preparation contains about $10^7$-$10^{10}$ TU/ml (e.g., about $10^7$-$10^9$, $10^8$-$10^{10}$, or $10^8$-$10^9$ TU/ml).

Transduced NK cells are produced by contacting the activated NK cells described in Section IIB with the lentiviral particles, for example at a multiplicity of infection (MOI) of about 0.5 to 200 (such as about 0.5-5, 1-10, 5-15, 10-25, 20-50, 40-80, 60-100, 75-150, or 100-200, for example, about 0.5, 1, 2, 5, 10, 15, 20, 25, 30, 40, 50, 60, 70, 80, 90, 100, 125, 150, 175, or 200). In some examples, the NK cells are contacted with virus at an MOI of about 10-20 or an MOI of about 20. In some examples, the transduction is in the presence of one or more additional compounds, such as protamine sulfate (for example, 5-50 µg/ml, such as 5, 10, 20, 30, 40, or 50 µg/ml) or hexadimethrine bromide (e.g., Polybrene®, for example about 4-40 µg/ml, such as 4, 8, 16, 20, 24, 28, 32, 36, or 40 µg/ml), or a fibronectin fragment (e.g., Retronectin®). The cells are cultured with the viral particles for about 6 hours to 5 days (for example, about 6-24 hours, 12-48 hours, 24-72 hours, 48-60 hours, or 72-96 hours), such as about 1, 2, 3, 4, or 5 days.

Following transduction of the NK cells with the lentivirus, the viral particles are removed (for example by exchanging the culture medium and optionally washing the cells). In some examples, NK cells expressing the transgene are optionally selected prior to expansion (below). For example, if the transgene is expressed on the cell surface, NK cells expressing the transgene may be enriched by immuno-magnetic techniques or flow cytometry. For example, if the NK cells are transduced with a vector including a nucleic acid encoding a truncated CD34 molecule (CD34t), transduced NK cells can be selected or enriched by contacting the population of transduced NK cells with an anti-CD34 antibody and purifying CD34-expressing cells for example, using flow cytometry or immuno-magnetic beads (e.g., CliniMACS® CD34 reagent system, Miltenyi Biotec Inc., San Diego, Calif. or Isolex® 300 magnetic cell selection system, Nexell Therapeutics Inc., Irvine, Calif.), for example about 2-4 days after transduction.

The transduced NK cells are then expanded by culturing the cells for 1-40 days or more (such as 3-14 days, 5-21 days, 7-28 days, 14-30 days, 21-40 days, or more, for example, 1, 3, 5, 7, 10, 14, 21, 28, 35, 42 days, or more). In some examples, the transduced NK cells are expanded in cell culture medium containing at least one cytokine. In some examples, the transduced NK cells are expanded by culturing in a medium (such as X-VIVO™ 20 or X-VIVO™ 15 medium (Lonza, Basel, Switzerland)) including IL-2 (such as 1-1000 IU/ml, for example, 500 IU/ml IL-2). In some embodiments, one or more additional cytokines can be utilized in the expansion of the transduced NK cells, including but not limited to IL-18, IL-7, IL-15, and/or IL-12.

In some examples, feeder cells (such as irradiated feeder cells) are added to the transduced NK cell culture during the expansion step. The feeder cells are added in an amount that can support expansion of the NK cells, such as at least 2:1 ratio (feeder cells:NK cells), for example, 5:1, 10:1, 15:1, 20:1, or more. Exemplary feeder cells include EBV-LCLs (TM-LCL, SMI-LCL), allogeneic or autologous PBMCs, Wilms tumor cell line HFWT, and K562 cells (such as genetically modified K562 cells, for example, K562-mb15-41BBL or K562-mbIL-21 cells). In some examples, the transduced NK cells are mixed with the feeder cells at the selected ratio and the cell mixture is plated.

Utilizing these techniques, expansion of the transduced NK cells in the range of 100- to 1000-fold (such as 200- to 500-fold, 300- to 700-fold, or 600- to 1000-fold) may be achieved.

Following expansion, the modified NK cells are separated from the feeder cells (if used). The modified NK cells are washed one or more times and resuspended in an appropriate buffer or other pharmaceutically acceptable carrier, for example, for administration to a subject. In some examples, the cells are harvested and washed (for example in a buffer, such as phosphate buffered saline). The NK cells may be resuspended in a medium containing PLASMA-LYTE™ multiple electrolytes injection (Baxter Healthcare), autologous plasma, or a pharmaceutically acceptable carrier (for example, a balanced salt solution). In some examples, some or all of the modified NK cells are cryopreserved for later use.

In some examples, the modified NK cells are tested prior to administering to a subject, for example, for one or more of cell viability, tumor cell cytotoxicity, and transgene expression. In additional examples, the phenotype of the modified NK cells is assessed prior to administration, such as by measuring presence and/or amount of one or more cell surface markers (such as CD56, CD16, TRAIL, FasL, NKG2D, LFA-1, perforin, or granzymes A and B), for example by flow cytometry.

III. Modified NK Cells

Disclosed herein are NK cells including a heterologous nucleic acid or expressing one or more heterologous proteins or a nucleic acid of interest (referred to herein as "modified NK cells"). Modified or recombinant NK cells containing one or more heterologous nucleic acids can be produced by transducing NK cells with virus particles including a vector (such as a lentivirus vector) with the one or more heterologous nucleic acids, for example using the methods disclosed herein. The modified NK cells can be formulated into a therapeutic composition for administration to a subject, for example, with one or more pharmaceutically acceptable carriers. Therapeutic compositions and methods of their use are discussed in Section IV, below.

The modified NK cells are NK cells that have been transduced with a viral vector or virus particle (such as a lentiviral vector or lentivirus particle) including one or more transgenes, such as one or more heterologous nucleic acids encoding a protein of interest or capable of regulating expression of another nucleic acid or protein (such as an shRNA, siRNA, or antisense nucleic acid). In some embodiments, the nucleic acid encodes a protein that facilitates targeting of the modified NK cells expressing the protein to a target tissue or cell type. For example, the nucleic acid can encode a protein that increases targeting of an NK cell expressing the protein to tumor cells or sites of tumor cells. In one non-limiting example, the transgene increases targeting of NK cells to bone marrow or lymph nodes (for example, C—C chemokine receptor type 7 (CCR7), C—X—C chemokine receptor type 4 (CXCR4; e.g., wild type CXCR4 or CXCR4 R334X), or CD34) or sites of inflammation (such as C—X—C chemokine receptor type 3 (CXCR3)). In other examples, the transgene encodes a protein that binds to an epitope expressed on tumor cells (such as a chimeric antigen receptor (CAR)). In other embodiments, the nucleic acid encodes a protein that increases antibody-dependent cell mediate cytotoxicity of NK cells, such as high affinity CD16 (CD16-V158).

Thus, in particular examples, the modified NK cells disclosed herein are NK cells (such as a population of NK cells) that include a heterologous nucleic acid encoding a chemokine receptor, such as CXCR4, CCR7, or CXCR3. In other examples, the modified NK cells are NK cells (such as a population of NK cells) that include a heterologous nucleic acid encoding a cell surface protein, such as CD16 (for example, CD16-V158), CD34, double negative TGFβ type II receptor, VLA-4 (alpha4beta-1), or LFA-1. In additional examples, the modified NK cells are NK cells (such as a population of NK cells) that include a heterologous nucleic acid encoding a chimeric antigen receptor (CAR), for example CD19-CAR, CD2O-CAR, CD33-CAR, CD138-CAR, CS1-CAR, GD2-CAR, HER2-CAR, erbB2-CAR, carcinoembryonic antigen (CEA)-CAR, epithelial cell adhesion molecule (EpCAM)-CAR, natural-killer group 2, member D, long form (NKG2D-L)-CAR, or TRAIL receptor 1 (TRAIL-R1)-CAR. In still further examples, the modified NK cells are transduced with recombinant TRAIL (e.g., to enhance NK cell TRAIL-mediated tumor killing) DR5-specific TRAIL, recombinant FAS-Ligand (e.g. to enhance FAS-Ligand mediated tumor killing), DNAM-1 (e.g., to enhance NK cell activation and tumor killing), NK cell activating receptors such as NKG2D, DNAM-1, NKp30, NKp44, or NKp46 (e.g., to enhance tumor killing), or NKG2C (e.g., to enhance NK cell killing of viral infected cells).

In one non-limiting example, the modified NK cells include a heterologous nucleic acid encoding CXCR4 operably linked to a promoter (such as a PGK promoter) or nucleic acids encoding CD34t and CXCR4 operably linked to a promoter (such as a PGK promoter). In other non-limiting examples, the modified NK cells include a heterologous nucleic acid encoding high affinity CD16 operably linked to a promoter (such as a PGK promoter) or nucleic acids encoding CD34t and high affinity CD16 operably linked to a promoter (such as a PGK promoter). In another non-limiting example, the modified NK cells include a heterologous nucleic acids encoding CXCR4 and high affinity CD16 operably linked to a promoter (such as a PGK promoter) or nucleic acids encoding CD34t, CXCR4, and high affinity CD16 operably linked to a promoter (such as a PGK promoter). In some examples, the nucleic acid encoding CXCR4 includes or consists of a nucleic acid with at least 90% identity (such as at least 90%, 91%, 92%, 93%, 94%, 95%, 96%, 97%, 98%, 99%, or 100% identity) to SEQ ID NO: 1 and/or encodes a protein including or consisting of an amino acid sequence with at least 95% identity (such as at least 95%, 96%, 97%, 98%, 99%, or 100% identity) to SEQ ID NO: 2. In some examples, the nucleic acid encoding CD34t includes or consists of a nucleic acid with at least 90% identity (such as at least 90%, 91%, 92%, 93%, 94%, 95%, 96%, 97%, 98%, 99%, or 100% identity) to SEQ ID NO: 3 and/or encodes a protein including or consisting of an amino acid sequence with at least 95% identity (such as at least 95%, 96%, 97%, 98%, 99%, or 100% identity) to SEQ ID NO: 4. In some examples, the nucleic acid encoding high affinity CD16 includes or consists of a nucleic acid with at least 90% identity (such as at least 90%, 91%, 92%, 93%, 94%, 95%, 96%, 97%, 98%, 99%, or 100% identity) to SEQ ID NO: 5 or SEQ ID NO: 6 and/or encodes a protein including or consisting of an amino acid sequence with at least 95% identity (such as at least 95%, 96%, 97%, 98%, 99%, or 100% identity) to SEQ ID NO: 7.

In other examples, the modified NK cells can be transduced with a viral vector including a nucleic acid coding for small interfering RNAs (siRNAs), such as small hairpin RNA (shRNA). In one example, the modified NK cells are NK cells (such as a population of NK cells) that include a heterologous NKG2A shRNA nucleic acid.

IV. Methods of Treating or Inhibiting a Condition

Disclosed herein are methods of treating a subject with a disease or disorder by administering the modified NK cells described herein to the subject. The modified NK cells described herein can be administered either to animals or to human subjects. In some embodiments, the disease or disorder is a tumor or hyperproliferative disease. In other embodiments, the disease or disorder is a viral infection (including but not limited to cytomegalovirus, adenovirus, respiratory syncytial virus, Epstein-Barr virus, or human immunodeficiency virus infection).

The modified NK cells described herein can be incorporated into pharmaceutical compositions. Such compositions typically include a population of modified NK cells and a pharmaceutically acceptable carrier. A "pharmaceutically acceptable carrier" includes any and all solvents, dispersion media, coatings, antibacterial and antifungal agents, isotonic and absorption delaying agents, and the like, compatible with pharmaceutical administration (see, e.g., Remington: The Science and Practice of Pharmacy, The University of the Sciences in Philadelphia, Editor, Lippincott, Williams, & Wilkins, Philadelphia, Pa., 21$^{st}$ Edition, 2005). Examples of such carriers or diluents include, but are not limited to, water, saline, Ringer's solutions, dextrose solution, balanced salt solutions, and 5% human serum albumin. Liposomes and non-aqueous vehicles such as fixed oils may also be used. Supplementary active compounds can also be incorporated into the compositions. Actual methods for preparing administrable compositions are known or apparent to those skilled in the art and are described in more detail in such publications as Remington: The Science and Practice of Pharmacy, The University of the Sciences in Philadelphia, Editor, Lippincott, Williams, & Wilkins, Philadelphia, Pa., 21$^{st}$ Edition (2005). In one non-limiting example, the transduced NK cells are suspended in PLASMA-LYTE™ multiple electrolyte solution.

In some examples, the composition includes about $10^4$ to $10^{12}$ of the modified NK cells (for example, about $10^4$-$10^7$ cells, about $10^6$-$10^9$ cells, or about $10^8$-$10^{12}$ cells). For example, the composition may be prepared such that about $10^6$ to $10^{10}$ modified NK cells/kg (such as about $10^6$, $10^7$, $10^8$, $10^9$, or $10^{10}$ cells/kg) are administered to a subject. The population of modified NK cells is typically administered parenterally, for example intravenously; however, injection or infusion to a tumor or close to a tumor (local administration) or administration to the peritoneal cavity can also be used. One of skill in the art can determine appropriate routes of administration.

Multiple doses of the population of modified NK cells can be administered to a subject. For example, the population of modified NK cells can be administered daily, every other day, twice per week, weekly, every other week, every three weeks, monthly, or less frequently. A skilled clinician can select an administration schedule based on the subject, the condition being treated, the previous treatment history, and other factors.

In additional examples, the subject is also administered one or more cytokines (such as IL-2, IL-15, IL-21, and/or IL-12) to support survival and/or growth of NK cells. The cytokine(s) are administered before, after, or substantially simultaneously with the NK cells. In some examples, the cytokine(s) are administered after the NK cells. In one specific example, the cytokine(s) is administered to the subject within about 1-8 hours (such as within about 1-4 hours, about 2-6 hours, about 4-6 hours, or about 5-8 hours) after administration of the NK cells.

In some examples, the methods include treating or inhibiting a hyperproliferative disorder, such as a hematological malignancy or a solid tumor. Examples of hematological malignancies include leukemias, including acute leukemias (such as 11q23-positive acute leukemia, acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), T-cell large granular lymphocyte leukemia, polycythemia vera, lymphoma, diffuse large B-cell lymphoma, Hodgkin's lymphoma, non-Hodgkin's lymphoma (indolent and high grade forms), mantle cell lymphoma, follicular cell lymphoma, multiple myeloma, Waldenstrom's macroglobulinemia, heavy chain disease, myelodysplastic syndrome, hairy cell leukemia and myelodysplasia.

Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer (including basal breast carcinoma, ductal carcinoma and lobular breast carcinoma), lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytoma, sebaceous gland carcinoma, papillary carcinoma, papillary adenocarcinoma, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyrgioma, ependymoma, pinealoma, hemangioblastoma, acoustic neuroma, oligodendroglioma, meningioma, melanoma, neuroblastoma, and retinoblastoma).

In particular examples, hematological malignancies that can be inhibited or treated by the methods disclosed herein include but are not limited to multiple myeloma, chronic lymphocytic leukemia, acute lymphocytic leukemia, acute myeloid leukemia, chronic myelogenous leukemia, pro-lymphocytic/myelocytic leukemia, plasma cell leukemia, NK cell leukemia, Waldenstrom macroglobulinemia, Hodgkin's lymphoma, non-Hodgkin's lymphoma, mantle cell lymphoma, diffuse large B-cell lymphoma, and follicular lymphoma. In additional particular examples, solid tumors that can be treated or inhibited by the methods disclosed herein include lung carcinoma, prostate cancer, pancreatic cancer (for example, insulinoma), breast cancer, colorectal adenocarcinoma or squamous cell carcinoma, neuroblastoma, testicular cancer (such as seminoma), and ovarian cancer. In specific, non-limiting examples, the subject has chronic myelogenous leukemia or acute monocytic leukemia. Exemplary transgenes for expression by modified NK cells that can be used for treating a subject with exemplary disorders are shown in Table 1. However, one of ordinary skill in the art can select NK cells expressing an appropriate transgene for treating a subject with other disorders.

TABLE 1

Exemplary modified NK cells for treating particular disorders

| Transgene Expressed by Modified NK Cells | Disorder |
|---|---|
| CD16 V158 | Multiple tumor types, including multiple myeloma and lymphoma |
| CCR7 | Lymphoma |
| CXCR3 | Tumor metastases |
| CXCR4 | Breast cancer, kidney cancer, multiple myeloma |
| CD34 | Leukemia |
| CD19-CAR | B cell malignancies |
| CD20-CAR | B cell malignancies |
| CD33-CAR | leukemia |
| CS1-CAR | Myeloma |
| CD138-CAR | Myeloma |
| GD2-CAR | Neuroblastoma, melanoma |
| Her2/Neu-CAR | Breast cancer |
| ErbB2-CAR | Breast cancer |
| CEA-CAR | Colon cancer |
| EpCAM-CAR | Epithelial tumors |
| NKG2D-CAR | Leukemia, solid tumors |
| TRAIL-R1-CAR | Multiple tumor types |
| DNTβRII | Lung cancer |
| TRAIL | Multiple tumor types |
| FAS-Ligand | Multiple tumor types |
| DNAM-1 | Multiple tumor types |
| NKG2D | Multiple tumor types |
| NKp30 | Multiple tumor types |
| NKp44 | Multiple tumor types |
| NKp46 | Multiple tumor types |
| NKG2C | Viral infection |
| NKG2A shRNA | Leukemia |

In some examples, the subject (such as a subject with a tumor or hyperproliferative disorder) is also administered one or more chemotherapeutic agents and/or radiation therapy. One of skill in the art can select additional chemotherapeutic agents for administration to a subject in combination with the modified NK cells described herein, for example, based on the type of tumor or disorder being treated). Such agents include alkylating agents, such as nitrogen mustards (such as mechlorethamine, cyclophosphamide, melphalan, uracil mustard or chlorambucil), alkyl sulfonates (such as busulfan), nitrosoureas (such as carmustine, lomustine, semustine, streptozocin, or dacarbazine); antimetabolites such as folic acid analogs (such as methotrexate), pyrimidine analogs (such as 5-FU or cytarabine), and purine analogs, such as mercaptopurine or thioguanine; or natural products, for example vinca alkaloids (such as vinblastine, vincristine, or vindesine), epipodophyllotoxins (such as etoposide or teniposide), antibiotics (such as dactinomycin, daunorubicin, doxorubicin, bleomycin, plicamycin, or mitocycin C), and enzymes (such as L-asparaginase). Additional agents include platinum coordination complexes (such as cis-diamine-dichloroplatinum II, also known as cisplatin), substituted ureas (such as hydroxyurea), methyl hydrazine derivatives (such as procarbazine), and adrenocrotical suppressants (such as mitotane and aminoglutethimide); hormones and antagonists, such as adrenocorticosteroids (such as prednisone), progestins (such as hydroxyprogesterone caproate, medroxyprogesterone acetate, and magestrol acetate), estrogens (such as diethylstilbestrol and ethinyl estradiol), antiestrogens (such as tamoxifen), and androgens (such as testosterone proprionate and fluoxymesterone). Examples of the most commonly used chemotherapy drugs include adriamycin, melphalan (Alkeran®) Ara-C (cytarabine), carmustine, busulfan, lomustine, carboplatinum, cisplatinum, cyclophosphamide (Cytoxan®), daunorubicin, dacarbazine, 5-fluorouracil, fludarabine, hydroxyurea, idarubicin, ifosfamide, methotrexate, mithramycin, mitomycin, mitoxantrone, nitrogen mustard, paclitaxel (or other taxanes, such as docetaxel), vinblastine, vincristine, VP-16, while newer drugs include gemcitabine (Gemzar®), trastuzumab (Herceptin®), irinotecan (CPT-11), leustatin, navelbine, rituximab (Rituxan®) imatinib (STI-571), Topotecan (Hycamtin®), capecitabine, ibritumomab (Zevalin®), and calcitriol.

In some particular examples, the modified NK cells express CD16 V158 and the additional agent is an anti-cancer monoclonal antibody. In specific, non-limiting examples, modified NK cells expressing CD16-V158 are administered to a subject with multiple myeloma in combination with an antibody that binds to CD38 (such as daratumumab). In another particular example, modified NK cells expressing CD16-V158 are administered to a subject with lymphoma in combination with an antibody that binds to CD20 (such as rituximab). Additional exemplary monoclonal antibodies that can be administered to a subject in combination with modified NK cells expressing CD16-V158 are provided in Table 2.

TABLE 2

Exemplary therapeutic monoclonal antibodies for administration in combination with NK cells expressing CD16-V158

| Antigen | mAb | Target Tumor/Disease |
|---|---|---|
| CD19 | GBR 401, MEDI-551 | B cell lymphoma, CLL |
| CD20 | Rituximab (RITUXAN ®), ofatumumab (ARZERRA ®), veltuzumab | Non-Hodgkin's lymphoma |
|  | Ibritumomab tiuxetan (ZEVALIN ®), obinutuzumab, ublituximab, tositumomab (BEXXAR ®), ocaratuzumab | Lymphoma |
| CD22 | Narnatumab, inotuzumab ozogamicin | Cancer |
| CD30 | Brentuximab vedotin (ADCETRIS ®), iratumumab | Hodgkin's lymphoma |
| CD33 | Gemtuzumab ozogamicin (MYLOTARG ®), lintuzumab, | Acute myelogenous leukemia |
| CD37 | Otlertuzumab | Cancer cells |
| CD38 | Daratumumab | Multiple myeloma |
| CD40 | Lucatumumab, dacetuzumab | multiple myeloma, non-Hodgkin's or Hodgkin's lymphoma |
| CD52 | Alemtuzumab (CAMPATH ®, MABCAMPATH ®, CAMPATH-1H ®) | Chronic lymphocytic leukemia |
| CD56 | Lorvotuzumab mertansine | small-cell lung cancer, ovarian cancer |
| CD70 | Vorsetuzumab mafodotin | Renal cell carcinoma |
| CD74 | Milatuzumab | Multiple myeloma |
| CD140 | Tovetumab | cancer |
| EpCAM | IGN101, oportuzumab monatox, tucotuzumab celmoleukin, adecatumumab | Epithelial tumors (breast, colon and lung) |
| CEA | Labetuzumab (CEA-CIDE ®) | Breast, colon and lung tumors |
| gpA33 | huA33 | Colorectal carcinoma |
| mesothelin | Amatuximab | Cancer cells |
| α-fetoprotein | $^{90}$Y-tacatuzumab tetraxetan | Tumor cells |
| IL-6 | Siltuximab | metastatic renal cell cancer, prostate cancer, and Castleman's disease |
| Mucins | Pemtumomab (THERAGYN ®), cantuzumab mertansine, $^{90}$Y clivatuzumab tetraxetanand, oregovomab (OVAREX ®) | Breast, colon, lung and ovarian tumors |
| PDGFR-alpha | Olaratumab | Solid tumors |
| TAG-72 | CC49 (minretumomab) | Breast, colon and lung tumors |
| CAIX | Girentuximab, cG250 | Renal cell carcinoma |
| PSMA | J591 | Prostate carcinoma |
| Folate-binding protein | MOv18 and MORAb-003 (farletuzumab) | Ovarian tumors |
| Scatter factor receptor kinase | Onartuzumab | Cancer cells |
| Gangliosides (e.g., GD2, GD3 and GM2) | 3F8, ch14.18, KW-2871 | Neuroectodermal tumors and some epithelial tumors |
| Cytokeratin | $^{99m}$Tc-Votumumab (HUMASPECT ®) | Colorectal tumors |
| Frizzled receptor | Vantictumab | cancer |
| Le$^y$ | hu3S193, IgN311 | Breast, colon, lung and prostate tumors |
| VEGF | Bevacizumab (AVASTIN ®) | Tumor vasculature |
| VEGFR | IM-2C6, CDP791 | Epithelium-derived solid tumors |
| Integrin αVβ3 | Etaracizumab (ABEGRIN ®), intetumumab | Tumor vasculature |
| Integrin α5β1 | Volociximab | Tumor vasculature |
| EGFR | Cetuximab (ERBITUX ®), panitumumab (VECTIBIX ®), nimotuzumab, necitumumab, zalutumumab, imgatuzumab, matuzumab, 806 | Glioma, lung, breast, colon, and head and neck tumors |

TABLE 2-continued

Exemplary therapeutic monoclonal antibodies for administration in combination with NK cells expressing CD16-V158

| Antigen | mAb | Target Tumor/Disease |
| --- | --- | --- |
| EGFL7 | Parsatuzumab | Cancer cells |
| ERBB2 | Trastuzumab (HERCLON ®; HERCEPTIN ®), pertuzumab (PERJETA ®; OMNITARG ®) | Breast, colon, lung, ovarian and prostate tumors |
| ERBB3 | Duligotumab, MM-121 | Breast, colon, lung, ovarian and prostate, tumors |
| Fibronectin | Radretumab | antineoplastic |
| HGF | Rilotumumab, ficlatuzumab | Solid tumors |
| HER3 | Patritumab | cancer |
| LOXL2 | Simtuzumab | fibrosis |
| MET | AMG 102, METMAB, SCH 900105 | Breast, ovary and lung tumors |
| IGF1R | Cixutumumab, dalotuzumab, figitumumab, ganitumab, robatumumab, teprotumumab, AVE1642, IMC-A12, MK-0646, R1507, and CP 751871 | Glioma, lung, breast, head and neck, prostate and thyroid cancer |
| IGLF2 | Dusigitumab | |
| EPHA3 | KB004, IIIA4 | Lung, kidney and colon tumors, melanoma, glioma and hematological malignancies |
| FR-alpha | Farletuzumab | Ovarian cancer |
| phosphatidyl-serine | Bavituximab | Cancer cells |
| Syndecan 1 | Indatuximab ravtansine | |
| SLAMF7 (CD319) | Elotuzumab | Multiple myeloma |
| TRAILR1 | Mapatumumab (HGS-ETR1) | Colon, lung and pancreas tumors and hematological malignancies |
| TRAILR2 | Conatumumab, lexatumumab, mapatumumab, tigatuzumab, HGS-ETR2, CS-1008 | cancer |
| RANKL | Denosumab (XGEVA ®) | Prostate cancer and bone metastases |
| FAP | Sibrotuzumab, and F19 | Colon, breast, lung, pancreas, and head and neck tumors |
| vimentin | Pritumumab | Brain cancer |
| Tenascin | 81C6 | Glioma, breast and prostate tumors |

EXAMPLES

The following examples are provided to illustrate certain particular features and/or embodiments. These examples should not be construed to limit the disclosure to the particular features or embodiments described.

Example 1

Materials and Methods

Cell Lines and Reagents: The human myelogenous leukemia line (erythroleukemia type) K562 (ATCC) and the acute monocytic leukemia cell line MOLM-14 (ATCC), and EBV-SMI-LCL were cultured in RPMI 1640 supplemented with 10% heat-inactivated fetal bovine serum (FBS, Sigma-Aldrich), 2 mM glutamine, and 100 U/mL penicillin, and 100 µg/mL streptomycin (Life Technologies). The 293T cell line, human embryonic kidney cell line 293 stably expressing SV40 large T antigen (from ATCC) was cultured in Dulbecco's modified Eagle's medium (DMEM; Invitrogen) supplemented with 2 mM L-glutamine, 100 U/mL penicillin, and 100 µg/mL streptomycin (Invitrogen) and 10% FBS. The cells were cultured under 95% humidity at 37° C. and 5% $CO_2$.

Culture and expansion of human peripheral blood-derived NK cells: Peripheral blood mononuclear cells (PBMC) from healthy donors were collected by apheresis (Amicus Separator; Fenwal, Lake Zurich, Ill., USA) on an institutional review board-approved protocol in the Department of Transfusion Medicine, National Institutes of Health (Bethesda, Md., USA). Cells were enriched by centrifugation over Ficoll density gradient medium. NK cells were isolated from donor PBMCs using the NK cell isolation kit from Miltenyi following the manufacturer's instructions. Where indicated NK cells were expanded for 11-21 days in NK cell media (X-VIVO™ 20 medium (Lonza) supplemented with 10% heat-inactivated human AB plasma (Sigma-Aldrich) and 500 IU/ml of recombinant human IL-2 (Roche)) in the presence of irradiated EBV-SMI-LCL cells at a ratio of 1:10. The cells were cultured at 37° C. and 6.5% $CO_2$. Half of the media was replaced with fresh NK cell media 5 days into the expansion. Thereafter, NK cells were counted and adjusted to 0.5-1×10⁶ cells/ml every 48 h, from day 7 until utilized in experiments.

Lentiviral vector system: The human immunodeficiency virus (HIV)-1-based lentiviral gene transfer vector used in this study was similar to a self-inactivating construct pRRL-CMV-eGFP-SIN-18 described by Dull et al. (*J Virol.* 72: 8463-8471, 1998) except that an additional 118-bp sequence containing the central poly purine tract (cPPT) had been introduced in the vector. In addition, the woodchuck hepatitis virus post-transcriptional regulatory element (WPRE)

backbone was included to augment transgene expression and/or viral vector titer. The internal cytomegalovirus (CMV) early promoter CMV promoter used to drive the transcription of transgene was replaced with the human phosphoglycerate kinase (PGK) promoter by polymerase chain reaction (PCR)-based amplification. The packaging plasmid pCMVΔR8.91 (devoid of all HIV-1 accessory genes) was used to express the HIV-1 gag, pol, tat, and rev genes and thereby produce lentiviral structural and regulatory proteins. The plasmid pMD.G carrying the vesicular stomatitis virus envelope G protein (VSV-G) coding sequence driven by the CMV promoter and followed by the β-globin polyadenylation site was used to pseudotype the vector particles. The plasmids pRRL-CMV-eGFP-SIN-18, pCMVΔR8.91, and pMD.G were kindly provided by Prof. D. Trono, Department of Genetics and Microbiology, CMU, Geneva, Switzerland.

Lentiviral vector production: Replication-defective lentiviral particles pseudotyped with VSV-G envelope were produced by 3-plasmid transient transfection of 293T cells with 12 µg of the gene transfer construct pRRLs-in.PPT.hPGK.eGFP.Wpre, 10 µg of pCMVΔR8.91, and 5 µg of pMD.G, using a calcium phosphate transfection kit (Clontech) as described previously (Chinnasamy et al., Blood 96:1309-1316. 2000). The transfection medium was replaced after 8 hours with fresh culture medium. Viral supernatants were harvested at 65 hours after transfection and filtered through 0.45 µm filters (Nalgene, Rochester, N.Y.). The viral supernatants were concentrated to 50× by ultracentrifugation at 50,000 g for 1.5 hours at 4° C.). Viral pellets were resuspended in X-VIVO™ 20 medium (Lonza) and stored frozen at −80° C. until use. Titers of viral supernatants were determined by quantification of p24 gag by enzyme-linked immunosorbent assay (ELISA) (Coulter Diagnostics, Hialeah, Fla.), and also by transducing 293T cells with serial dilutions of viral supernatants, followed by flow cytometry analysis of EGFP-positive cells, 48 hours after transduction. It was assumed that 1 ng of p24 is approximately equivalent to 1000 to 5000 transducing units. All lentiviral vector preparations were tested for the presence of replication-competent lentivirus (RCL) by transducing 293T cells and assaying culture medium for the presence of p24 gag after at least 5 cell passages. No RCL was detectable in any of the vector preparations tested.

Lentiviral transduction of primary human NK cells primed with cytokines or stimulated with LCL: Cultured human NK cells were transduced with concentrated lentiviral vector particles at a multiplicity of infection (MOI), in the presence of protamine sulfate (10 µg/ml, Sigma-Aldrich), in 24-well plate containing 1 ml/well of NK culture medium supplemented with IL-2 (500 IU/ml or 1000 IU/ml), IL-15 (10 ng/ml), or IL-2 (500 IU/ml) and IL15 (10 ng/ml). After 48 hours transduction, cells were washed and cultured in fresh NK cell culture medium containing IL-2 (500 IU/ml) in the presence or absence of irradiated EBV-SMI-LCL (LCL to NK ratio of 10:1). In some conditions, primary NK cells were co-cultured with EBV-SMI-LCL (LCL to NK ratio of 10:1) at different lengths of time prior to transduction with lentiviral vector for 48 hours and then cells were washed and cultured in fresh NK cell culture medium containing IL-2 (500 IU/ml). The viability of NK cultures was monitored periodically before and after transduction using trypan blue (Sigma) staining. The phenotype and eGFP expression were monitored at regular intervals by flow cytometry.

Flow cytometry: The cultured NK cells were phenotyped by flow cytometry at different time points post culture and expansion according to standard procedures. The following reagents were used in phenotypic characterization: anti-CD56 (NCAM-1), anti-CD3 (UCHT1), anti-CD16 (3G8), anti-TRAIL (RIK-2), anti-NKp46 (29A1.4), and IgG1 (MOPC21) from Becton Dickinson (BD); anti-KIR2DL1/DS1 (EB6), anti-KIR2DL2/3/DS2 (GL183), and anti-NKG2A (Z199) from Beckman Coulter; the anti-KIR3DL1 (Dx9), anti-CD57 (HCD57), NKp44 (Clone p44-8, FAS (clone DX2), CXCR3 (clone 12G5), CXCR4 (clone G025H7), and BV650-streptavidin from Biolegend; the anti-Lir-1 (HP-F1) from eBioscience; the anti-NKG2C (134591) from R&D Systems; LIVE/DEAD viability marker or propidium iodide (PI) from Life Technologies; biotinylated anti-KIR3DL2 (Dx31) primary antibody from UCSF. The BV650-streptavidin (Biolegend) was used to detect the biotinylated anti-KIR3DL2. Briefly, cells were mixed with appropriate concentrations of different dye-conjugated monoclonal antibodies (mAbs). After the addition of primary Ab and incubation for 20 minutes at room temperature, cells were washed with PBS containing 1% FBS. Propidium iodide (PI) or LIVE/DEAD staining was used for dead cell exclusion. All the data were acquired using the Canto II or Fortessa flow cytometer with FACS Diva software (BD Biosciences) and analyzed using the FlowJo software (Tree Star). In each sample, a minimum of 10,000 cells was acquired in the analysis region of viable cells, using log-amplified fluorescence and linearly amplified side- and forward-scatter signals. All samples were analyzed by setting appropriate gates around the lymphocyte population, using LIVE/DEAD or PI-negative cells. Consistency of analysis parameters was ascertained by calibrating the flow cytometer with calibrating beads (BD biosciences). EGFP expression in transduced cells was determined by detecting the % green fluorescence positive cells using a 530/30 nm band pass filter in the FL1 channel.

Cytotoxicity Assay: Natural killer cells were co-cultured at a ratio of 1:1 with either $^{51}$Cr-labeled K562 cells or Molm-14 cells in a final volume of 200 µl in 96-well plates at 37° C. and 5% $CO_2$. After 4 hours, supernatant was harvested onto a Luma plate. Counts were measured using a Perkin Elmer 1450 Microbeta Counter and specific target lysis was calculated using the following formula: [(NK cell-induced $^{51}$Cr release−spontaneous $^{51}$Cr release)/(maximum $^{51}$Cr release−spontaneous $^{51}$Cr release)×100].

Example 2

Effect of IL-2 Priming on Lentiviral Transduction of NK Cells

This example describes the effect of priming with IL-2 on transduction of NK cells using a lentiviral vector and characterization of the transduced NK cells.

Figure 3:
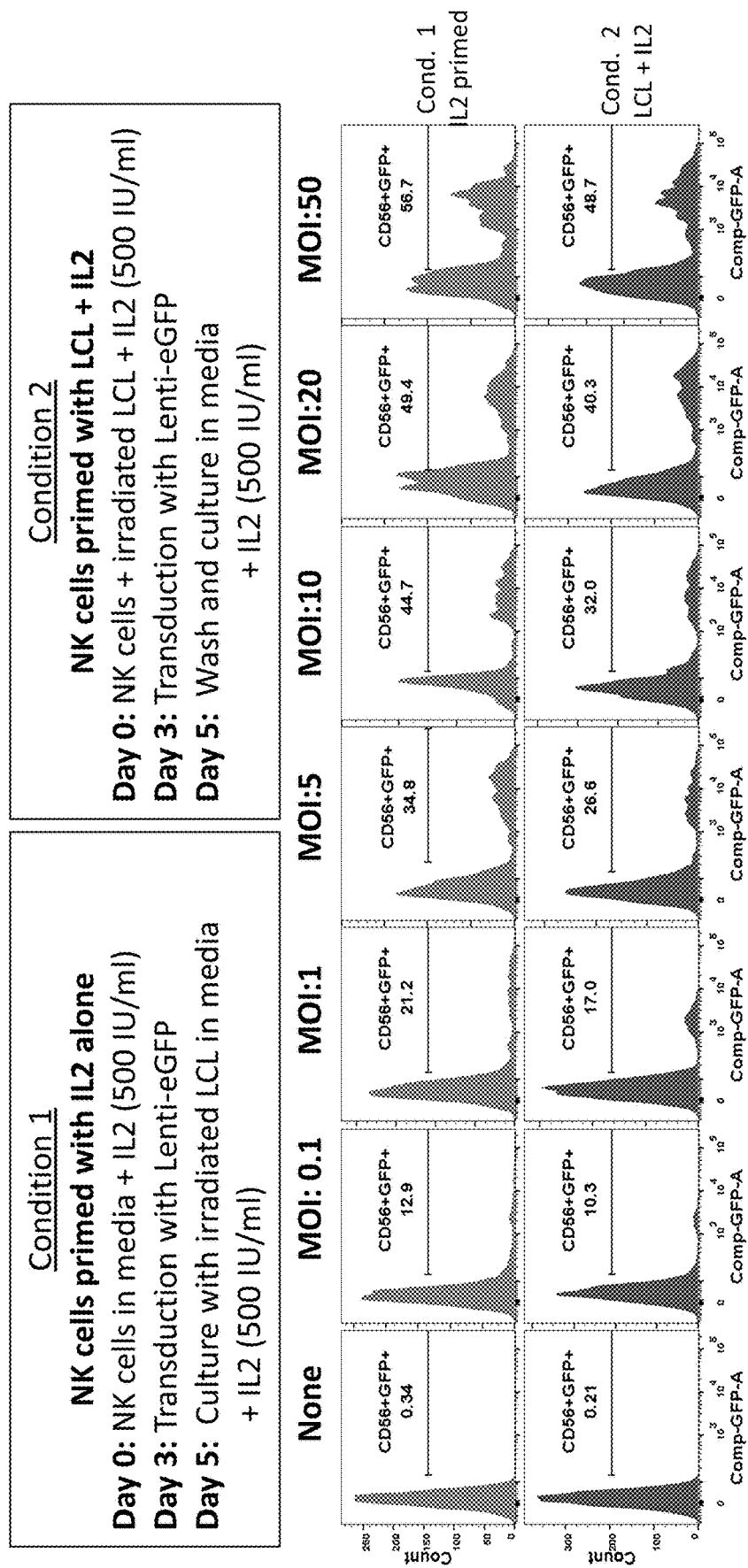
FIG. 3 is a series of panels showing expression of enhanced green fluorescent protein (eGFP) expression in CD56+ NK cells cultured in media and primed with IL-2 (500 IU/ml) prior to transduction (Condition 1) or CD56+ NK cells cultured on irradiated lymphoblastoid (LCL) cells and primed with interleukin-2 (IL-2; 500 IU/ml) prior to transduction (Condition 2). Analysis was by fluorescence-activated cell sorting (FACS) seven days post-transduction.

Conditions for priming NK cells prior to transduction and culture conditions post-transduction were evaluated. In initial experiments, priming of NK cells with IL-2 was evaluated. In one experiment, NK cells on LCL feeder cells were primed with 500 IU/ml IL-2 for three days prior to transduction with various multiplicity of infection (MOI) of lentiviral particles including an eGFP transgene. Cells were incubated with viral particles for two days, then viral particles were washed off and the cells were cultured with media including 500 IU/ml IL-2. In a second experiment, NK cells were primed with 500 IU/ml IL-2 for three days prior to transduction with lentiviral particles including the eGFP transgene. Cells were incubated for two days, then viral particles were washed off and the cells were cultured on irradiated LCL feeder cells with media including 500 IU/ml IL-2. eGFP expression was evaluated by FACS on day 7 post-transduction. eGFP expression on CD56+ cells was similar between the two conditions (FIG. 3), but was slightly higher in the cells primed with LCL and IL-2 and grown on IL-2 only post-transduction (Condition 1).

Figure 4:
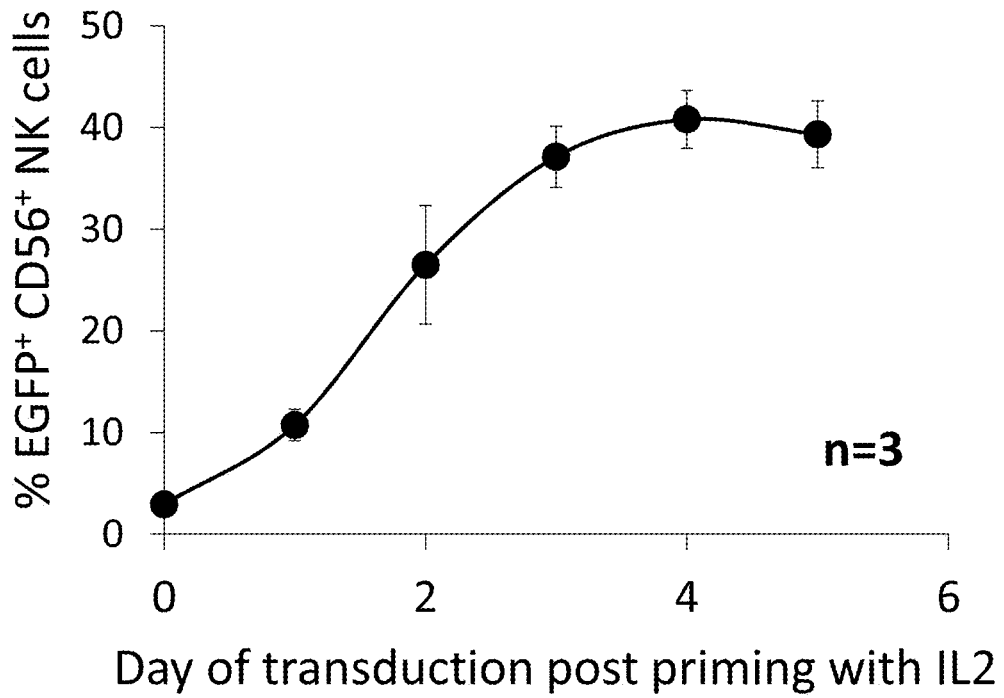
FIG. 4 is a graph showing transduction efficiency in CD56+ NK cells cultured in media containing IL-2 (500 IU/ml) for the indicated number of days prior to transduction. Two days after transduction, viral particles were removed and irradiated LCLs were added (LCL:NK ratio 10:1) with 500 IU/ml IL-2. eGFP expression was analyzed by FACS seven days post-transduction.
Figure 5A:
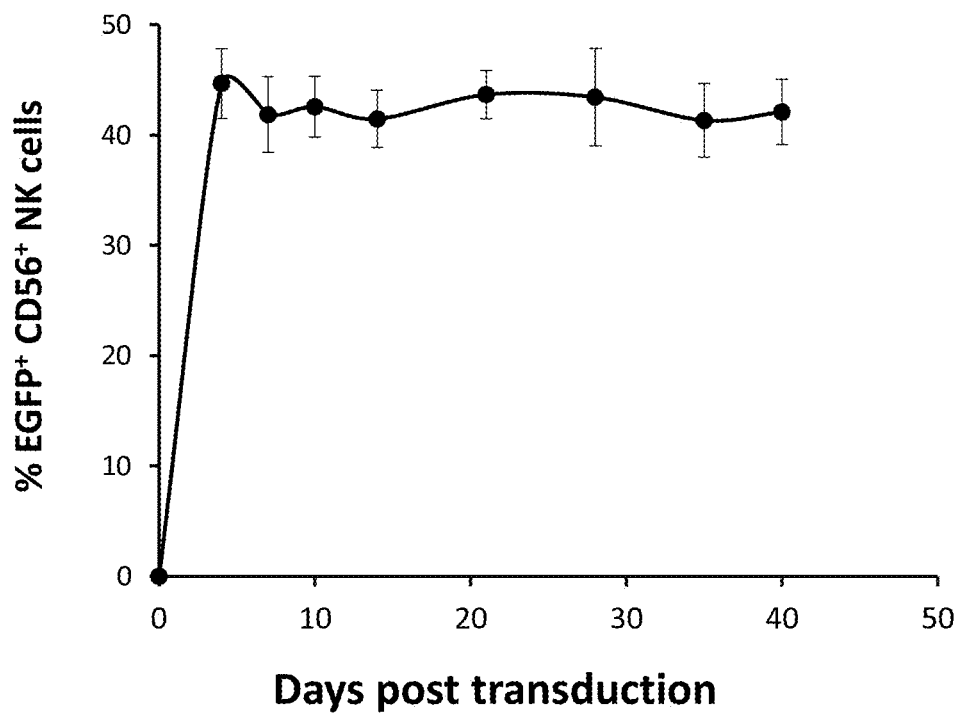
FIGS. 5A and 5B are graphs showing persistence of transgene expression (FIG. 5A) and cell viability (FIG. 5B)
Figure 5B:
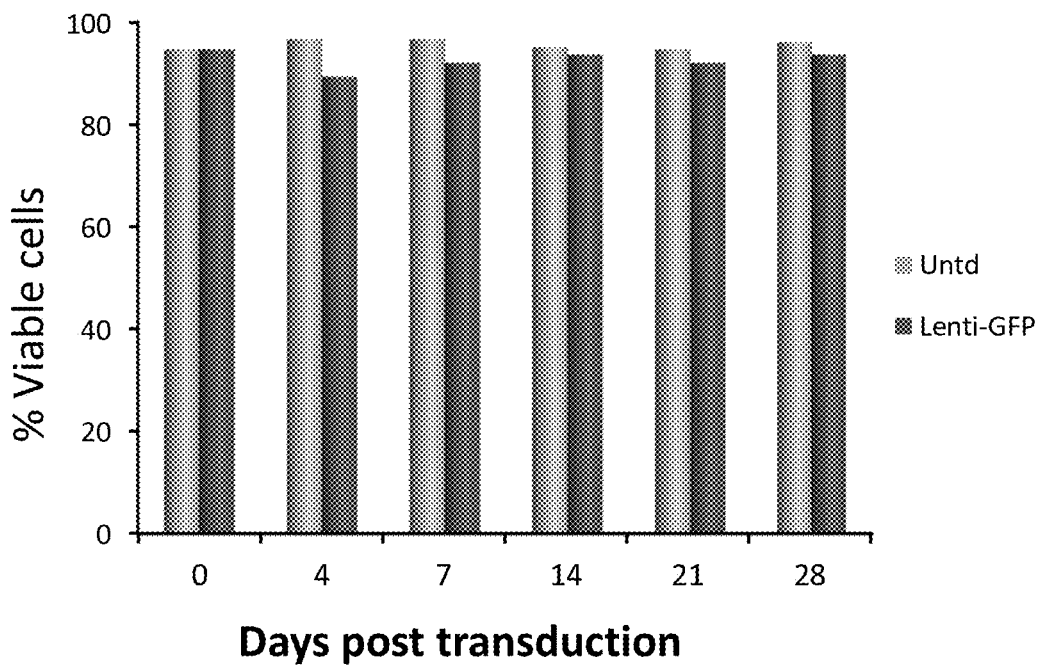

The impact of IL-2 priming on NK cell transduction was evaluated by priming NK cells with 500 IU/ml IL-2 for 1-5 days prior to transduction. At two days post-transduction, viral particles were removed and irradiated LCLs were added at a 10:1 ratio (LCL:NK cells) and the cells were maintained in medium containing 500 IU/ml IL-2. Priming with IL-2 for two or more days resulted in transduction efficiency of about 25% or more (FIG. 4). NK cells were also primed with medium containing IL-2 (500 IU/ml) for three days prior to transduction with at MOI 20. Two days post-transduction, viral particles were removed, irradiated LCLs (10:1 ratio LCL:NK cells) were added, and the cells were maintained in medium containing 500 IU/ml IL-2. Transgene expression remained stable for at least 40 days post-transduction (FIG. 5A) and cell viability remained comparable to untransduced cells for at least 28 days post-transduction (FIG. 5B).

The impact of LCL stimulation on NK cell transduction was also evaluated. NK cells were stimulated with irradiated LCLs in medium containing IL-2 (500 IU/ml) for 1-14 days before transduction. At two days post-transduction, viral particles were removed and the cells were maintained in medium containing 500 IU/ml IL-2. Transduction efficiency increased with the number of days of LCL stimulation prior to transduction (FIG. 6).

The persistence of transgene expression and cell viability post-transduction following LCL stimulation was tested. NK cells were cultured in medium containing 500 IU/ml IL-2 with irradiated LCLs (10:1 ratio with NK cells) and were transduced on day 0, 3, 7, or 14. At two days post-transduction, viral particles were removed and the cells were maintained in medium containing 500 IU/ml IL-2. eGFP expression remained stable up to 40 days post-transduction under each condition (FIG. 7, top). Cell viability up to 21 days post-transduction improved with priming for 3 days and was highest with priming for 7 days prior to transduction (FIG. 7, bottom).

Primary human peripheral NK cells from three subjects were cultured on irradiated LCLs with 500 IU/ml IL-2 for 14 days prior to transduction at MOI 10. Two days post-transduction, viral particles were removed and the cells were maintained in medium containing 500 IU/ml IL-2. eGFP expression was analyzed by FACS at 7 days post-transduction (FIG. 8A) and at additional time points post-transduction (FIG. 8B).

Example 3

Effect of IL-2 and IL-15 Priming on Lentiviral Transduction of NK Cells

This example describes the effect of priming with IL-2 and IL-15 on transduction of NK cells using a lentiviral vector and characterization of the transduced NK cells.

The effect of IL-15 priming, alone or in combination with IL-2, on NK cell transduction was evaluated. NK cells were cultured for 3 days in medium including IL-2 (500 IU/ml or 1000 IU/ml), IL-15 (10 ng/ml), or IL-2 (500 IU/ml) plus IL-15 (10 ng/ml) prior to transduction at MOI 20. Two days post-transduction, viral particles were removed, irradiated LCLs were added (10:1 ratio with NK cells), and the cells were maintained in medium containing 500 IU/ml IL-2. The NK cells primed with IL-2 plus IL-15 were more permissive to transduction than those primed with IL-2 or IL-15 alone (FIG. 9). The cells primed with IL-2 plus IL-15 also maintained long-term expression of the transgene at high frequencies for at least 28 days (FIG. 10).

Example 4

Effect of Lentiviral Transduction on NK Cell Phenotype

This example describes the phenotype of lentivirus transduced NK cells.

The effect of lentivirus transduction on NK cell phenotype was determined by analyzing expression of receptors clonally expressed on NK cells. NK cells were cultured for 3 days in medium including IL-2 (500 IU/ml) or IL-2 (500 IU/ml) plus IL-15 (10 ng/ml) prior to transduction at MOI 20. Two days post-transduction, viral particles were removed, irradiated LCLs were added (10:1 ratio with NK cells), and the cells were maintained in medium containing 500 IU/ml IL-2. Under both conditions, there was no impact on the NK cell phenotype (FIGS. 11 and 12).

To assess NK cell activity, NK cells from three different healthy donors were primed with irradiated LCL plus 500 IU/ml IL-2, IL-2 alone (500 IU/ml) or IL-2 (500 IU/ml) plus IL-15 (10 ng/ml) for three days prior to transduction. Cells were expanded with irradiated feeder LCLs plus 500 IU/ml IL-2 for 14 days and then their tumor killing capacity was tested against K562 cells (chronic myelogenous leukemia cells) or MOLM14 cells (acute myeloid leukemia cells). The cell killing activity of the transduced NK cells was similar to that of untransduced cells for all priming conditions (FIG. 13).

Example 5

Further Evaluation of Culture and Transduction Conditions

This example describes additional experiments evaluating conditions for activation, transduction, and expansion of NK cells.

The impact of IL-2 priming on NK cell transduction was evaluated by priming NK cells with 500 IU/ml IL-2 for 1-6 days prior to transduction with a lentiviral vector including a GFP transgene. At two days post-transduction, viral particles were removed and irradiated LCLs were added at a 10:1 ratio (LCL:NK cells) and the cells were maintained in medium containing 500 IU/ml IL-2. Transduction efficiency increased with 1-4 days of priming, then decreased slightly at days 5 and 6 (FIG. 14). Cell viability remained close to 100% with 1-3 days of priming, then dropped off (FIG. 14). Thus, 2-3 days of priming with IL-2 appears to provide the best balance of transduction efficiency and cell viability.

The impact of combinations of cytokines for priming was re-evaluated. NK cells were primed for 3 days with 500 IU/ml IL-2, 500 IU/ml IL-2+10 ng/ml or 50 ng/ml IL-15, 500 IU/ml IL-2+20 ng/ml IL-12, or 500 IU/ml IL-2+10 ng/ml IL-15+20 ng/ml IL-12. At two days post-transduction with a lentiviral vector including a GFP transgene, viral particles were removed and irradiated LCLs were added at a 10:1 ratio (LCL:NK cells) and the cells were maintained in medium containing 500 IU/ml IL-2. No significant differences in transduction efficiency were observed between IL-2 alone and the cytokine combinations (FIG. 15).

Transduction reagents were also tested for both transduction efficiency and effects on subsequent NK cell expansion. NK cells were primed for 3 days with 500 IU/ml IL-2 and then transduced with a lentiviral vector including a GFP transgene using protamine sulfate, Polybrene®, or Retronectin® reagents. At two days post-transduction, viral particles were removed and irradiated LCLs were added at a 10:1 ratio (LCL:NK cells) and the cells were maintained in medium containing 500 IU/ml IL-2. Including Polybrene® or Retronectin® reagent significantly increased transduction efficiency compared to protamine sulfate (FIG. 16A). Subsequent NK cell viability was significantly decreased in NK cells transduced using Polybrene® reagent compared to protamine sulfate, while viability was not significantly different between NK cells transduced using Polybrene® or Retronectin® reagents (FIG. 16B).

Various promoters were evaluated for NK cell transduction efficiency. Lentiviral vectors including a GFP transgene operably linked to a PGK, UBC, EF1A, EFS, SV40, CMV, CAG, or CBH promoter were constructed. NK cells were primed for 3 days with 500 IU/ml IL-2. At two days post-transduction with the lentiviral vector at MOI of 5, 20, or 100, viral particles were removed and irradiated LCLs were added at a 10:1 ratio (LCL:NK cells) and the cells were maintained in medium containing 500 IU/ml IL-2. All constructs tested resulted in GFP expression in the transduced NK cells (FIG. 17). PGK, EFS, and SV40 primers resulted in the greatest transduction efficiency. In addition, GFP expression was stable over 14 days expansion post-transduction, compared to expression at day 0 (FIG. 18).

Finally, function of transduced NK cells was evaluated. NK cells were primed for 3 days with 500 IU/ml IL-2. At two days post-transduction with a lentiviral vector including a GFP transgene linked to PGK, EFS, or SV40 promoter, viral particles were removed and irradiated LCLs were added at a 10:1 ratio (LCL:NK cells) and the cells were maintained in medium containing 500 IU/ml IL-2. The transduced cells exhibited equivalent degranulation compared to mock-transduced cells in response to K562 cells, as well as spontaneous and maximal degranulation in response to PMA/ionomycin (FIG. 19). The cells also exhibited equivalent CD107a expression (a marker of degranulation) and IFNγ and TNFα secretion in response to K562 cells or P/I compared to non-transduced cells (FIG. 20).

Example 6

Transduction of NK Cells with Additional Transgenes

This example describes transduction of NK cells with additional transgenes of interest.

A lentiviral vector including a nucleic acid encoding CXCR4 was constructed (FIG. 21A). NK cells were activated in 500 IU/ml IL-2 for 3 days prior to transduction with MOI 20. Transduced NK cells were expanded for 14 days with irradiated EBV-LCL 2 days following viral transduction. NK cells transduced with this vector showed increased expression of CXCR4 compared to non-transduced cells (FIG. 22A). A lentiviral vector including a nucleic acid encoding CXCR4 linked to a nucleic acid encoding a truncated CD34 molecule including the extracellular and transmembrane domains of CD34, but lacking the intracellular signaling domain was constructed (FIG. 21B). NK cells transduced with this vector (as described above) showed expression of CD34 and increased expression of CXCR4 compared to non-transduced cells (FIG. 22B).

Example 7

Evaluation of Transduced NK Cells in a Mouse Model

This example describes methods of evaluating the function and efficacy of modified NK cells expressing a heterologous nucleic acid in a mouse model of hyperproliferative disorder. However, one skilled in the art will recognize that methods that deviate from these specific methods can also be used to evaluate transduced NK cells in an animal model.

A mouse model of myeloma is produced by injecting immunodeficient mice (such as SCID, NOD/SCID, SCID-hu, or SCID-rab mice) with malignant plasma cells or by injecting C57BL/KalwRij mice with allogeneic malignant plasma cells (such as 5T2MM, 5T33, or 5TGM1 cells). In one example, multiple myeloma cell lines are injected in the tail vein of NSG mice and allowed to establish for 7-14 days prior to treating the mice with i.v. infusions of NK cells. Human NK cells are activated (500 IU/ml IL-2 for 2-3 days) and then transduced with a lentiviral vector including a nucleic acid encoding luciferase or CXCR4. Following expansion (14 days on EBV-LCL cells with 500 IU/ml IL-2), the modified NK cells (1-20 million cells) are administered to the mice.

Mice are sacrificed at 7, 14, and 21 days after the NK cell infusion and the % of myeloma cells in the bones (bone marrow flushed from the femurs) is determined to assess the impact of different NK cells (transduced versus non-transduced) on tumor burden. Survival and localization of the modified NK cells may be evaluated by bioluminescent imaging of mice injected with modified NK cells transduced with a luciferase-encoding vector.

Example 8

Method of Treating a Subject with a Hyperproliferative Disorder

This example describes methods of treating a subject with a hyperproliferative disorder with modified NK cells expressing a heterologous nucleic acid. However, one skilled in the art will appreciate that methods that deviate from these specific methods can also be used to successfully treat or inhibit a hyperproliferative disorder in a subject.

A subject with a hyperproliferative disorder, for example multiple myeloma, undergoes apheresis to collect peripheral blood mononuclear cells. NK cells (e.g., CD56-positive/CD3-negative cells) are isolated from the PBMCs by positive and/or negative selection using immune-magnetic methods. The isolated NK cells are cultured in medium containing 500 IU/ml IL-2 for 2 days. The NK cells are then contacted with lentivirus particles including a viral vector with a heterologous nucleic acid of interest for two days. The heterologous nucleic acid can be CXCR4, high affinity CD16, or both. In some examples, the vector also includes a truncated CD34 nucleic acid. The viral particles are removed and medium containing 500 IU/ml IL-2 and irradiated feeder cells (10:1 ratio feeder cells:NK cells) are added and the NK cells are expanded for 14-28 days. If the vector includes CD34t, prior to addition of IL-2 and feeder cells, CD34-expressing NK cells are enriched using CD34+ immuno-magnetic bead selection. The expanded NK cells can be cryopreserved for later use or can be formulated for administration to the subject (for example, in a pharmaceutically acceptable carrier). A composition comprising $10^6$ to $10^{12}$ of the expanded NK cells is administered to the subject intravenously. Patients with multiple myeloma expressing CD38 may also be treated with an anti-CD38 antibody such as daratumumab. The response of the subject's tumor is monitored for up to 5 years.

Example 9

Lentiviral Expression Vectors

Lentiviral expression vectors were constructed using Vectorbuilder design service (Cyagen Biosciences, Inc., Santa Clara, Calif.). The vectors included different promoters and EGFP or PGK promoter and different human proteins. The vectors have the sequences of SEQ ID NOs: 8-17, as shown in Table 3. The additional vector components and their positions in each sequence are shown in Table 4.

TABLE 3

Lentiviral expression vectors

| Vector Name | Inserted Sequences (Nucleotide positions) | SEQ ID NO: |
|---|---|---|
| pLV[Exp]-CMV>EGFP | Human cytomegalovirus immediate early promoter (1959-2547) and EGFP (2578-3297) | 8 |
| pLV[Exp]-EF1A>EGFP | Human eukaryotic translation elongation factor 1α (EF1A) promoter (1959-3137) and EGFP (3168-3887) | 9 |
| pLV[Exp]-EFS>EGFP | Short version of EF1A promoter (1959-2190) and EGFP (2221-2940) | 10 |
| pLV[Exp]-CAG>EGFP | Cytomegalovirus early enhancer fused with chicken β-actin (CAG) promoter (1959-3691) and EGFP (3722-4441) | 11 |
| pLV[Exp]-CBH>EGFP | Short version of CAG promoter (1959-2756) and EGFP (2787-3506) | 12 |
| pLV[Exp]-SV40>EGFP | Simian virus 40 early promoter (1959-2302) and EGFP (2333-3052) | 13 |
| pLV[Exp]-PGK>EGFP | Mouse phosphoglycerate kinase 1 (PGK) promoter (1959-2469) and EGFP (2500-3219) | 14 |
| pLV[Exp]-UBC>EGFP | Human ubiquitin C promoter (1959-3136) and EGFP (3167-3886) | 15 |
| pLV[Exp]-PGK>CXCR4 | PGK promoter (1959-2469) and human CXCR4 (2500-3558) | 16 |
| pLV[Exp]-PGK>CD34t:T2A:CXCR4 | PGK promoter (1959-2469) and truncated human CD34 (2500-3447), T2A peptide (3448-3510), human CXCR4 (3511-4569) | 17 |

TABLE 4

Additional vector components

| | SEQ ID NO: | | | | | | | | | |
|---|---|---|---|---|---|---|---|---|---|---|
| | 8 | 9 | 10 | 11 | 12 | 13 | 14 | 15 | 16 | 17 |
| RSV enhancer/promoter | 1-229 | 1-229 | 1-229 | 1-229 | 1-229 | 1-229 | 1-229 | 1-229 | 1-229 | 1-229 |
| HIV-1 truncated 5' LTR | 230-410 | 230-410 | 230-410 | 230-410 | 230-410 | 230-410 | 230-410 | 230-410 | 230-410 | 230-410 |
| HIV-1 psi packaging signal | 521-565 | 521-565 | 521-565 | 521-565 | 521-565 | 521-565 | 521-565 | 521-565 | 521-565 | 521-565 |
| HIV-1 Rev resp. element | 1075-1308 | 1075-1308 | 1075-1308 | 1075-1308 | 1075-1308 | 1075-1308 | 1075-1308 | 1075-1308 | 1075-1308 | 1075-1308 |
| cPPT | 1803-1920 | 1803-1920 | 1803-1920 | 1803-1920 | 1803-1920 | 1803-1920 | 1803-1920 | 1803-1920 | 1803-1920 | 1803-1920 |
| WPRE | 3336-3933 | 3926-4523 | 2979-3576 | 4480-5077 | 3545-4142 | 3091-3688 | 3258-3855 | 3925-4522 | 3597-4194 | 4608-5205 |
| HIV-1 truncated 3' LTR | 4015-4249 | 4605-4839 | 3658-3892 | 5159-5393 | 4224-4458 | 3770-4004 | 3937-4171 | 4604-4838 | 4276-4510 | 5287-5521 |
| SV40 early polyA signal | 4322-4456 | 4912-5046 | 3965-4099 | 5466-5600 | 4531-4665 | 4077-4211 | 4244-4378 | 4911-5045 | 4583-4717 | 5594-5728 |
| $Amp^R$ | 5410-6270 | 6000-6860 | 5053-5913 | 6554-7414 | 5619-6479 | 5165-6025 | 5332-6192 | 5999-6859 | 5671-6531 | 6682-7542 |
| pUC Ori | 6441-7029 | 7031-7619 | 6084-6672 | 7585-8173 | 6650-7238 | 6196-6784 | 6363-6951 | 7030-7618 | 6702-7290 | 7713-8301 |

Example 10

Activation of NK Cells with Feeder Cell Co-Culture

NK cells isolated from human peripheral blood were cultured with or without 100 Gy-irradiated SMI-LCL. After three days, cell cultures were centrifuged over Ficoll® media to remove dead cells, counted, and lentivirally transduced with pLV[Exp]-PGK>EGFP:T2A:Luc (SEQ ID NO: 14 with sequences encoding T2A peptide and codon optimized luciferase additionally inserted), using Retronectin® (Takara Clontech) coated plates. After an additional three days, cells were re-counted and re-plated with 10-fold excess of LCL. Cells were maintained throughout in X-VIVO™ 20 media (Lonza) supplemented with 10% heat-inactivated human AB serum, 500 IU/ml IL-2, and 2 mM GlutaMAX™ supplement and counted to determine the fold-expansion. Un-transduced NK cells initially cultured with LCL (10:1 ratio) without subsequent LCL additions were tested for comparison. Cells cultured with a 10-fold excess of LCL prior to transduction had improved expansion compared to cells that were not cultured with LCL prior to transduction and had a similar fold-expansion to un-transduced cells (FIG. 23).

In addition to, or as an alternative to the above, the following embodiments are described:

Embodiment 1 is directed to a method of producing natural killer (NK) cells comprising one or more heterologous nucleic acids, comprising culturing a population of isolated NK cells in the presence of interleukin-2 (IL-2) for at least two days to produce a population of activated NK cells; transducing the population of activated NK cells with a viral vector comprising one or more heterologous nucleic acids to produce a population of transduced NK cells; and culturing the population of transduced NK cells in the presence of IL-2 and irradiated feeder cells to produce an expanded population of transduced NK cells.

Embodiment 2 is directed to the method of embodiment 1, wherein: a) the population of NK cells is cultured in the presence of IL-2 and in the absence of irradiated feeder cells and/or the activated NK cells are transduced with the viral vector in the absence of irradiated feeder cells; or b) the population of NK cells is cultured in the presence of IL-2 and in the presence of irradiated feeder cells and/or the activated NK cells are transduced with the viral vector in the presence of irradiated feeder cells.

Embodiment 3 is directed to the method of embodiment 1 or embodiment 2, wherein culturing the population of isolated NK cells in the presence of one or more cytokines comprises culturing the population of isolated NK cells in cell culture medium containing 500 IU/ml IL-2.

Embodiment 4 is directed to the method of any one of embodiments 1 to 3, wherein the viral vector comprising one or more heterologous nucleic acids is a lentivirus vector.

Embodiment 5 is directed to the method of embodiment 4, wherein the lentivirus vector comprises or consists of a nucleic acid sequence with at least 90% sequence identify to any one of SEQ ID NOs: 8-17.

Embodiment 6 is directed to the method of any one of embodiments 1 to 5, wherein the ratio of the irradiated feeder cells to the transduced NK cells is 10:1.

Embodiment 7 is directed to the method of any one of embodiments 1 to 6, wherein the irradiated feeder cells comprise an Epstein-Barr virus transformed lymphoblastoid cell line or K562 cells.

Embodiment 8 is directed to the method of any one of embodiments 1 to 7, wherein the heterologous nucleic acid encodes: high affinity CD16 (CD16-V158), CXCR4, CCR7, CXCR3, CD34, double negative TGFβ type II receptor, or VLA-4, LFA-1; a chimeric antigen receptor (CAR) that specifically binds to an antigen expressed on tumor cells, wherein the heterologous nucleic acid encodes a CAR that specifically binds to CD19, CD20, CD33, CD138, CS1, GD2, HER2, erbB2-, CEA, EpCAM, NKG2D-L, or TRAIL-R1; a nucleic acid molecule encoding a truncated CD34 protein lacking an intracellular domain; and/or a short hairpin RNA (shRNA), small interfering RNA (siRNA), or an antisense nucleic acid.

Embodiment 9 is directed to the method of embodiment 2b, wherein the population of NK cells is cultured in the presence of IL-2 and in the presence of irradiated feeder cells to produce a population of activated NK cells and the feeder cells are substantially separated from the activated NK cells using CD19 immunodepletion.

Embodiment 10 is directed to 1 method of treating a subject with a tumor, hyperproliferative disease, or viral infection, comprising: obtaining a population of isolated natural killer (NK) cells from the subject or a donor; culturing a population of isolated NK cells in the presence of interleukin-2 (IL-2) for at least two days to produce a population of activated NK cells; transducing the population of activated NK cells with a viral vector comprising one or more heterologous nucleic acids to produce a population of transduced NK cells; culturing the population of transduced NK cells in the presence of IL-2 and irradiated feeder cells to produce an expanded population of transduced NK cells; and administering a composition comprising the expanded population of transduced NK cells to the subject.

Embodiment 11 is directed to the method of embodiment 10, wherein: a) the population of NK cells is cultured in the presence of IL-2 and in the absence of irradiated feeder cells; and/or the activated NK cells are transduced with the viral vector in the absence of irradiated feeder cells; or b) the population of NK cells is cultured in the presence of IL-2 and in the irradiated feeder cells; and/or the activated NK cells are transduced with the viral vector in the presence of irradiated feeder cells.

Embodiment 12 is directed to the method of embodiment 10 or 11, wherein culturing the population of isolated NK cells in the presence of one or more cytokines comprises culturing the population of isolated NK cells in cell culture medium containing 500 IU/ml IL-2.

Embodiment 13 is directed to the method of any one of embodiments 10 to 12, wherein the viral vector comprising one or more heterologous nucleic acids is a lentivirus vector.

Embodiment 14 is directed to the method of embodiment 13, wherein the lentivirus vector comprises or consists of a nucleic acid sequence with at least 90% sequence identify to any one of SEQ ID NOs: 8-17.

Embodiment 15 is directed to the method of embodiment 13, wherein the lentivirus vector comprises a nucleic acid of interest operably linked to a PGK, EFS, or SV40 promoter.

Embodiment 16 is directed to the method of any one of embodiments 10 to 15, wherein the ratio of the irradiated feeder cells to the transduced NK cells is 10:1.

Embodiment 17 is directed to the method of any one of embodiments 10 to 16, wherein the irradiated feeder cells comprise an Epstein-Barr virus transformed lymphoblastoid cell line or K562 cells.

Embodiment 18 is directed to the method of embodiments 10 to 17, wherein the heterologous nucleic acid encodes: high affinity CD16 (CD16-V158), CXCR4, CCR7, CXCR3, CD34, double negative TGFβ type II receptor, or VLA-4, LFA-1; a chimeric antigen receptor (CAR) that specifically binds to an antigen expressed on tumor cells, wherein the heterologous nucleic acid encodes a CAR that specifically binds to CD19, CD20, CD33, CD138, CS1, GD2, HER2, erbB2-, CEA, EpCAM, NKG2D-L, or TRAIL-R1; a nucleic acid molecule encoding a truncated CD34 protein lacking an intracellular domain; and/or a short hairpin RNA (shRNA), small interfering RNA (siRNA), or an antisense nucleic acid.

Embodiment 19 is directed to the method of embodiment 11b, wherein the population of NK cells is cultured in the presence of IL-2 and in the presence of irradiated feeder cells to produce a population of activated NK cells and the feeder cells are substantially separated from the activated NK cells using CD19 immunodepletion.

Embodiment 20 is directed to the method of any one of embodiments 10 to 19, wherein the composition comprising the expanded population of transduced NK cells further comprises a pharmaceutically acceptable carrier.

Embodiment 21 is directed to natural killer cells comprising one or more heterologous nucleic acids produced by the method of any one of embodiments 1 to 9.

Embodiment 22 is directed to a composition comprising natural killer cells comprising one or more heterologous nucleic acids and a pharmaceutically acceptable carrier, wherein the natural killer cells are produced by the method of any one of embodiments 10 to 20.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A method of producing natural killer (NK) cells comprising one or more heterologous nucleic acids, comprising:
    culturing a population of isolated NK cells in the presence of 500 IU/ml interleukin-2 (IL-2) and in the absence of irradiated feeder cells for 2-3 days to produce a population of activated NK cells;
    transducing the population of activated NK cells with a viral vector comprising one or more heterologous nucleic acids to produce a population of transduced NK cells; and
    culturing the population of transduced NK cells in the presence of 500 IU/ml IL-2 and irradiated feeder cells to produce an expanded population of transduced NK cells.

2. The method of claim 1, wherein the viral vector comprising one or more heterologous nucleic acids is a lentivirus vector.

3. The method of claim 2, wherein the lentivirus vector comprises or consists of a nucleic acid sequence with at least 90% sequence identity to any one of SEQ ID NOs: 8-17.

4. The method of claim 1, wherein the ratio of the irradiated feeder cells to the transduced NK cells is 2:1 to 20:1.

5. The method of claim 1, wherein the irradiated feeder cells comprise an Epstein-Barr virus transformed lymphoblastoid cell line or K562 cells.

6. The method of claim 1, wherein the heterologous nucleic acid encodes:
    high affinity CD16 (CD16-V158), CXCR4, CCR7, CXCR3, CD34, double negative TGFβ type II receptor, or VLA-4, LFA-1;
    a chimeric antigen receptor (CAR) that specifically binds to an antigen expressed on tumor cells;
    a nucleic acid molecule encoding a truncated CD34 protein lacking an intracellular domain; and/or
    a short hairpin RNA (shRNA), small interfering RNA (siRNA), or an antisense nucleic acid.

7. The method of claim 1, further comprising culturing the population of isolated NK cells in the presence of IL-15, IL-21, or both.

8. The method of claim 7, wherein the population of isolated NK cells is cultured in the presence of 10 ng/ml IL-15, 20 ng/ml IL-21, or both.

9. The method of claim 6, wherein the heterologous nucleic acid encodes a CAR that specifically binds to CD19, CD20, CD33, CD138, CS1, GD2, HER2, erbB2, CEA, EpCAM, NKG2D-L, or TRAIL-R1.

10. The method of claim 4, wherein the ratio of the irradiated feeder cells to the transduced NK cells is 10:1.

11. A method of treating a subject with a tumor, hematological malignancy, or viral infection, comprising:
    obtaining a population of isolated natural killer (NK) cells from the subject or a donor;
    culturing a population of isolated NK cells in the presence of 500 IU/ml interleukin-2 (IL-2) and in the absence of irradiated feeder cells for 2-3 days to produce a population of activated NK cells;
    transducing the population of activated NK cells with a viral vector comprising one or more heterologous nucleic acids to produce a population of transduced NK cells;
    culturing the population of transduced NK cells in the presence of 500 IU/ml IL-2 and irradiated feeder cells to produce an expanded population of transduced NK cells; and
    administering a composition comprising the expanded population of transduced NK cells to the subject.

12. The method of claim 11, wherein the viral vector comprising one or more heterologous nucleic acids is a lentivirus vector.

13. The method of claim 12, wherein the lentivirus vector comprises or consists of a nucleic acid sequence with at least 90% sequence identity to any one of SEQ ID NOs: 8-17.

14. The method of claim 12, wherein the lentivirus vector comprises a nucleic acid of interest operably linked to a PGK, EFS, or SV40 promoter.

15. The method of claim 11, wherein the ratio of the irradiated feeder cells to the transduced NK cells is 2:1 to 20:1.

16. The method of claim 11, wherein the irradiated feeder cells comprise an Epstein-Barr virus transformed lymphoblastoid cell line or K562 cells.

17. The method of claim 11, wherein the heterologous nucleic acid encodes:
    high affinity CD16 (CD16-V158), CXCR4, CCR7, CXCR3, CD34, double negative TGFβ type II receptor, or VLA-4, LFA-1;
    a chimeric antigen receptor (CAR) that specifically binds to an antigen expressed on tumor cells;
    a nucleic acid molecule encoding a truncated CD34 protein lacking an intracellular domain; and/or
    a short hairpin RNA (shRNA), small interfering RNA (siRNA), or an antisense nucleic acid.

18. The method of claim 11, wherein the composition comprising the expanded population of transduced NK cells further comprises a pharmaceutically acceptable carrier.

19. The method of claim 11, further comprising culturing the population of isolated NK cells in the presence of IL-15, IL-21, or both.

20. The method of claim 19, wherein the population of isolated NK cells is cultured in the presence of 10 ng/ml IL-15, 20 ng/ml IL-21, or both.

21. The method of claim 17, wherein the heterologous nucleic acid encodes a CAR that specifically binds to CD19, CD20, CD33, CD138, CS1, GD2, HER2, erbB2, CEA, EpCAM, NKG2D-L, or TRAIL-R1.

* * * * *